(12) United States Patent
    Birk et al.

(10) Patent No.: US 9,072,579 B2
(45) Date of Patent: Jul. 7, 2015

(54) BARIATRIC DEVICE AND METHOD FOR WEIGHT LOSS

(75) Inventors: Janel Birk, Oxnard, CA (US); Daniel Dongelmans, Oxnard, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 254 days.

(21) Appl. No.: 13/503,285

(22) PCT Filed: Oct. 21, 2010

(86) PCT No.: PCT/US2010/053619
    § 371 (c)(1),
    (2), (4) Date: Apr. 20, 2012

(87) PCT Pub. No.: WO2011/050208
    PCT Pub. Date: Apr. 28, 2011

(65) Prior Publication Data
    US 2012/0232577 A1    Sep. 13, 2012

Related U.S. Application Data

(63) Continuation of application No. PCT/US2010/041774, filed on Jul. 13, 2010.

(60) Provisional application No. 61/253,816, filed on Oct. 21, 2009, provisional application No. 61/262,040, filed on Nov. 17, 2009, provisional application No. 61/262,045, filed on Nov. 17, 2009, provisional application No. 61/264,651, filed on Nov. 25, 2009.

(51) Int. Cl.
    *A61F 5/00*    (2006.01)
    *A61F 2/04*    (2013.01)

(52) U.S. Cl.
    CPC ............. *A61F 5/0013* (2013.01); *A61F 5/0003* (2013.01); *A61F 5/0036* (2013.01); *A61F 2002/045* (2013.01)

(58) Field of Classification Search
    CPC ... A61F 5/0003; A61F 5/0013; A61F 5/0036; A61F 5/0076; A61F 5/0079; A61F 5/0086; A61F 5/0089; A61F 5/003; A61F 2002/045; A61F 5/0073
    USPC ......... 606/191, 192; 623/23.64, 23.65, 23.67, 623/23.68
    See application file for complete search history.

(56) References Cited

U.S. PATENT DOCUMENTS

| 4,416,267 A | 11/1983 | Garren et al. |
| 4,607,618 A | 8/1986 | Angelchik |

(Continued)

FOREIGN PATENT DOCUMENTS

| DE | 102007025312 | 11/2008 |
| EP | 1397998 | 3/2004 |

(Continued)

*Primary Examiner* — Ryan Severson
*Assistant Examiner* — Christian Knauss
(74) *Attorney, Agent, or Firm* — Gordon & Jacobson, PC

(57) ABSTRACT

A bariatric device for use in inducing weight loss, comprising a cardiac element, a pyloric element, and a connecting element between the two other elements, wherein the connecting element provides structure between the cardiac and pyloric elements, keeping them largely in place and at least intermittently touching and applying pressure to the stomach's cardiac, adjacent fundic and pyloric regions, respectively, which produces a satiety signal to the user, giving the recipient a feeling of fullness and reducing his or her hunger feelings. Alternatively, the cardiac and pyloric elements may be symmetrical, so that the device can orient itself either way in the stomach and still achieve the weight loss function.

12 Claims, 38 Drawing Sheets

(56) References Cited

U.S. PATENT DOCUMENTS

| | | | |
|---|---|---|---|
| 4,648,383 A | 3/1987 | Angelchik | |
| 4,739,758 A | 4/1988 | Lai et al. | |
| 4,774,956 A | 10/1988 | Kruse et al. | |
| 4,844,068 A | 7/1989 | Arata et al. | |
| 4,899,747 A | 2/1990 | Garren et al. | |
| 4,925,446 A | 5/1990 | Garay et al. | |
| 5,259,399 A | 11/1993 | Brown | |
| 5,312,343 A | 5/1994 | Krog et al. | |
| 5,820,584 A | 10/1998 | Crabb | |
| 6,264,700 B1 | 7/2001 | Kilcoyne et al. | |
| 6,322,538 B1 | 11/2001 | Elbert et al. | |
| 6,454,785 B2 | 9/2002 | De Hoyos Garza | |
| 6,540,789 B1 | 4/2003 | Silverman et al. | |
| 6,579,301 B1 | 6/2003 | Bales et al. | |
| 6,675,809 B2 | 1/2004 | Stack et al. | |
| 6,733,512 B2 | 5/2004 | McGhan | |
| 6,746,460 B2* | 6/2004 | Gannoe et al. | 606/153 |
| 6,845,776 B2 | 1/2005 | Stack et al. | |
| 6,981,978 B2* | 1/2006 | Gannoe | 606/153 |
| 6,981,980 B2 | 1/2006 | Sampson et al. | |
| 6,994,095 B2 | 2/2006 | Burnett | |
| 7,008,419 B2 | 3/2006 | Shadduck | |
| 7,033,384 B2 | 4/2006 | Gannoe et al. | |
| 7,037,344 B2* | 5/2006 | Kagan et al. | 623/23.65 |
| 7,056,305 B2 | 6/2006 | Garza Alvarez | |
| 7,090,699 B2 | 8/2006 | Geitz | |
| 7,214,233 B2 | 5/2007 | Gannoe et al. | |
| 7,220,237 B2 | 5/2007 | Gannoe et al. | |
| 7,220,284 B2 | 5/2007 | Kagan et al. | |
| 7,223,277 B2 | 5/2007 | DeLegge | |
| 7,320,696 B2 | 1/2008 | Gazi et al. | |
| 7,347,875 B2 | 3/2008 | Levine et al. | |
| 7,354,454 B2 | 4/2008 | Stack et al. | |
| 7,476,256 B2 | 1/2009 | Meade et al. | |
| 7,510,559 B2 | 3/2009 | Deem et al. | |
| 7,608,114 B2 | 10/2009 | Levine et al. | |
| 7,682,330 B2 | 3/2010 | Meade et al. | |
| 7,695,446 B2 | 4/2010 | Levine et al. | |
| 7,699,863 B2 | 4/2010 | Marco et al. | |
| 7,753,870 B2 | 7/2010 | Demarais et al. | |
| 7,771,382 B2 | 8/2010 | Levine et al. | |
| 7,794,447 B2 | 9/2010 | Dann et al. | |
| 7,815,589 B2 | 10/2010 | Meade et al. | |
| 7,837,643 B2 | 11/2010 | Levine et al. | |
| 7,841,503 B2 | 11/2010 | Sonnenschein et al. | |
| 7,931,693 B2 | 4/2011 | Binmoeller | |
| 7,981,162 B2 | 7/2011 | Stack et al. | |
| 8,029,455 B2 | 10/2011 | Stack et al. | |
| 8,032,223 B2 | 10/2011 | Imran | |
| 8,092,482 B2* | 1/2012 | Gannoe et al. | 606/194 |
| 2002/0055757 A1* | 5/2002 | Torre et al. | 606/192 |
| 2003/0109935 A1 | 6/2003 | Geitz | |
| 2003/0153905 A1 | 8/2003 | Edwards et al. | |
| 2004/0039452 A1* | 2/2004 | Bessler | 623/23.65 |
| 2004/0044357 A1 | 3/2004 | Gannoe et al. | |
| 2004/0092892 A1 | 5/2004 | Kagan et al. | |
| 2004/0117031 A1* | 6/2004 | Stack et al. | 623/23.65 |
| 2004/0122452 A1 | 6/2004 | Deem et al. | |
| 2004/0122453 A1 | 6/2004 | Deem et al. | |
| 2004/0267378 A1* | 12/2004 | Gazi et al. | 623/23.67 |
| 2005/0049718 A1 | 3/2005 | Dann et al. | |
| 2005/0055039 A1 | 3/2005 | Burnett et al. | |
| 2005/0080444 A1* | 4/2005 | Kraemer et al. | 606/192 |
| 2005/0085923 A1 | 4/2005 | Levine et al. | |
| 2005/0096692 A1 | 5/2005 | Linder et al. | |
| 2005/0159769 A1* | 7/2005 | Alverdy | 606/192 |
| 2005/0192614 A1 | 9/2005 | Binmoeller | |
| 2005/0197714 A1 | 9/2005 | Sayet | |
| 2005/0228504 A1* | 10/2005 | Demarais | 623/23.65 |
| 2005/0267595 A1* | 12/2005 | Chen et al. | 623/23.65 |
| 2005/0267596 A1 | 12/2005 | Chen et al. | |
| 2005/0273060 A1 | 12/2005 | Levy et al. | |
| 2006/0178691 A1 | 8/2006 | Binmoeller | |
| 2006/0252983 A1 | 11/2006 | Lembo et al. | |
| 2007/0010864 A1 | 1/2007 | Dann et al. | |
| 2007/0016262 A1 | 1/2007 | Gross et al. | |
| 2007/0021761 A1 | 1/2007 | Phillips | |
| 2007/0078476 A1 | 4/2007 | Hull, Sr. et al. | |
| 2007/0083224 A1* | 4/2007 | Hively | 606/192 |
| 2007/0100368 A1 | 5/2007 | Quijano et al. | |
| 2007/0118168 A1 | 5/2007 | Lointier et al. | |
| 2007/0156013 A1 | 7/2007 | Birk | |
| 2007/0173881 A1 | 7/2007 | Birk et al. | |
| 2007/0185374 A1 | 8/2007 | Kick et al. | |
| 2007/0239284 A1 | 10/2007 | Skerven et al. | |
| 2007/0265598 A1 | 11/2007 | Karasik | |
| 2007/0293716 A1 | 12/2007 | Baker et al. | |
| 2008/0015618 A1 | 1/2008 | Sonnenschein et al. | |
| 2008/0033574 A1* | 2/2008 | Bessler et al. | 623/23.68 |
| 2008/0058840 A1* | 3/2008 | Albrecht et al. | 606/153 |
| 2008/0058887 A1* | 3/2008 | Griffin et al. | 607/40 |
| 2008/0097513 A1 | 4/2008 | Kaji et al. | |
| 2008/0161935 A1* | 7/2008 | Albrecht et al. | 623/23.65 |
| 2008/0208241 A1 | 8/2008 | Weiner et al. | |
| 2008/0221595 A1 | 9/2008 | Surti | |
| 2008/0234718 A1 | 9/2008 | Paganon et al. | |
| 2008/0234834 A1 | 9/2008 | Meade et al. | |
| 2008/0243166 A1 | 10/2008 | Paganon et al. | |
| 2008/0249635 A1 | 10/2008 | Weitzner et al. | |
| 2008/0255678 A1 | 10/2008 | Cully et al. | |
| 2008/0262529 A1 | 10/2008 | Jacques | |
| 2009/0012553 A1* | 1/2009 | Swain et al. | 606/191 |
| 2009/0082644 A1* | 3/2009 | Li | 600/302 |
| 2009/0093767 A1* | 4/2009 | Kelleher | 604/175 |
| 2009/0093839 A1* | 4/2009 | Kelleher | 606/192 |
| 2009/0149879 A1* | 6/2009 | Dillon | 606/192 |
| 2009/0198210 A1 | 8/2009 | Burnett et al. | |
| 2009/0259246 A1 | 10/2009 | Eskaros et al. | |
| 2009/0275973 A1 | 11/2009 | Chen et al. | |
| 2009/0287231 A1 | 11/2009 | Brooks et al. | |
| 2009/0299486 A1 | 12/2009 | Shohat et al. | |
| 2009/0312597 A1 | 12/2009 | Bar et al. | |
| 2010/0030017 A1 | 2/2010 | Baker et al. | |
| 2010/0049224 A1 | 2/2010 | Vargas | |
| 2010/0100115 A1 | 4/2010 | Soetermans et al. | |
| 2010/0121371 A1 | 5/2010 | Brooks et al. | |
| 2010/0168782 A1 | 7/2010 | Hancock | |
| 2010/0249822 A1 | 9/2010 | Nihalani | |
| 2010/0256713 A1* | 10/2010 | Edwards et al. | 607/105 |
| 2010/0256775 A1 | 10/2010 | Belhe et al. | |
| 2010/0256776 A1 | 10/2010 | Levine et al. | |
| 2010/0305590 A1 | 12/2010 | Holmes et al. | |
| 2010/0331756 A1 | 12/2010 | Meade et al. | |

FOREIGN PATENT DOCUMENTS

| | | |
|---|---|---|
| EP | 1774929 | 4/2007 |
| FR | 2892297 | 4/2007 |
| FR | 2941617 | 8/2010 |
| WO | WO8800027 | 1/1988 |
| WO | WO0032092 | 6/2000 |
| WO | WO2005094257 | 10/2005 |
| WO | WO2005097012 | 10/2005 |
| WO | WO2005110280 | 11/2005 |
| WO | WO2006044640 | 4/2006 |
| WO | WO2006111961 | 10/2006 |
| WO | WO2006118744 | 11/2006 |
| WO | WO2007027812 | 3/2007 |
| WO | WO2007053556 | 5/2007 |
| WO | WO2007076021 | 7/2007 |
| WO | WO2007092390 | 8/2007 |
| WO | WO2007110866 | 10/2007 |
| WO | WO2008101048 | 8/2008 |
| WO | WO2008112894 | 9/2008 |
| WO | WO2008132745 | 11/2008 |
| WO | WO2010042062 | 4/2010 |
| WO | WO2010074712 | 7/2010 |
| WO | WO2010087757 | 8/2010 |
| WO | WO2010117641 | 10/2010 |

* cited by examiner

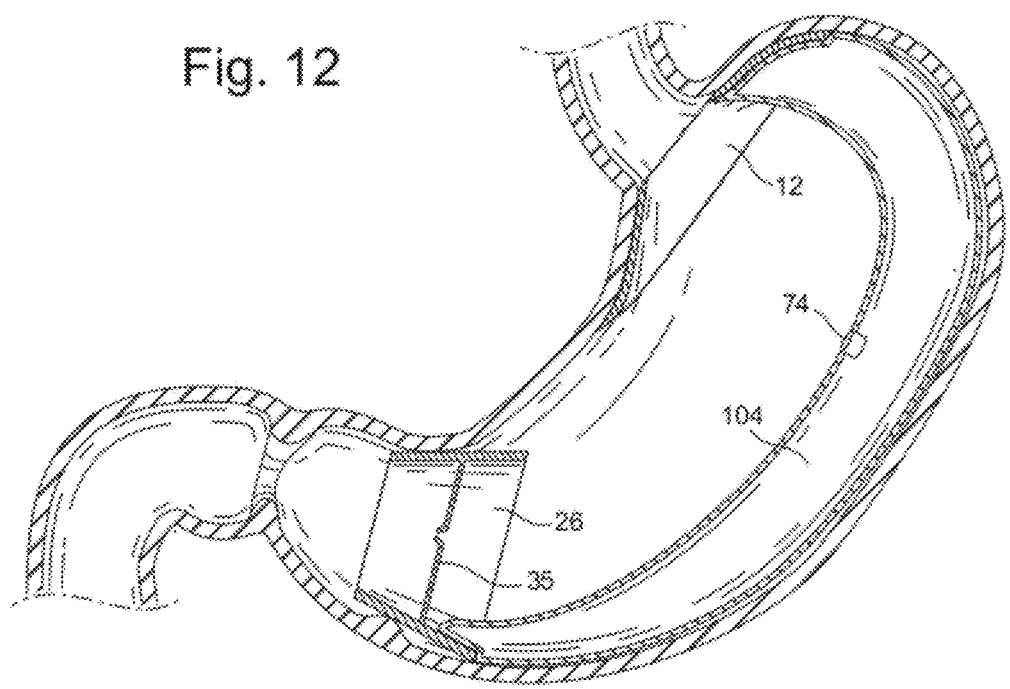

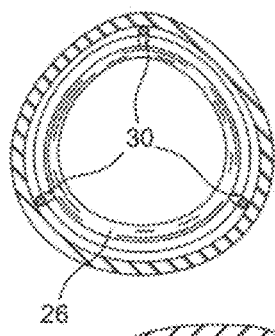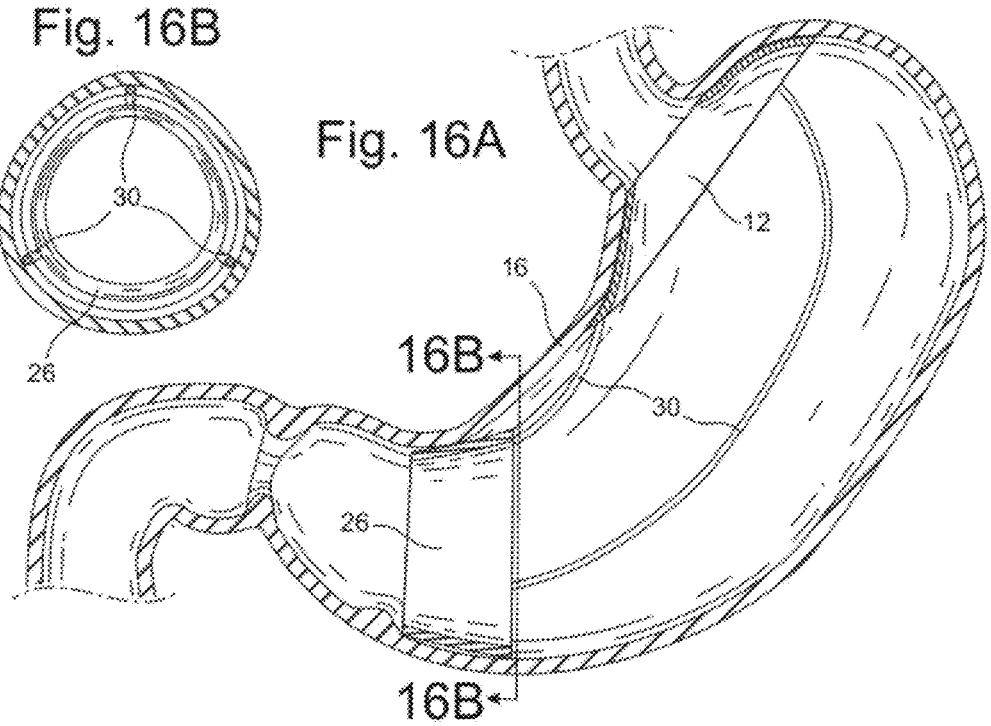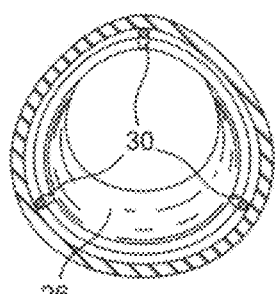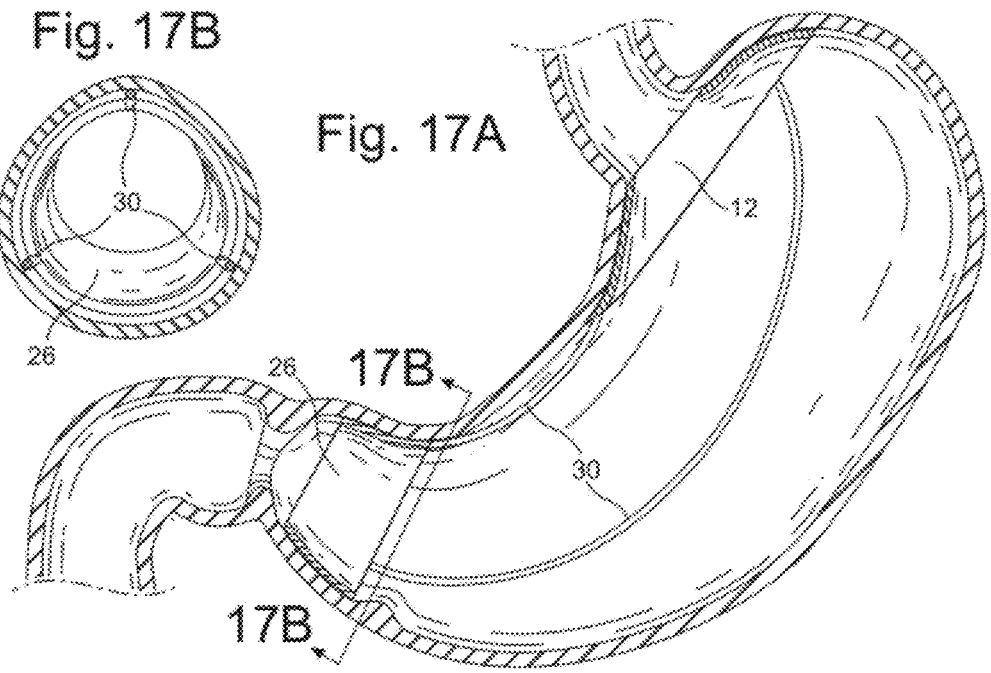

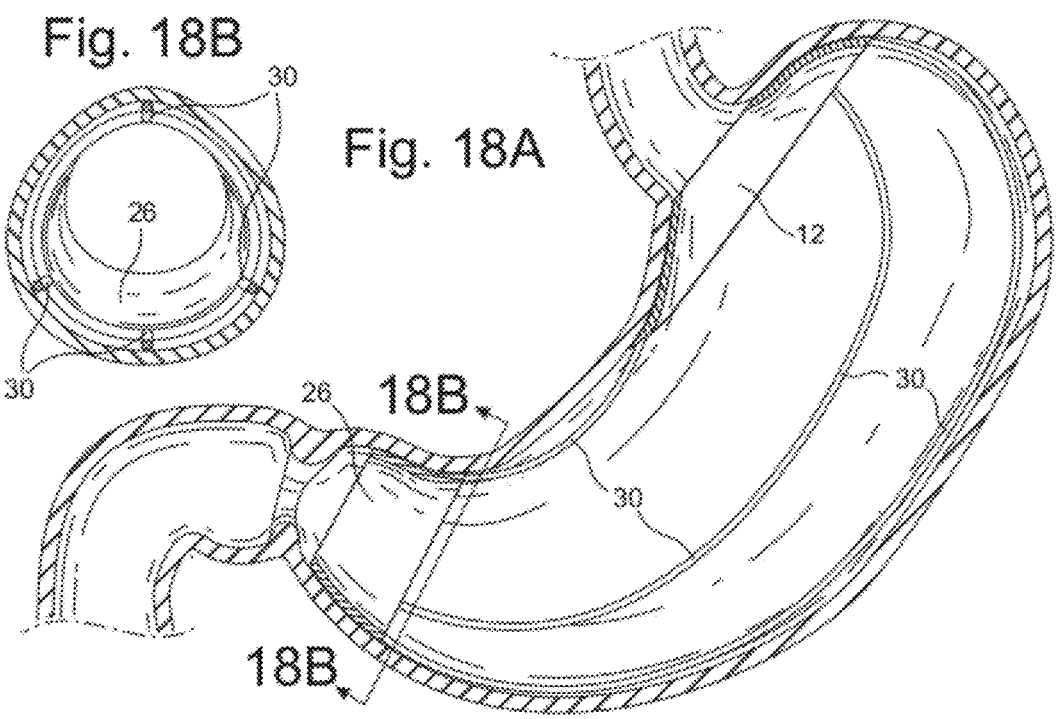
Fig. 18B
Fig. 18A
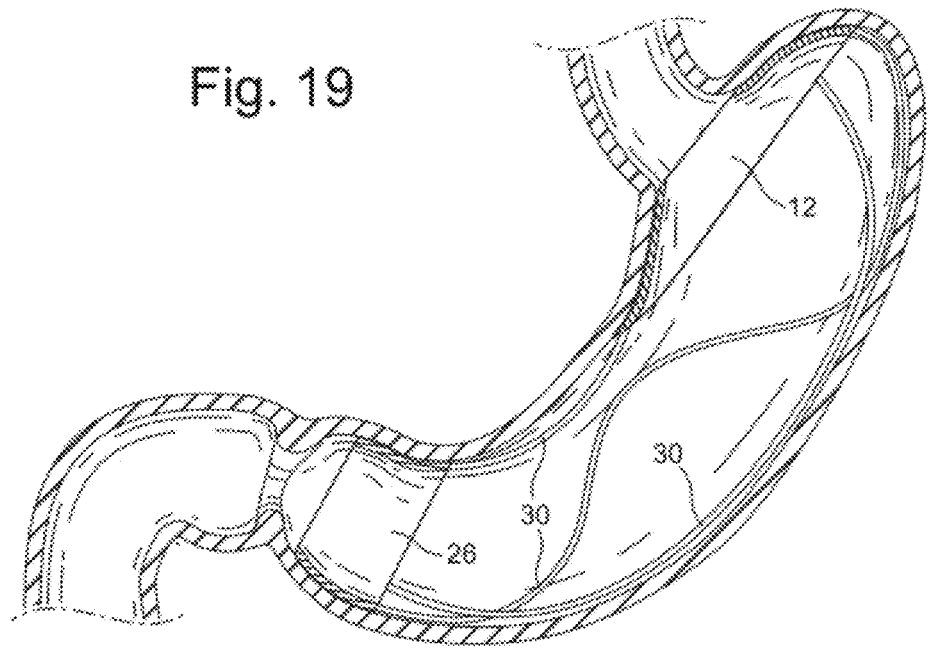
Fig. 19

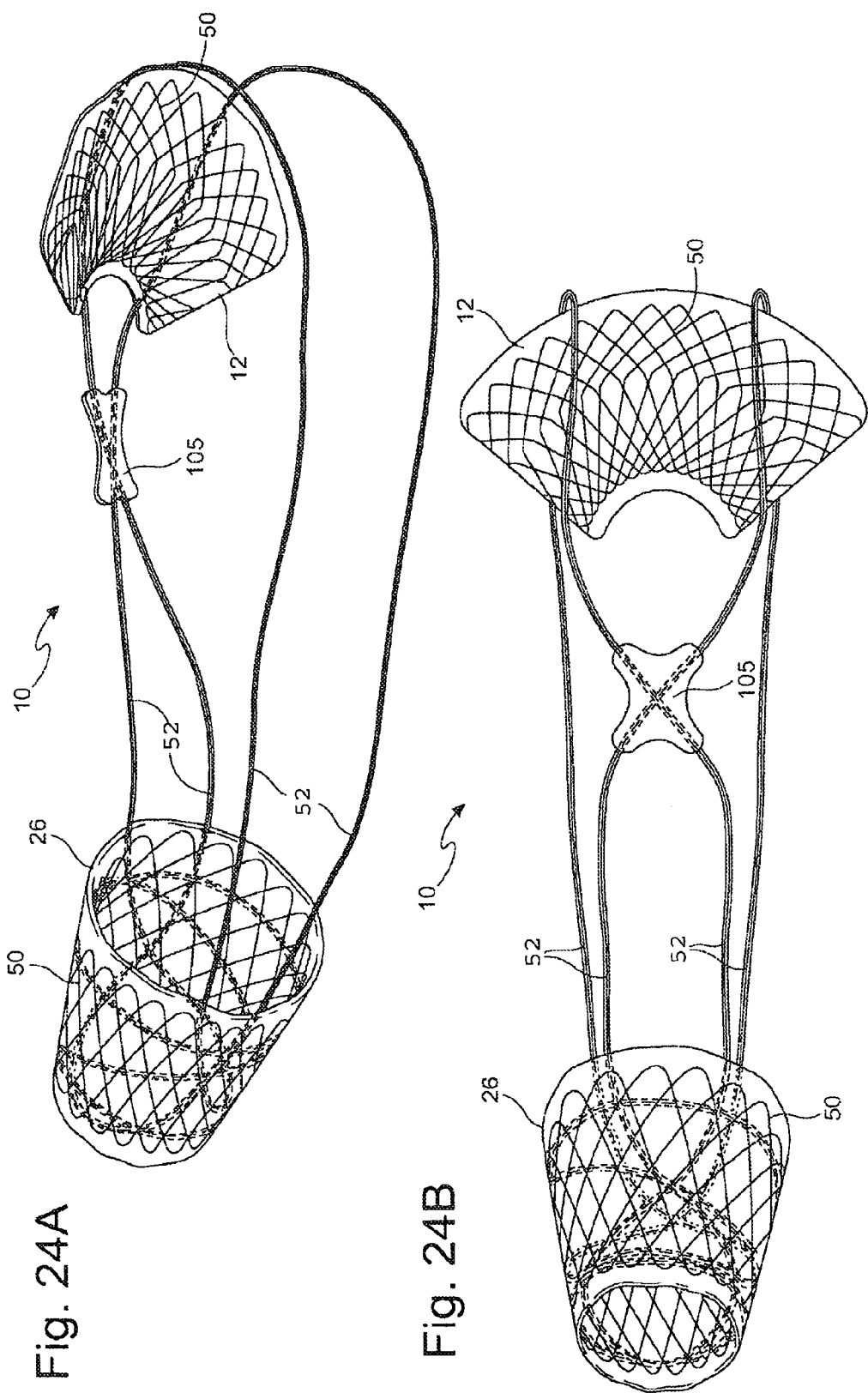

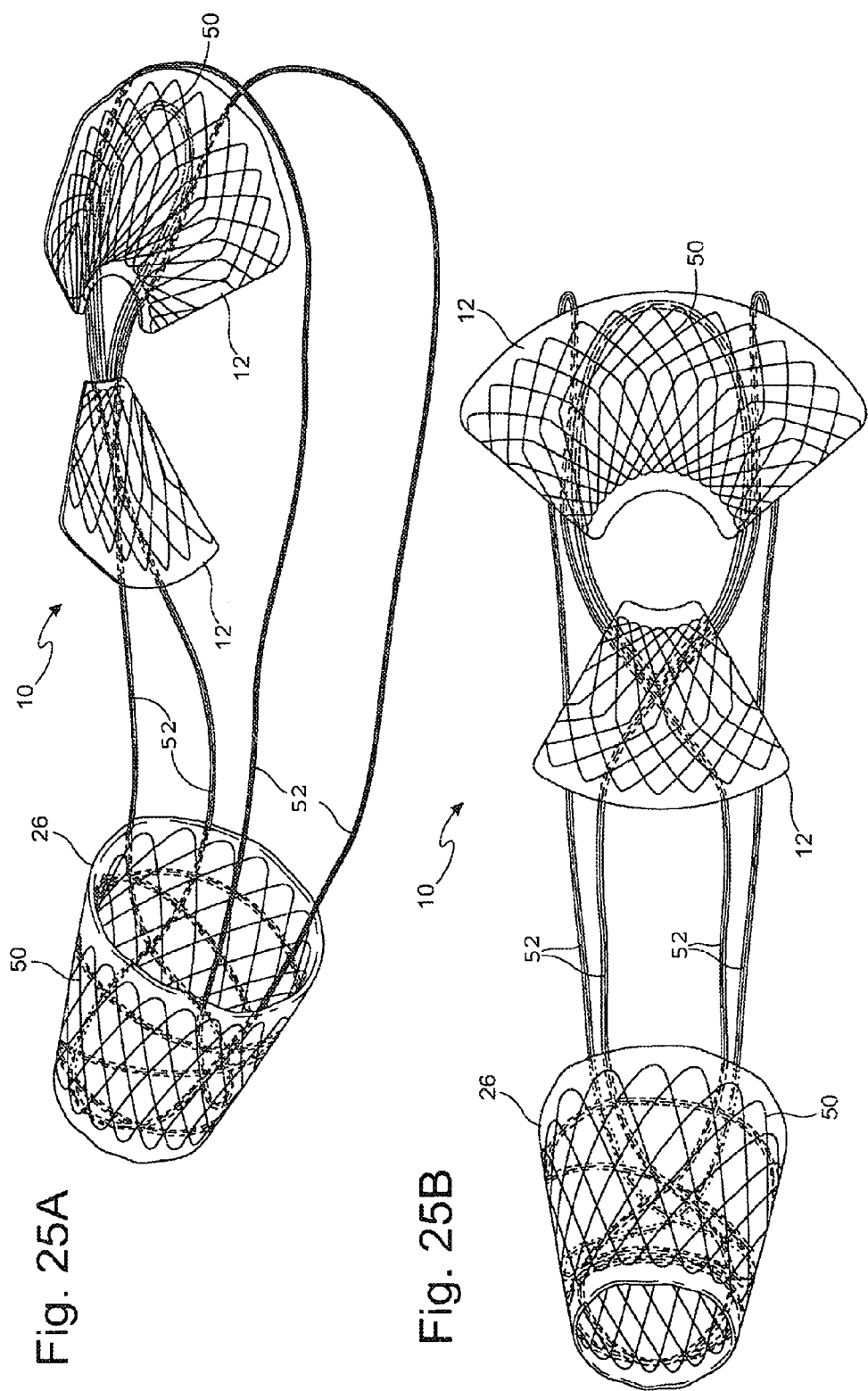

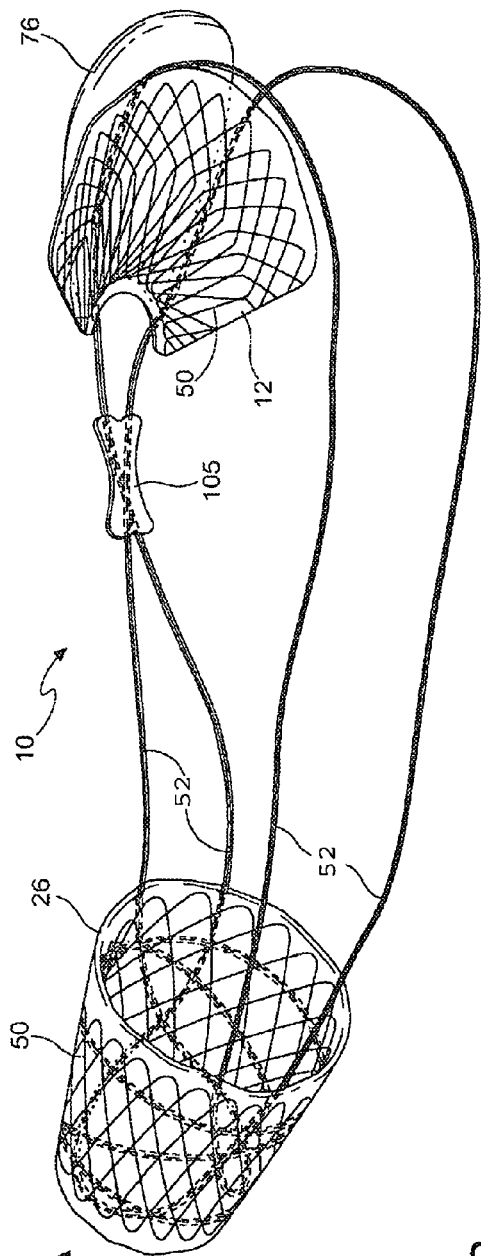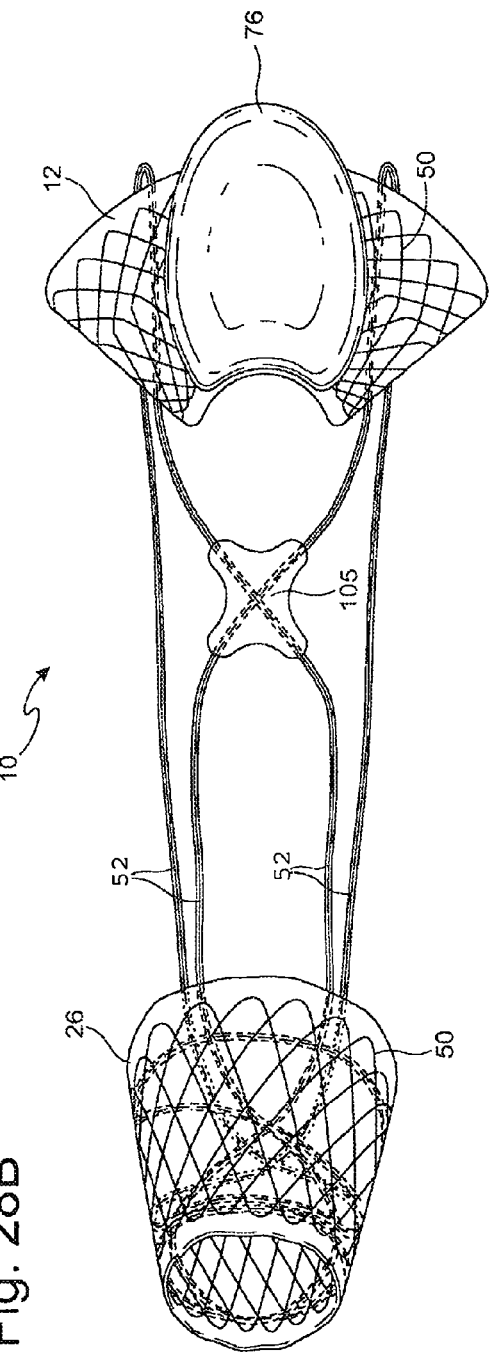

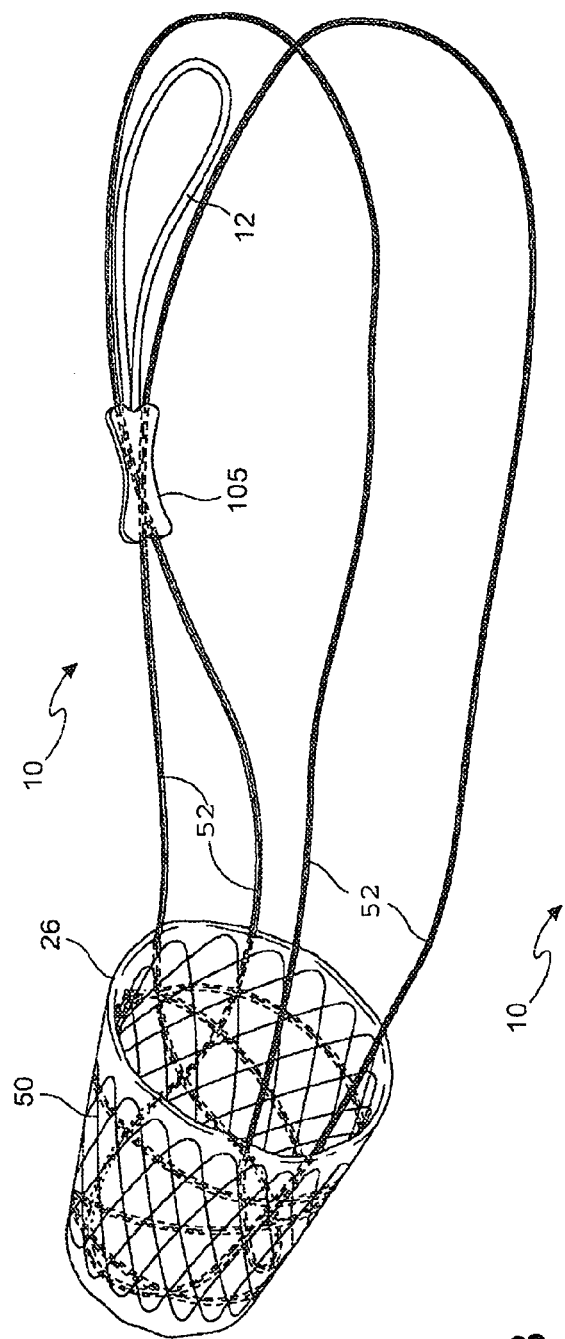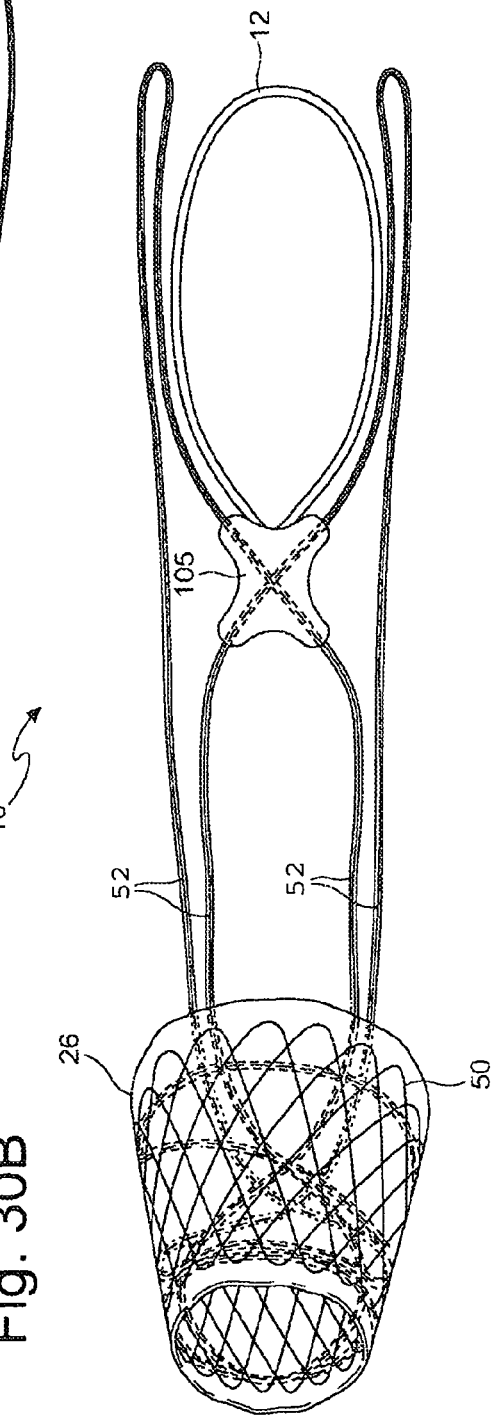

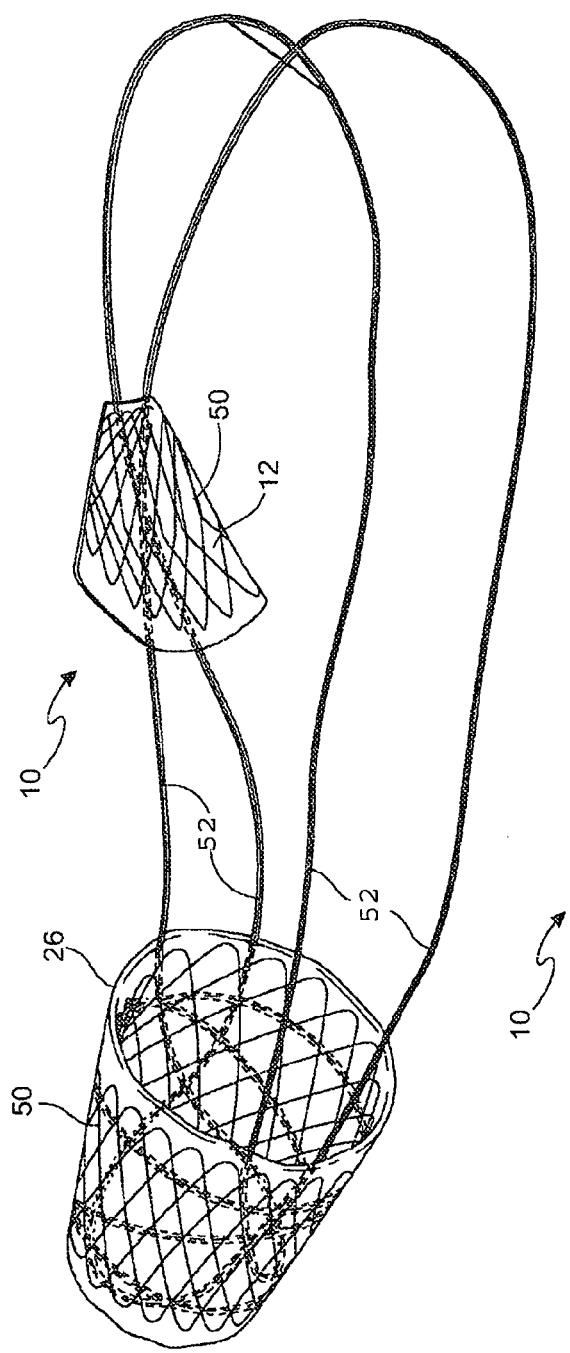
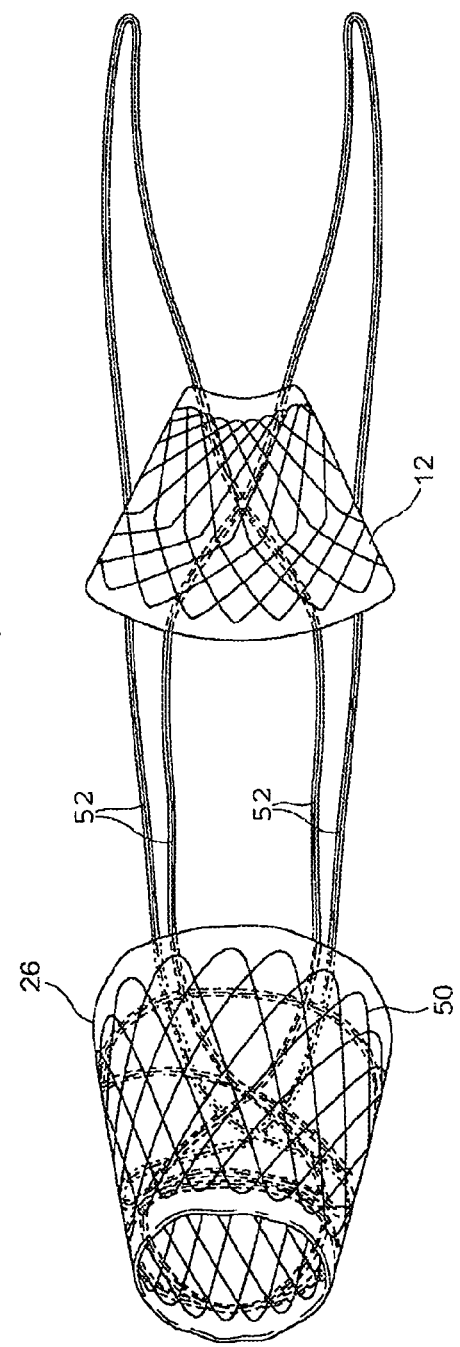
Fig. 33A
Fig. 33B

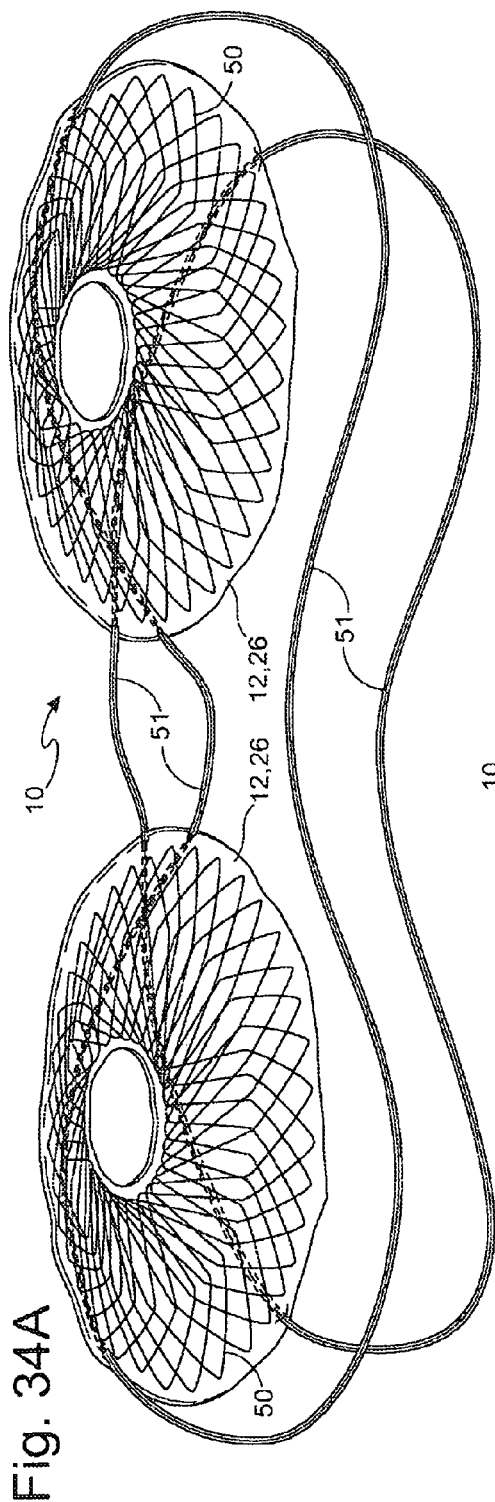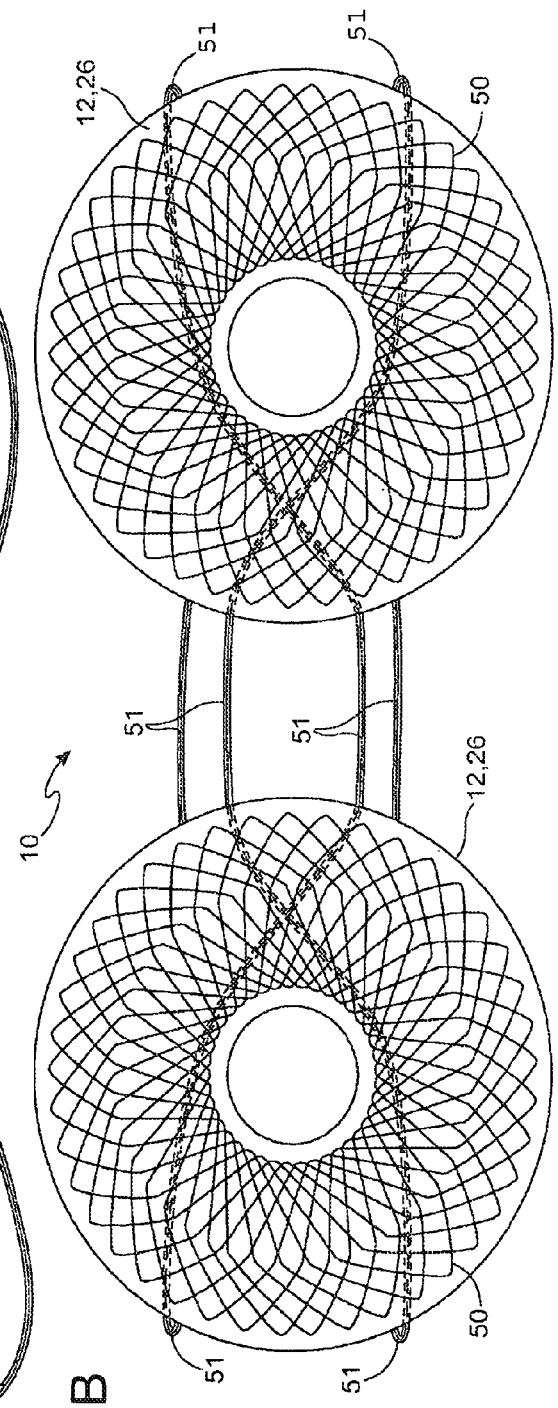

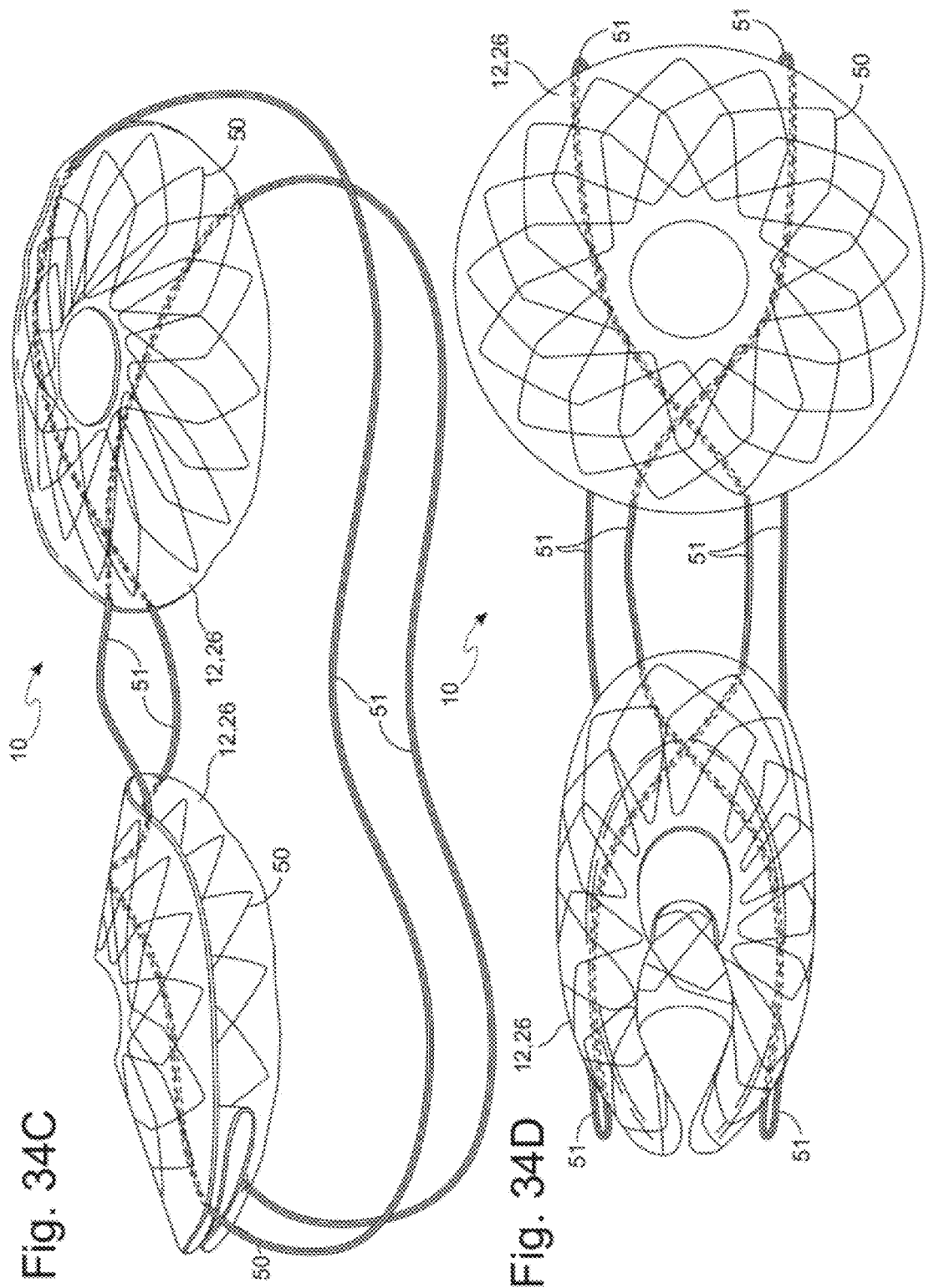

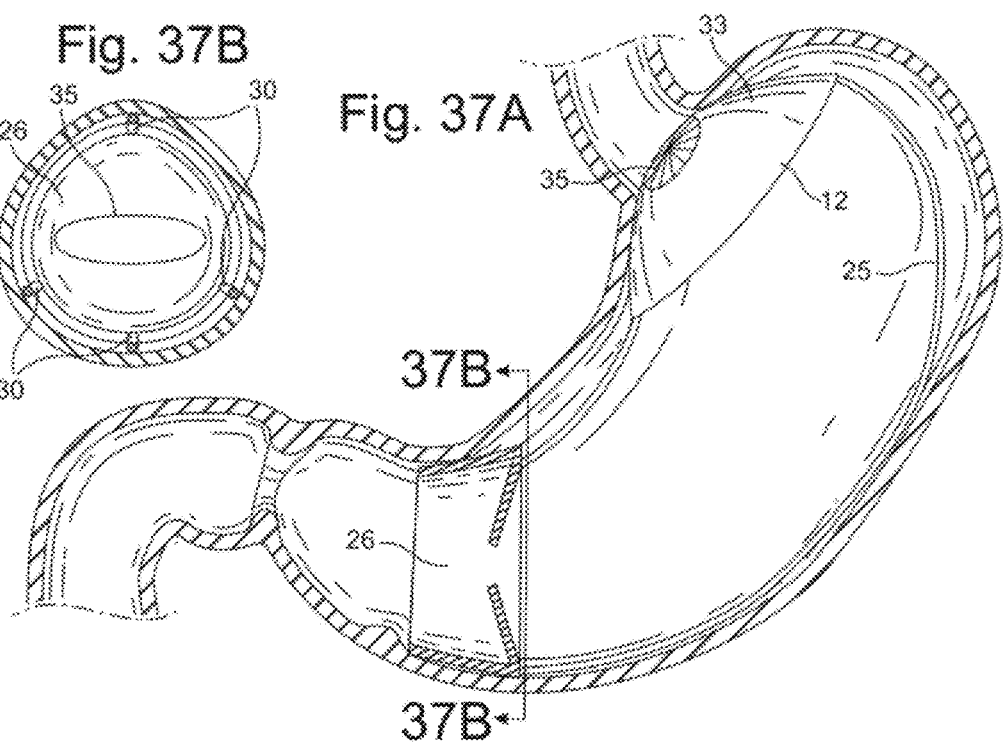
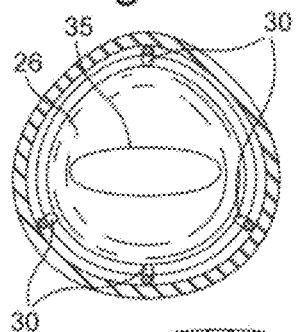
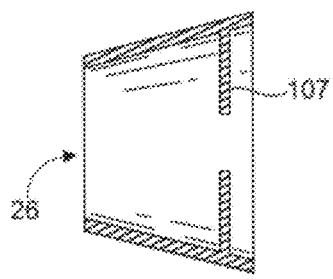
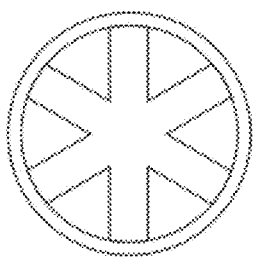
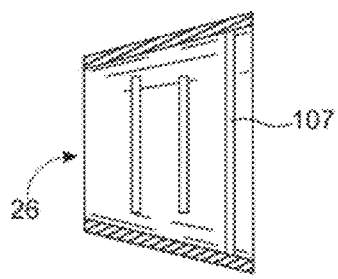
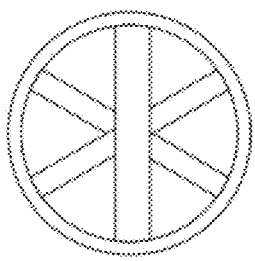

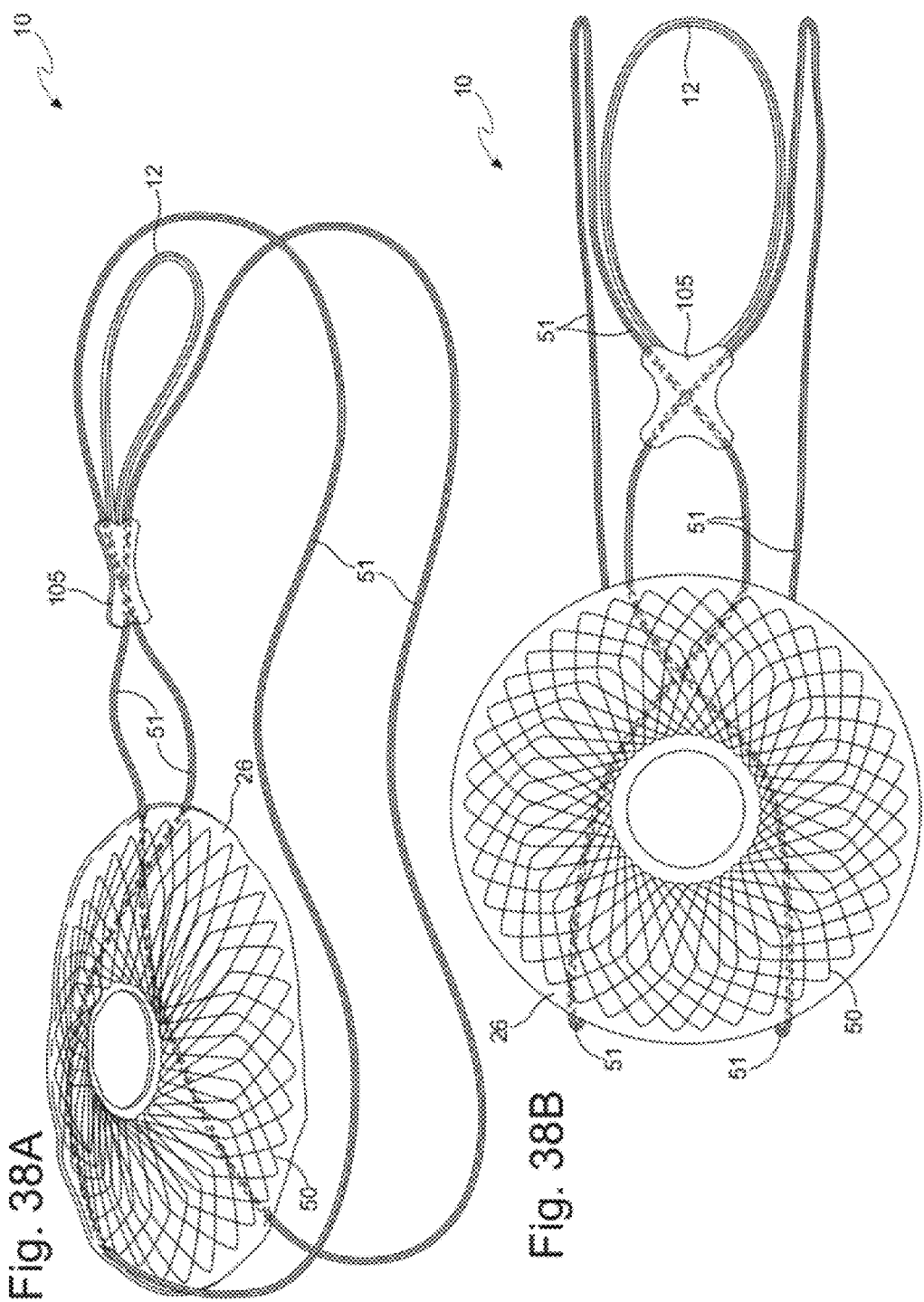

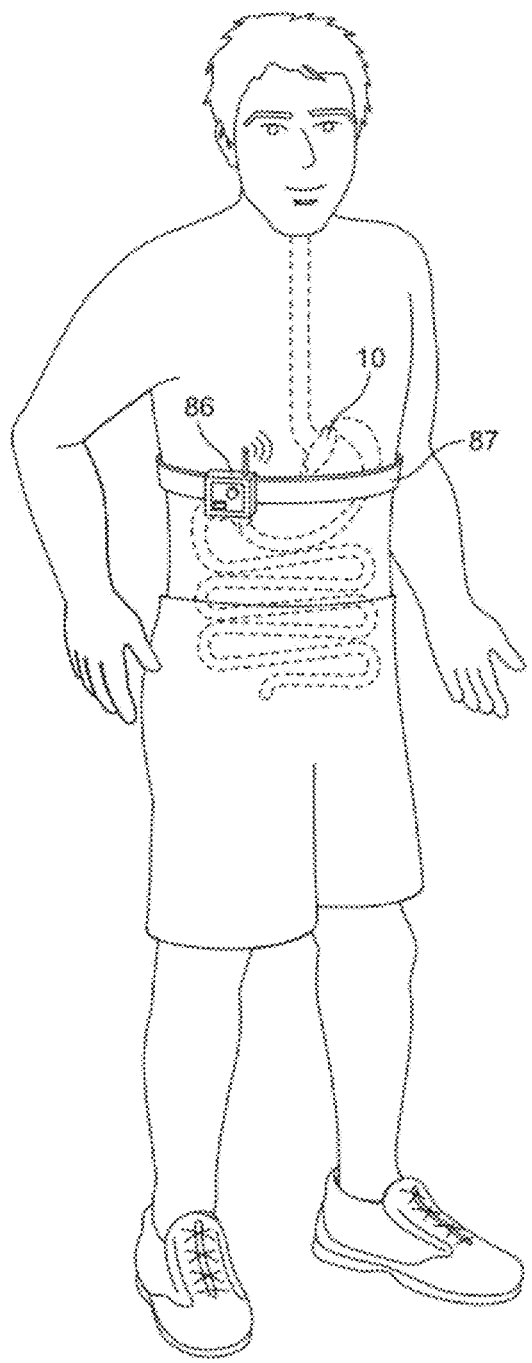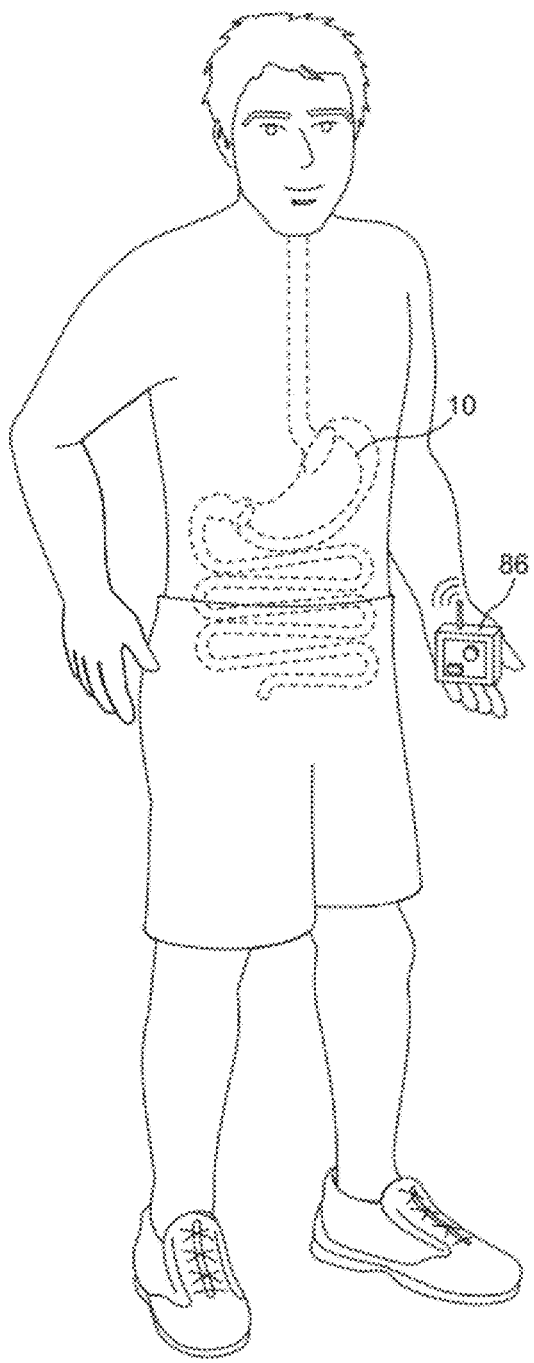

BARIATRIC DEVICE AND METHOD FOR WEIGHT LOSS

RELATED APPLICATION

This application is a national stage application under 35 USC §371 of PCT Patent Application No. PCT/US2010/053619, filed Oct. 21, 2010, which claims the benefit of U.S. Provisional Application No. 61/253,816, filed Oct. 21, 2009, U.S. Provisional Application No. 61/262,040, filed Nov. 17, 2009, U.S. Provisional Application No. 61/262,045, filed Nov. 17, 2009, and U.S. Provisional Application No. 61/264,651, filed Nov. 25, 2009, and PCT Application PCT/US2010/41774, filed Jul. 13, 2010.

TECHNICAL FIELD

This invention relates to a bariatric device for weight loss, and ancillary items such as sizing, deployment, and removal apparatus.

BACKGROUND

Obesity has been steadily increasing worldwide and poses serious health risks, which if untreated, can become life threatening. There are various methods for reducing weight such as diet, exercise, and medications, but often the weight loss is not sustained. Significant advances have been made in the surgical treatment of obesity. Surgical procedures such as the gastric bypass and gastric banding have produced substantial and lasting weight loss for obese patients. These procedures and products have been shown to significantly reduce health risks over time, and are currently the gold standard for bariatric treatment.

Although surgical intervention has been shown to be successful at managing weight loss, both procedures are invasive and carry the risks of surgery. Gastric bypass is a highly invasive procedure which creates a small pouch by segmenting and/or removing a large portion of the stomach and rerouting the intestines permanently. Gastric bypass and its variations have known complications. Gastric banding is an invasive procedure which creates a small pouch in the upper stomach by wrapping a band around the stomach to segment it from the lower stomach. Although the procedure is reversible, it also carries known complications.

Less invasive or non-invasive devices that are removable and capable of significant weight loss are desirable.

SUMMARY

The bariatric device described herein induces weight loss by engaging the upper and lower regions of the stomach. One embodiment of the bariatric device disclosed herein is based on applying force or pressure on or around the cardiac opening or gastroesophogeal (GE) junction and upper stomach and the lower stomach. It may also include pressure in the lower esophagus. The device can be straightened or compressed to allow for introduction down the esophagus and then change into the desired shape inside the stomach. This device may not require any sutures or fixation and would orient inside the stomach based on the device's geometry.

The device may be constructed of three main elements:

1) A cardiac element that engages the upper stomach around the GE junction including the cardiac region and adjacent fundus and may include the lower esophagus.

2) A pyloric element that engages the pyloric region which includes the pyloric antrum or lower stomach.

3) A connecting element that connects the cardiac and pyloric elements.

One of the purposes of the cardiac element which contacts the upper stomach or cardiac region would be to apply at least intermittent pressure or force to engage a satiety response and/or cause a neurohormonal response to cause a reduction in weight. This element could take the form of many different shapes such as a ring, a disk, a cone, frusto-cone, a portion of a cone, portion of frusto-cone, a sphere, an oval, an ovoid, a tear drop, a pyramid, a square, a rectangle, a trapezoid, a wireform, a spiral, multiple protuberances, multiple spheres or multiples of any shape or other suitable shapes. It could also be an inflatable balloon or contain an inflatable balloon. This balloon could be spherical, or it could be a torus or a sphere with channels on the side to allow food to pass, or it could be a cone, a portion of a cone or other shapes. The cardiac element may be in constant or intermittent contact with the upper stomach based on the device moving in the stomach during peristalsis. For the purpose of the claims of this patent, the "upper stomach" includes the cardiac region (a band of tissue in the stomach that surrounds the gastroesophogeal (GE) junction), and the fundus adjacent to the cardiac region, and may be either of these two areas, or both.

Some of the purposes of the pyloric element are to engage the pyloric region or lower stomach, and to act in conjunction with the connecting element to provide support for the cardiac element to apply constant, intermittent, or indirect pressure against the upper stomach and or GE junction and lower esophagus. It is also to prevent the device from migrating into the duodenum or small intestine. This pyloric element would be preferentially above the pyloric valve and could be in constant or intermittent contact with the pyloric region or lower stomach based on movement of the stomach. Depending on the size relative to the stomach, this element may apply radial force, or contact force or pressure to the lower stomach which may also cause a satiety or neurohormonal response. Due to peristalsis of the stomach, the bariatric device may toggle back and forth in the stomach which may cause intermittent contact with the upper and lower stomach regions. The device may also have features to accommodate for the motion to allow for constant contact with the upper and lower regions. Similar to the cardiac element, the pyloric element could take several different shapes such as a ring, a disk, a cone, frusto-cone, a portion of a cone, portion of frusto-cone, a sphere, an oval, an ovoid, a tear drop, a pyramid, a square, a rectangle, a trapezoid, a wireform, a spiral, multiple protuberances, multiple spheres or multiples of any shape or other suitable shapes. It could also be an inflatable balloon. This balloon could be spherical, or it could be a torus or a sphere with channels on the side to allow food to pass, or it could be a cone, a portion of a cone or other shape. This element may activate stretch receptors or a neurohormonal response to induce satiety or another mechanism of weight loss by contacting or stretching certain portions of the stomach, to induce satiety, delay gastric emptying or another mechanism of weight loss. The form and structure of the cardiac and pyloric elements may vary to adapt appropriately for their purpose. For example, the cardiac element may be a ring while the pyloric element may be a cone or frusto-cone or any combination disclosed herein.

Some of the purposes of the connecting element are to connect the cardiac and pyloric elements, to provide structure for the device to maintain its relative placement location, and to provide tension, pressure, or an outwardly biasing force between the pyloric and cardiac elements. The connecting element could take several different forms such as a long curved wire, a curved cylinder of varying diameters, a spiral of a single diameter, a spiral of varying diameter, a ribbon, an I-beam, a tube, a woven structure, a taper, a loop, a curved loop or other. Similarly, the connecting element could comprise multiple members to improve its structural integrity and positioning within the stomach. The connecting element could be generally curved to match the greater curve, lesser curve or midline of the stomach, could be straight, or a combination of any of the above. The connecting element could also be an inflatable balloon or incorporate an inflatable balloon.

The connecting element could also be self expanding or incorporate a portion that is self expanding. Self expansion would allow the element or a portion of the element to be compressible, but also allow it to expand back into its original shape to maintain its function and position within the stomach, as well as the function and position of the other element(s). Self expansion would allow the elements to compress for placement down the esophagus, and then expand its original shape in the stomach. This will also allow the element to accommodate peristalsis once the device is in the stomach. This self-expansion construction of the connecting element may impart an outwardly biasing force on the cardiac element, the pyloric element, or both.

In any of the embodiments disclosed herein, the device may be straightened or collapsed for insertion down the esophagus, and then reformed to the desired shape in the stomach to apply pressure at the upper and lower stomach regions or other regions as described above. At least a portion of the device could be made of a shape memory alloys such as Nitinol (nickel titanium), low density polyethylene or polymers to allow for it to compress or flex and then rebound into shape in the stomach. For placement of the device into the stomach, a flexible polymer tube, such as a large diameter overtube or orogastric tube, could be placed down the esophagus to protect the esophagus and stomach. The device could then be straightened and placed into the tube for delivery into the stomach, and then would regain its proper shape in the stomach once it exits the tube. Another variation for placement would be a custom delivery catheter to compress the device during placement and then allow the device to deploy out of the catheter once in the stomach.

The bariatric device could be made of many different materials. Elements of the device could be made with materials with spring properties that have adequate strength to hold their shape after reforming, and/or impart an outwardly biasing force. The materials would also need to be acid resistant to withstand the acidic environment of the stomach. Elements of the device could be made of Nitinol, shape memory plastics, shape memory gels, stainless steel, super alloys, titanium, silicone, elastomers, teflons, polyurethanes, polynorborenes, styrene butadiene co-polymers, cross-linked polyethylenes, cross-linked polycyclooctenes, polyethers, polyacrylates, polyamides, polysiloxanes, polyether amides, polyether esters, and urethane-butadiene co-polymers, other polymers, or combinations of the above, or other suitable materials. For good distribution of stress to the stomach wall or to reduce contact friction, the device could be coated with another material or could be placed into a sleeve of acid resistant materials such as teflons, PTFE, ePTFE, FEP, silicone, elastomers or other polymers. This would allow for a small wire to be cased in a thicker sleeve of acid resistant materials to allow for a better distribution of force across a larger surface area.

The device could take many forms after it reshapes.

BRIEF DESCRIPTION OF DRAWINGS

FIG. 12 depicts a side cross-section view of an embodiment of the bariatric device with an inflatable balloon, located within a cross-section of a stomach

FIG. 16A depicts a side view of an embodiment of the bariatric device of the present invention, located within a cross-section of a stomach.

FIG. 16B depicts an internal end view of a pyloric element of an embodiment of the bariatric device of the present invention, located within a cross-section of a stomach shown in FIG. 16A.

FIG. 17A depicts a side view of an embodiment of the bariatric device of the present invention, located within a cross-section of a stomach.

FIG. 17B depicts an internal end view of a pyloric element of an embodiment of the bariatric device of the present invention, located within a cross-section of a stomach shown in FIG. 17A.

FIG. 18A depicts a side view of an embodiment of the bariatric device of the present invention, located within a cross-section of a stomach.

FIG. 18B depicts an internal end view of a pyloric element of an embodiment of the bariatric device of the present invention, located within a cross-section of a stomach shown in FIG. 18A.

FIG. 19 depicts a side view of the embodiment of the present invention shown in FIG. 18A, located within a cross-section of a stomach that is undergoing contraction due to peristalsis.

FIG. 24A depicts an underside perspective view of an embodiment of the bariatric device of the present invention.

FIG. 24B depicts a front view of an embodiment of the bariatric device of the present invention.

FIG. 25A depicts an underside perspective view of an embodiment of the bariatric device of the present invention.

FIG. 25B depicts a front view of an embodiment of the bariatric device of the present invention.

FIG. 28A depicts an underside perspective view of an embodiment of the bariatric device of the present invention, having an adjustment mechanism in the cardiac element in an inflated state.

FIG. 28B depicts a front view of an embodiment of the bariatric device of the present invention, having an adjustment mechanism in the cardiac element in an inflated state.

FIG. 30A depicts an underside perspective view of an embodiment of the bariatric device of the present invention.

FIG. 30B depicts a front view of an embodiment of the bariatric device of the present invention.

FIG. 33A depicts an underside perspective view of an embodiment of the bariatric device of the present invention.

FIG. 33B depicts a front view of an embodiment of the bariatric device of the present invention.

FIG. 34A depicts an underside perspective view of an embodiment of the bariatric device of the present invention.

FIG. 34B depicts a front view of an embodiment of the bariatric device of the present invention.

FIG. 34C depicts an underside perspective view of an embodiment of the bariatric device of the present invention with one of the elements in a folded state.

FIG. 34D depicts a front view of an embodiment of the bariatric device of the present invention with one of the elements in a folded state.

FIG. 37A depicts a side view of an embodiment of the bariatric device of the present embodiment, located within a cross-section of a stomach.

FIG. 37B depicts an internal end view of the pyloric element of the embodiment shown in FIG. 37A., located within a cross-section of a stomach shown in FIG. 37A.

FIG. 37C depicts a side cross-section view of another embodiment for the pyloric element of FIG. 37A.

FIG. 37D depicts an end view of the pyloric element of the embodiment shown in FIG. 37C.

FIG. 37E depicts a side cross-section view of another embodiment for the pyloric element of FIG. 37A.

FIG. 37F depicts an end view of the pyloric element of the embodiment shown in FIG. 37E.

FIG. 38A depicts an underside perspective view of an embodiment of the bariatric device of the present invention.

FIG. 38B depicts a front view of an embodiment of the bariatric device of the present invention.

FIG. 44 depicts a remote controller of an embodiment of the present invention, worn next to the user's body.

FIG. 45 depicts a remote controller of an embodiment of the present invention, used without wearing or placing adjacent to the body.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
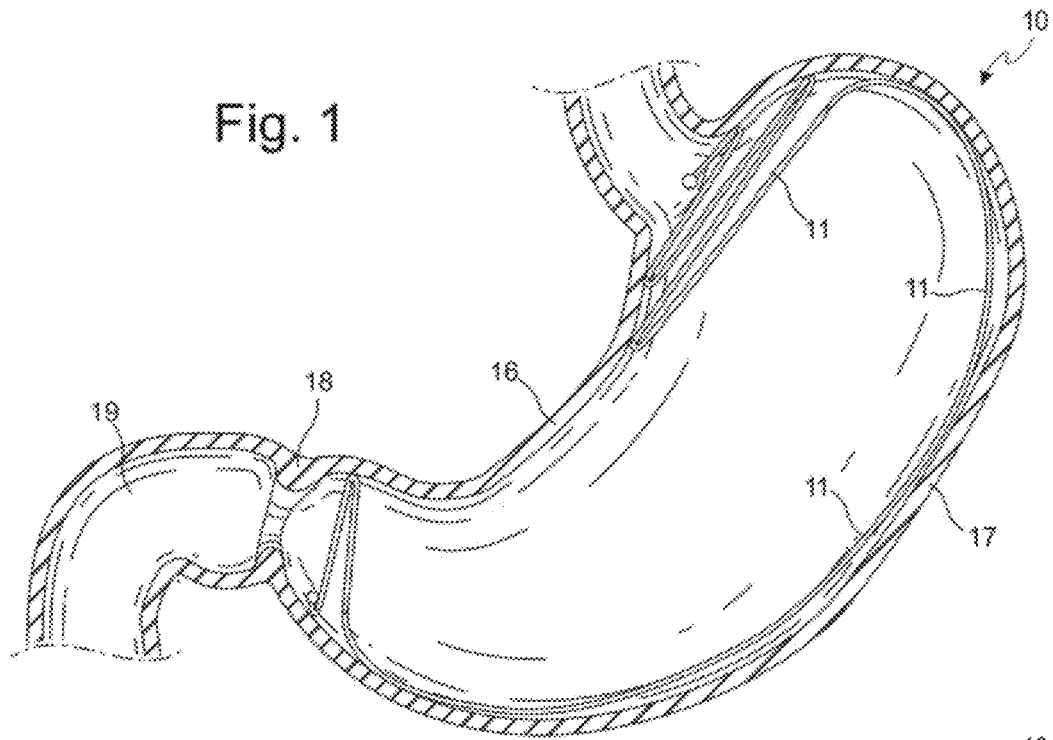
FIG. 1 depicts a side view of a single wire embodiment the bariatric device of the present invention located within a cross-section of a stomach.
Figure 2:
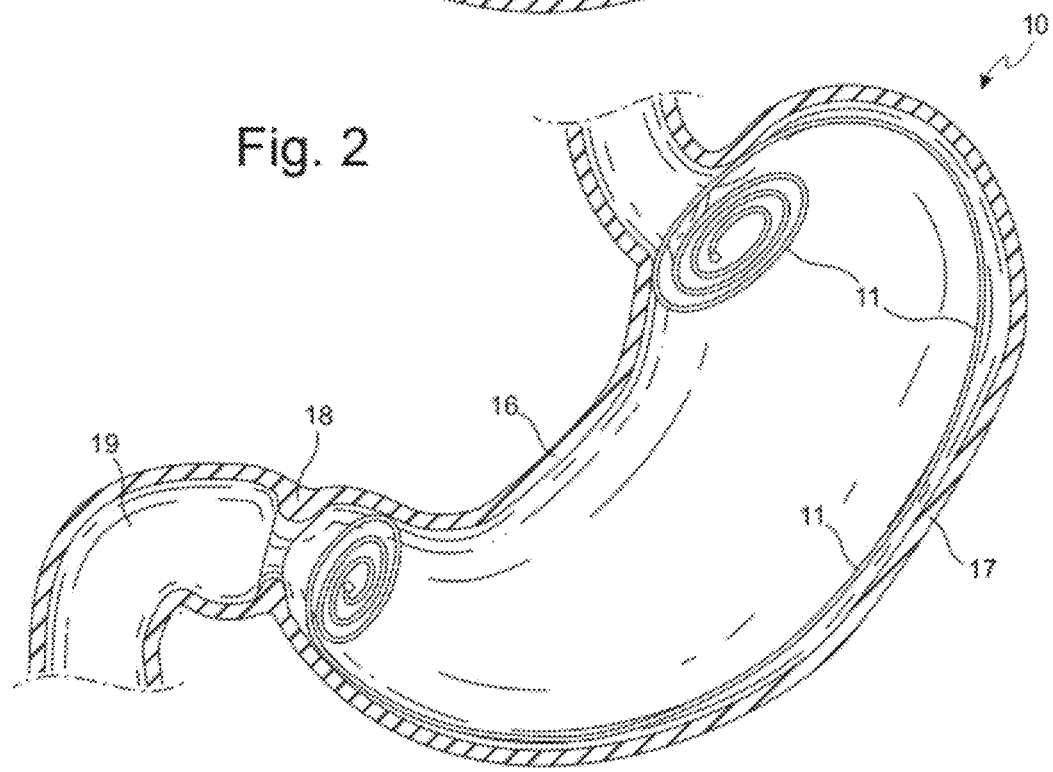
FIG. 2 depicts a side view of an alternative single wire embodiment the bariatric device of the present invention located within a cross-section of a stomach.

The most basic embodiment of the bariatric device 10 may have a single piece of Nitinol wire 11 which is shape set into a shape, but can be pulled under tension into a generally narrow and straight form, to allow for insertion of the device 10 through the esophagus. In such an embodiment, the elements may all be seamlessly integrated as one wire structure. See FIGS. 1 and 2. Depending on the size of the stomach, the shape set wire may impart an outwardly biasing force to the proximal and distal elements of the bariatric device 10, which may vary during peristalsis.

In any of the embodiments discussed herein, the connecting elements 25 may be constructed of materials, or in such a manner, that may impart an outwardly biasing force, to push on the cardiac and/or pyloric elements. Such outwardly biasing force may impart constant or intermittent pressure to various parts of the stomach, through the cardiac element 12, the pyloric element 26, the connecting elements 25, or any combination thereof.

Figure 4:
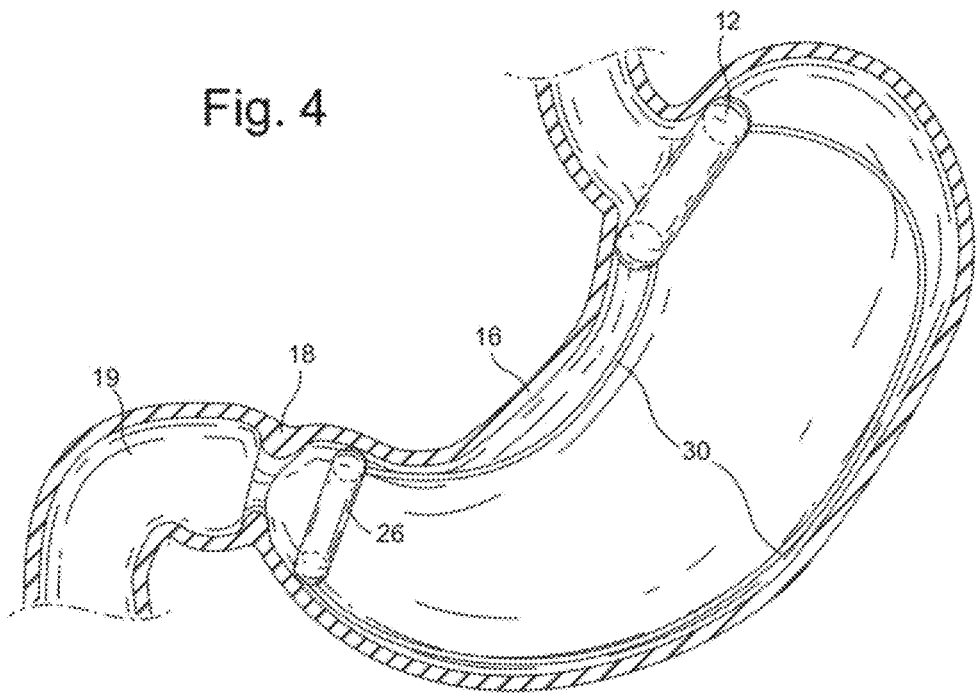
FIG. 4 depicts a side view of an embodiment of the bariatric device of the present invention, located within a cross-section of a stomach.
Figure 5:
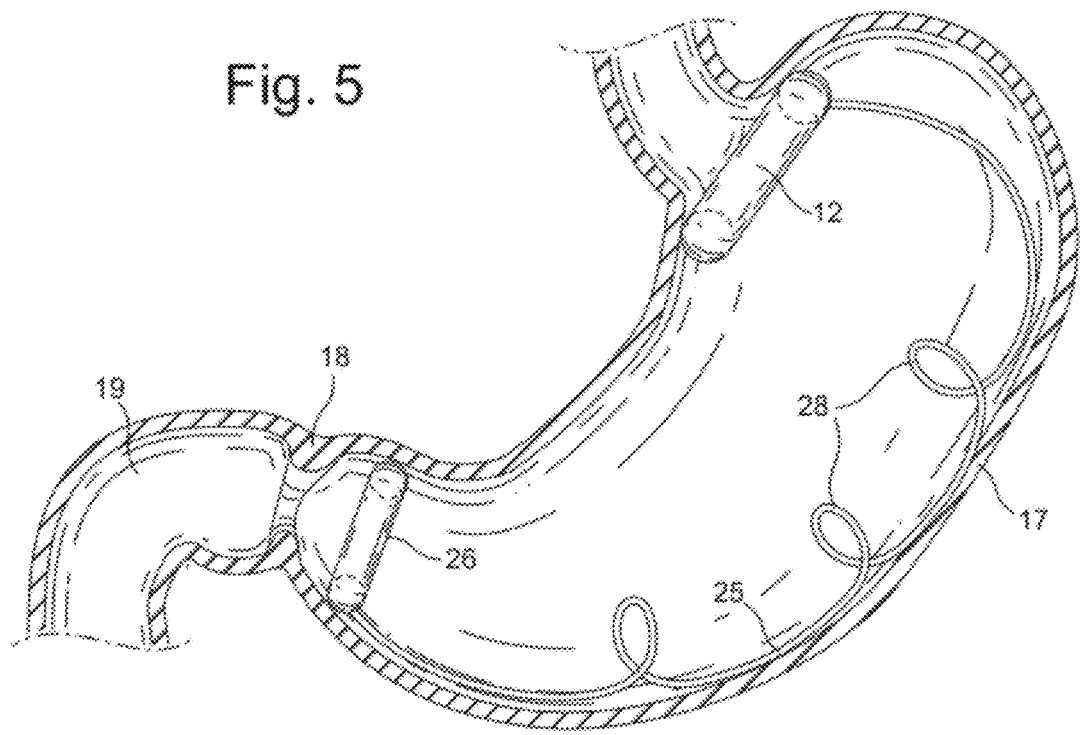
FIG. 5 depicts a side view of an embodiment of the bariatric device of the present invention, located within a cross-section of a stomach.

In the three-element embodiment (cardiac, pyloric, and connecting elements 12, 26, 25), the three elements may all be seamlessly integrated as one wire structure. When tension to flex, compress or stretch the device 10 is released, it may coil into a ring or loop near the cardia 40, and coil into a ring or loop near the pyloric region 42, with a curved member to connect the two elements that is shaped to relatively match the greater curve 17 of the stomach. The curve could also match the lesser curve 16 of the stomach or both. See FIGS. 3 and 4. The connecting element 25 could curve into a single ring, or it could curve into a spiral. See FIG. 5.

Figure 6:
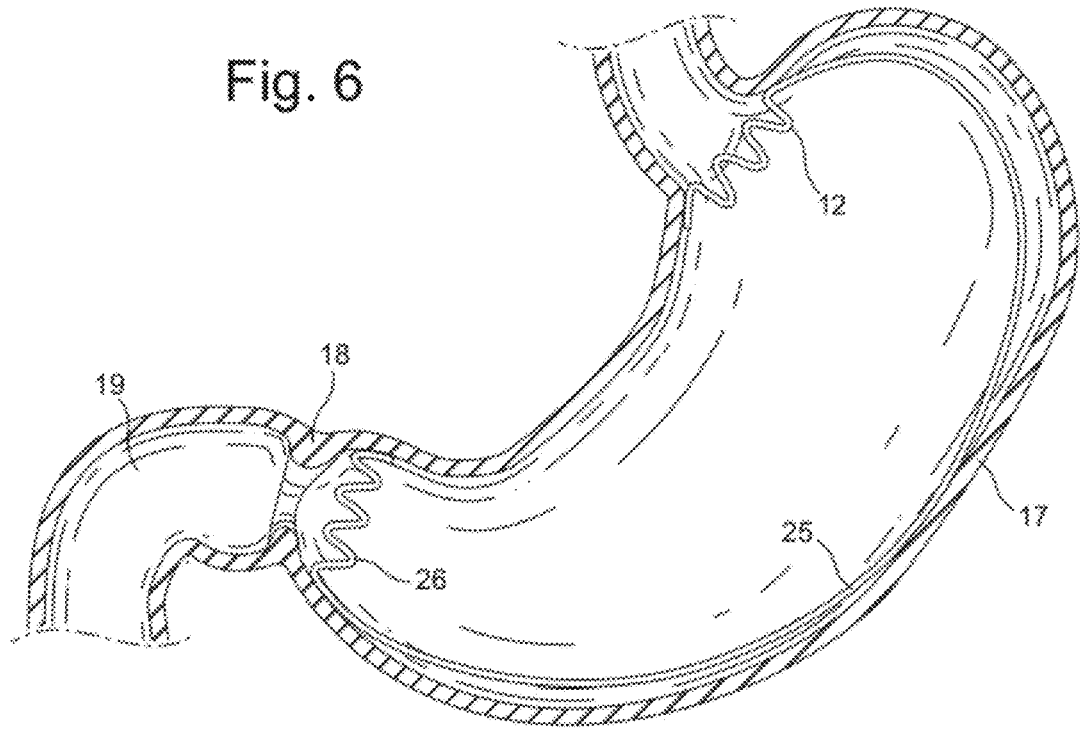
FIG. 6 depicts a side view of an embodiment of the bariatric device of the present invention, located within a cross-section of a stomach.
Figure 7:
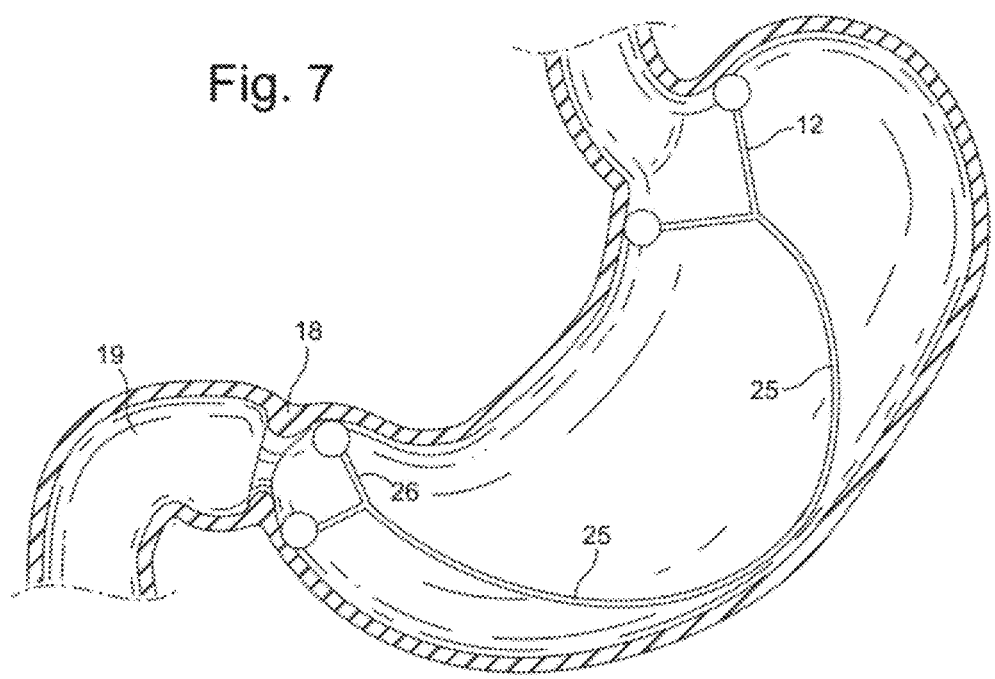
FIG. 7 depicts a side view of an embodiment of the bariatric device of the present invention, located within a cross-section of a stomach.

As in other embodiments, the rings at each end could lock or not lock after forming, the rings may be closed, locked or continuous prior to placement down the esophagus, and could be compressed enough to fit within a placement tube for placement through the esophagus. See FIGS. 3 and 4. As with other embodiments, the elements of the bariatric device 10 may have a variety of shapes to add pressure points that continuously move to stimulate the cardiac region 40 during peristalsis. See FIGS. 6, 7, and 8. The device 10 need not be fixed into place but may be moveable, and generally self-seating. The device 10 may have a bias to fit the nonsymmetrical stomach shape and ensure that it seats into the cardiac region 40 and pyloric region 42. Similarly, the action of peristalsis could create additional satiety signals as the device 10 moved in the stomach varying the pressure placed on the cardiac region 40 and/or the pyloric region 42 over time.

Figure 3:
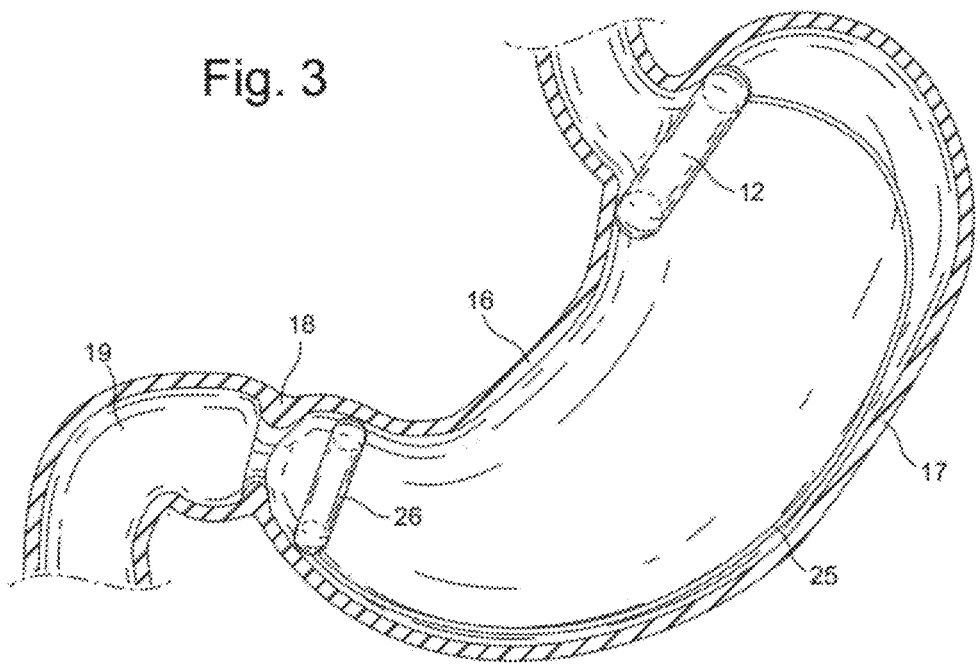
FIG. 3 depicts a side view of an embodiment of the bariatric device of the present invention located within a cross-section of a stomach.
Figure 9:
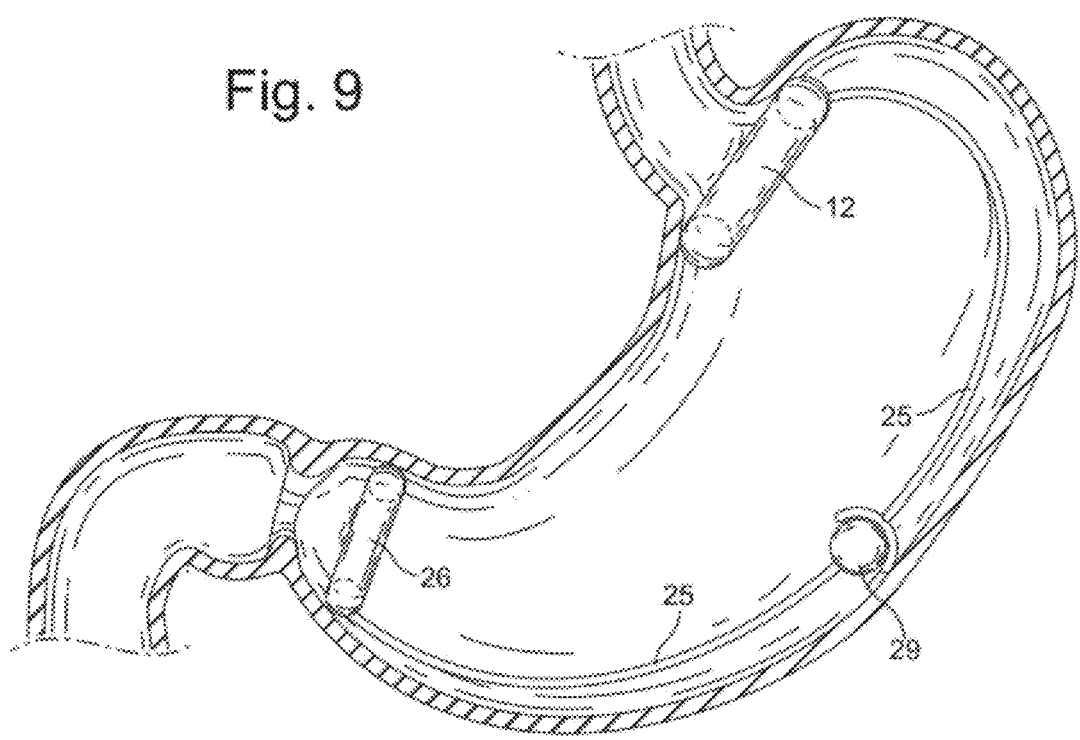
FIG. 9 depicts a side view of an embodiment of the bariatric device of the present invention, located within a cross-section of a stomach.

In the three-element design shown in FIG. 3, the connecting element 25 connecting the two rings could follow the natural curve of the stomach to match the greater or lesser curve of the stomach 17, 16, or could have both. This would aid in the seating of the device 10 in the stomach after placement. The connecting element 25 could have one or more connecting members 30 connecting the cardiac and pyloric elements 12, 26. See FIG. 4. However, these members 30 should be flexible enough to allow for natural peristalsis to occur, natural sphincter function to occur and to not cause erosion or irritation of the stomach wall or significant migration into the esophagus or duodenum 19. There could also be struts or supports that help to support the geometric shape of the rings to the connecting element 25. The connecting element 25 could also be a spiral 28 or multiple spirals to create a flexible structure. See FIG. 5. The connecting element 25 could also be bisected into two members that stack, telescope or articulate. The connecting element 25 could also have a joint such as a ball and socket type joint 29 or may be connected by magnets. See FIG. 9.

Figure 10:
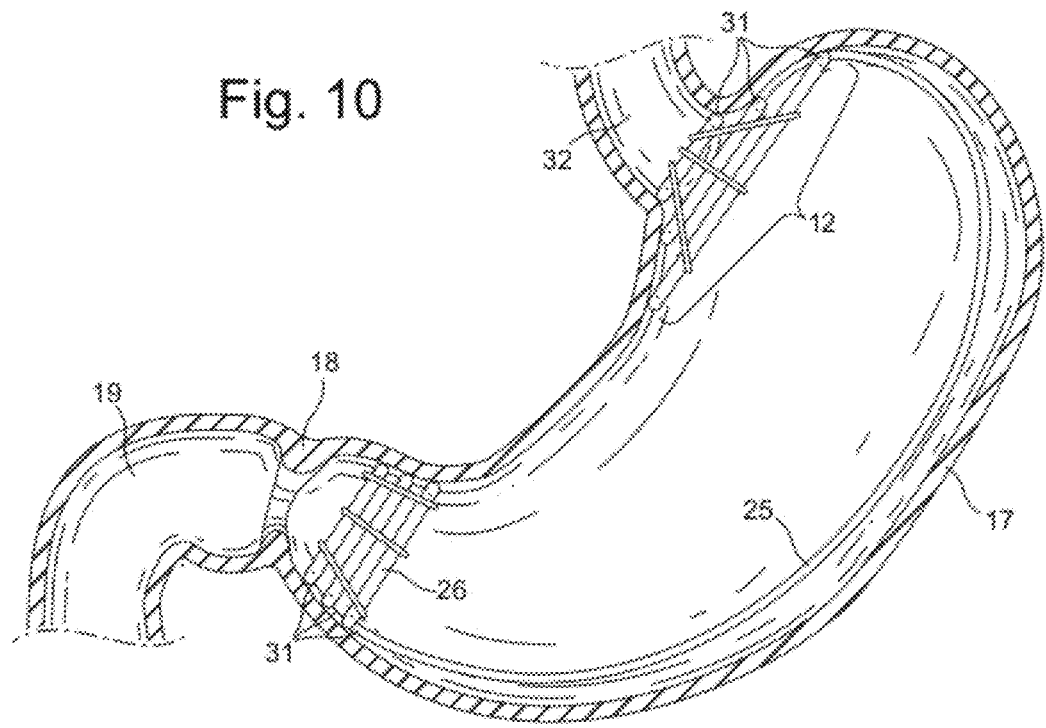
FIG. 10 depicts a side view of an embodiment of the bariatric device of the present invention, located within a cross-section of a stomach.

In another variation of the embodiments, there could be several rings 31 at each end of the device 10 to create an area of pressure at the upper stomach or cardia 40. See FIG. 10. The rings 31 should be sized appropriately to ensure that they do not protrude or slip into the esophagus 32 or into the duodenum 19, unless a variation of this embodiment is designed to have some portion of the device 10 enter those regions. This will allow the device 10 to apply pressure to the upper stomach or cardia 40 without fixation or sutures. The force against the pyloric region 42 and/or lower stomach will provide the counterforce against the upper stomach or cardia 40. At the same time, the force or contact against the pyloric region 42 and/or lower stomach may signal the body to stop eating. This force would mimic having a meal in the stomach with subsequent peristalsis, and sending the signal to stop eating. The multiple rings 31 could take the form of a spiral or could be separate rings 31 connected together. After reforming in the stomach, the rings 31 could lock, not lock, or be continuous. There are several ways that these elements could lock to form a ring.

Figure 11:
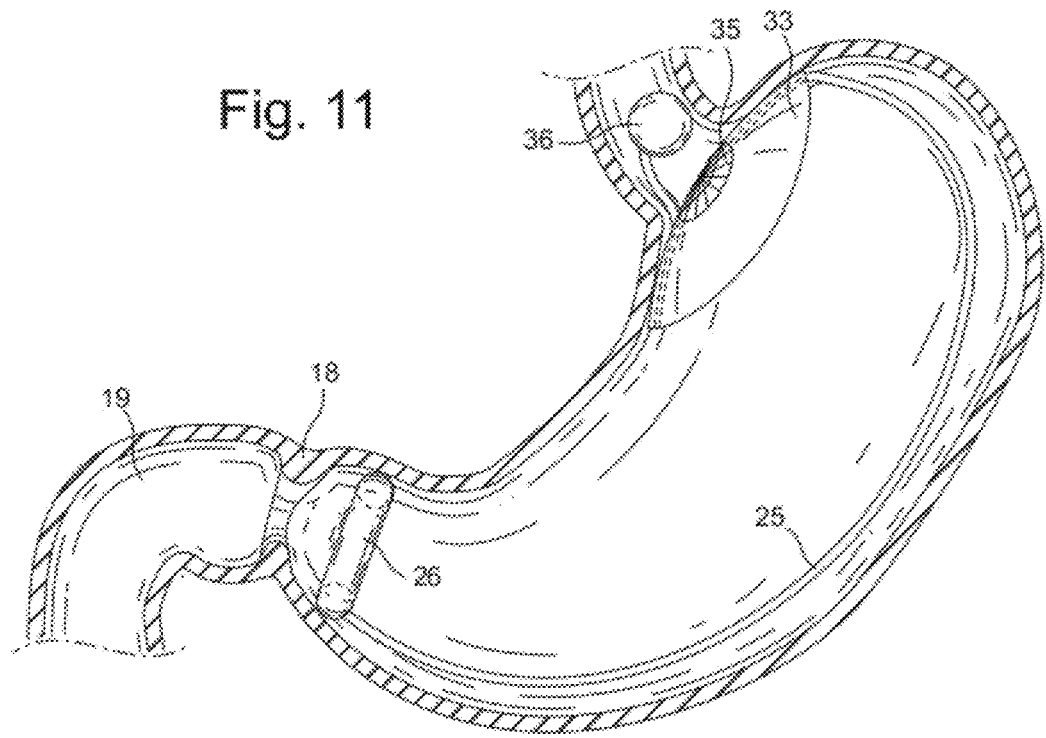
FIG. 11 depicts a side view of an embodiment of the bariatric device of the present invention, located within a cross-section of a stomach.

Another option for the cardiac element 12 would be to have a surface that contacts the upper stomach or cardia 40 such as a hemispherical or conical shaped shell 33 or balloon. The shape could also be asymmetrical but similar to a cone or hemisphere. This could be a thin walled element and could contain a lumen, no lumen, or a valve through which food could pass. FIG. 11 shows a valve 35 created by punching multiple crossing slits in an angular pattern through a thin walled membrane. In the case where there is no opening, the food would have to pass over the hemisphere or cone 33 which would have adequate flexibility to allow the food to pass into the stomach. These restriction elements may require the esophagus 32 to work harder to pass the food over the element and could better stimulate the stretch receptors in the stomach and indirectly in the esophagus. In another alternative, the hemispherical shell 33 could have multiple grooves or channels to aid in allowing food to pass. In the case where there is a lumen in the cardiac element 12, it could be open or it could have a valve 35 that requires some force to allow food to pass through. An option could also be to have an esophageal member 36 that extends into the esophagus 32 for additional esophageal stimulation. This esophageal member 36 could be tethered by a thin structural member to support the esophageal member 36, but not prevent the esophageal sphincter from closing. As mentioned above, this may require the esophagus 32 to work harder to pass the food and may better stimulate the stretch receptors in the stomach and indirectly in the esophagus. This esophageal member 36 could be a large tube, a small tube, a ring, a small sphere, multiple small spheres, or other suitable shapes.

The pyloric element 26 could contain a restriction element, such as a lumen or a valve similar to the valve 35 shown in FIG. 11 for the cardiac element 12. This restriction element could reduce the speed of food passing through the pyloric element 26 if desired. This valve 35 could be a thin membrane of silicone with a single or multiple slits punch through the center, or other types of valves could be used. See FIG. 12. The membrane could also be the shape of funnel with a slit or circular opening, and made from elastomeric material to allow the funnel to expand open as food passes through. This drawing shows a pyloric element 26 with a valve 35 passing across the midsection of the pyloric element to slow down the passage of food. This drawing also describes a connecting element that could be comprised of an inflatable balloon 104. This inflatable body could be compressed for placement and then inflated with a fluid or expandable foam or both to provide structure and adjustability after placement in the stomach. There is an inflation element 74 attached to the balloon where an instrument could be used to add or remove fluid to the inflatable balloon.

Figure 14:
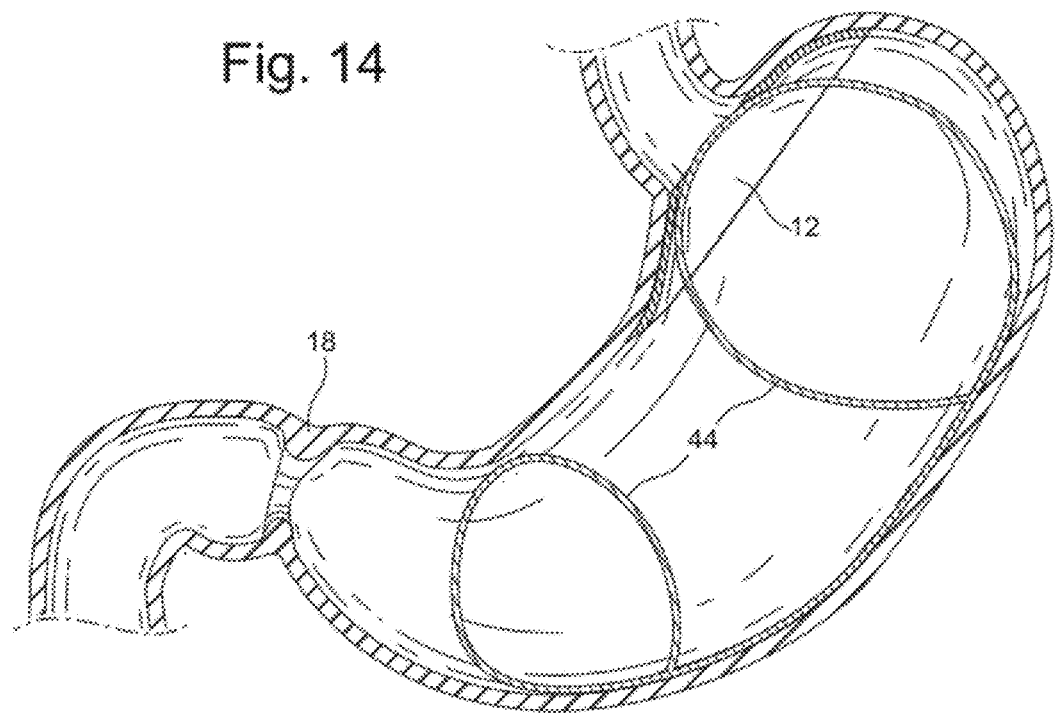
FIG. 14 depicts a side view of an embodiment of the bariatric device of the present invention, located within a cross-section of a stomach.
Figure 15:
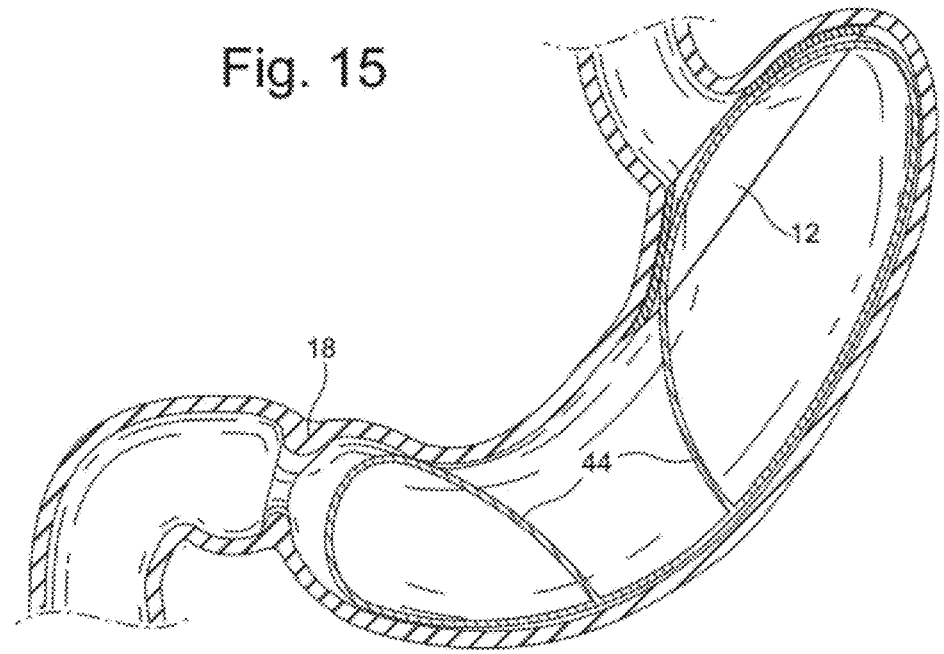
FIG. 15 depicts a side view of the embodiment of the present invention shown in FIG. 14, located within a cross-section of a stomach that is undergoing contraction due to peristalsis.

Another alternative embodiment for the pyloric element 26 would be to change the orientation to allow the axis of the loop or ring in FIG. 11 to be perpendicular to the axis of the pyloric valve 18 as shown in FIGS. 14 and 15. This may simplify manufacturing construction yet perform the same function. In such an embodiment, the pyloric element 26 could have the loop in a single plane, two crossed planes, or multiple planes.

Figure 13A:
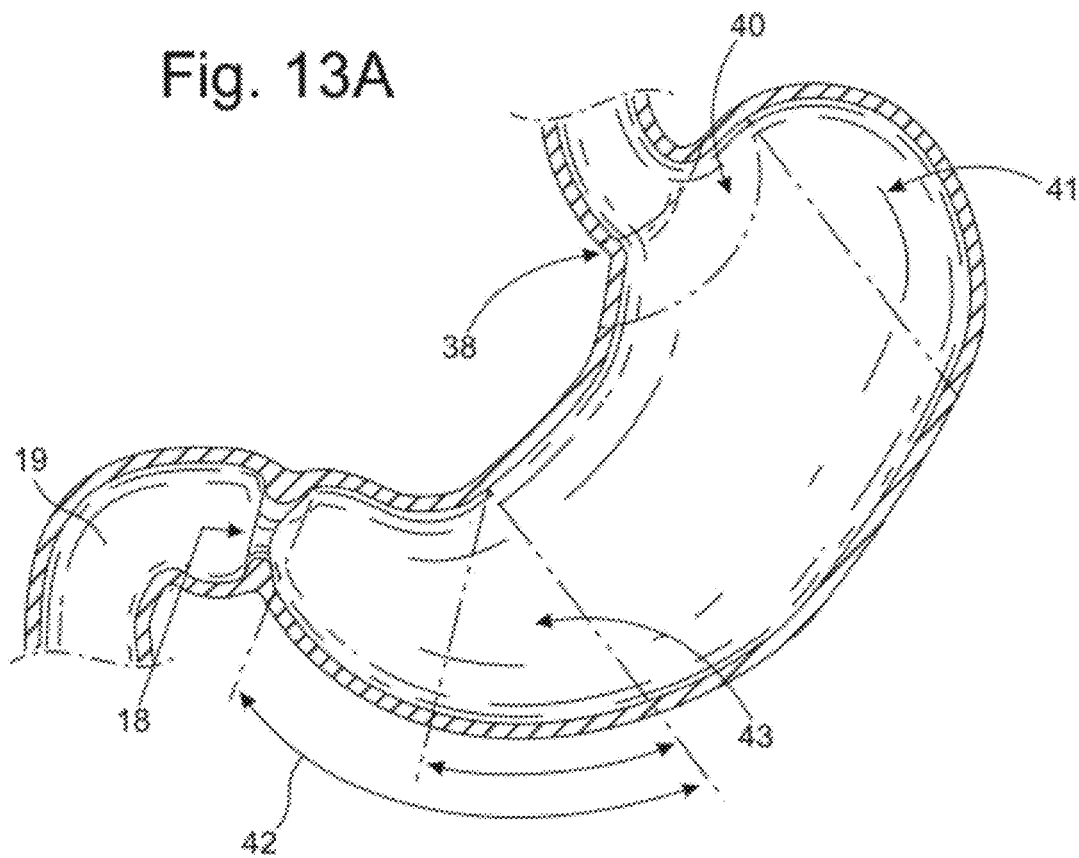
FIG. 13A depicts a side view of a cross-section of a stomach, identifying anatomical features.
Figure 13B:
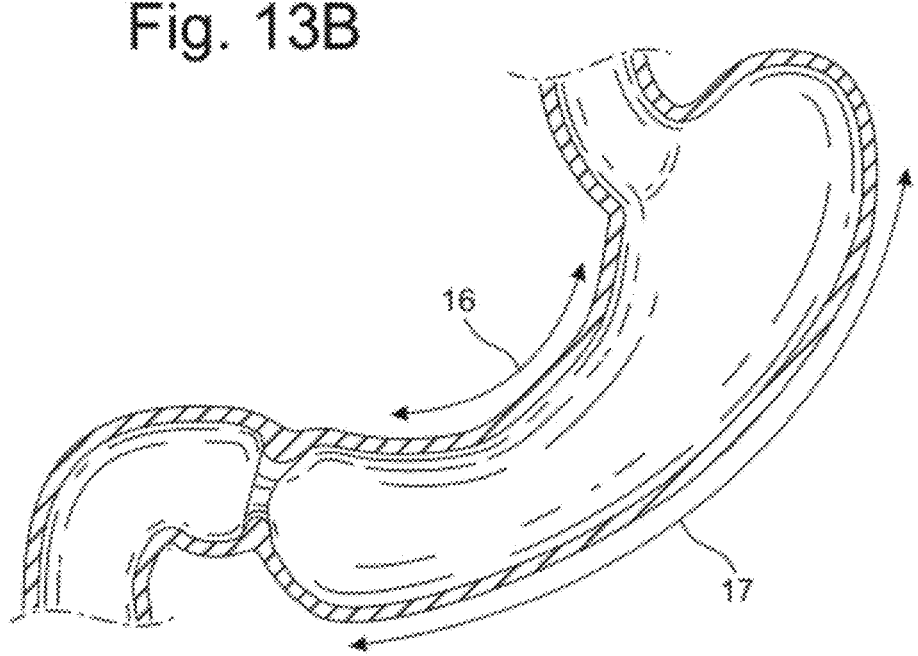
FIG. 13B depicts a side view of a cross-section of a stomach showing its approximate shape when undergoing contractions due to peristalsis.

As mentioned above, the stomach experiences peristaltic waves when something is swallowed. FIG. 13A depicts a stomach cross-section showing the Z line and gastroesophageal ("GE") junction 38, the cardia or cardiac region 40, the fundus 41, the pyloric region which includes the pyloric antrum 42, the pyloric valve 18, and the duodenum 19. FIG. 13B depicts the stomach's lesser curve 16 and greater curve 17. FIGS. 13A and 13B respectively show a representation of the stomach profile when the stomach is at rest and when the stomach is fully contracted during peristalsis and the change in stomach diameter and length. Due to the change in stomach profile, it may be advantageous to have a design that can flex to change with the stomach profile to allow the design to slide or translate along the greater curve 17 or flex as needed, but maintain the relative position of the cardiac element 12.

FIGS. 14 and 15 show an alternate embodiment of the design to adapt to stomach profile changes. In FIG. 14, it shows the cardiac element 12 engaging the upper stomach region while the connecting element 25 is a spring with two closed loops 44 at each end which can compress and flex to accommodate peristalsis within the stomach. FIG. 15 shows these loops 44 compressing during peristalsis to allow the device 10 to maintain its relative position in the stomach and preventing it from migrating past the pyloric valve 18. Another variation of this embodiment would be to leave the loops open and allowed to flex until closed. Another variation would be to keep the loops closed, but include a mechanical stop inside the loop next to where the loop is closed to set a maximum amount that the device can flex.

In yet another embodiment, the connecting element 25 may be made up of two or more members 30. See FIGS. 16A and 16B. As shown in the drawing, the cardiac element 12 would contact the upper stomach or cardiac region 40, while pyloric element 26 contacts the lower stomach or pyloric region 42. The connecting element 25 has three members 30, which are shown as curved wires or ribbons. One member 30 curves to match the lesser curve 16 (LC), while two other members 30 curve to match a median line between the lesser and greater curve 17 (GC), and curve to contact the anterior and proximal surfaces of the stomach to maintain its position even during peristalsis. FIG. 16A shows an optional location for the pyloric element 26 in the pyloric region 42. FIGS. 17A and 17B shows a similar embodiment with another optional location for the pyloric element 26 closer to the pyloric valve 18. In this embodiment, the pyloric element is not intended to contact or block the opening of the pyloric valve.

In another embodiment, peristaltic motion may cause the device 10 to move inside the stomach and could cause the pyloric element 26 to slide from the relative locations such as those shown in FIGS. 18A, 18B and 19. These drawings show a three-element embodiment where the connecting element 25 may have four members 30. FIGS. 18A, 18B and 19 depict a similar embodiment to FIGS. 17A and 17B, but with an additional element to match the greater curve 17. During peristalsis, the greater curve 17 will shorten, and the member 30 that matches the greater curve could flex inward to a convex form. After the peristaltic action is complete, the member 30 may spring back to its original concave form. Using these concepts, additional members 30 for the connecting element 25 may be used beyond the three and four members 30 described here, and could be located in a variety of locations along the midline, lesser curve 16 or greater curve 17 or any combination.

Figure 20A:
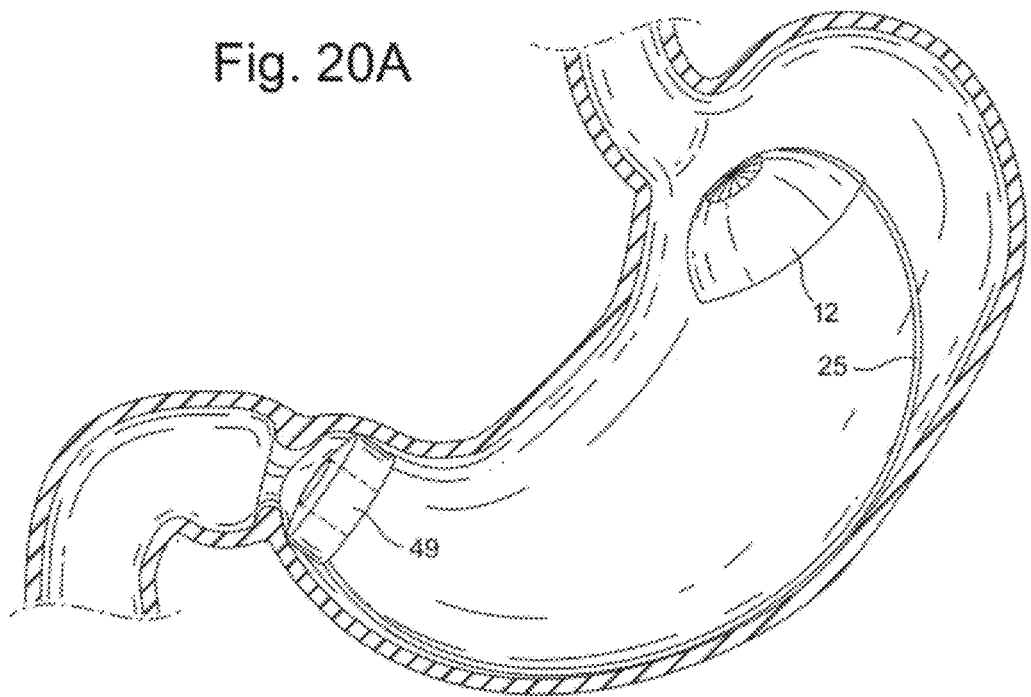
FIG. 20A depicts a side view of an embodiment of the bariatric device of the present invention, located within a cross-section of a stomach.
Figure 20B:
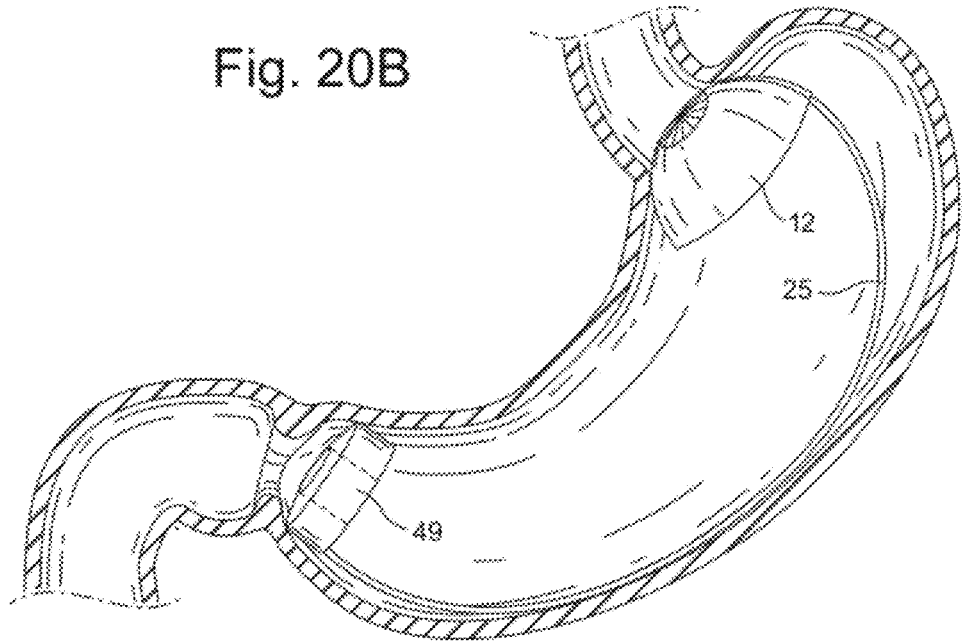
FIG. 20B depicts a side view of the embodiment of the present invention shown in FIG. 20A, located within a cross-section of a stomach that is undergoing contraction due to peristalsis.

FIGS. 20A and 20B depict an embodiment where the cardiac element 12 may be allowed to intermittently contact the upper stomach during peristalsis. The pyloric element may be a rigid or semi-rigid ring 49 and the connecting element 25 may be a spring to connect to the cardiac element 12. Ideally, this ring is curved and smoothed to reduce the potential for irritation. In this embodiment, the ring 49 could engage the lower stomach at a fixed diameter when the stomach is at rest. Compression of the stomach during peristalsis would push the ring 49 towards the upper stomach to allow the cardiac element 12 to intermittently contact the upper stomach and/or cardiac area 40. This may be advantageous to prevent overstimulation of the upper stomach or for other purposes.

Figure 21A:
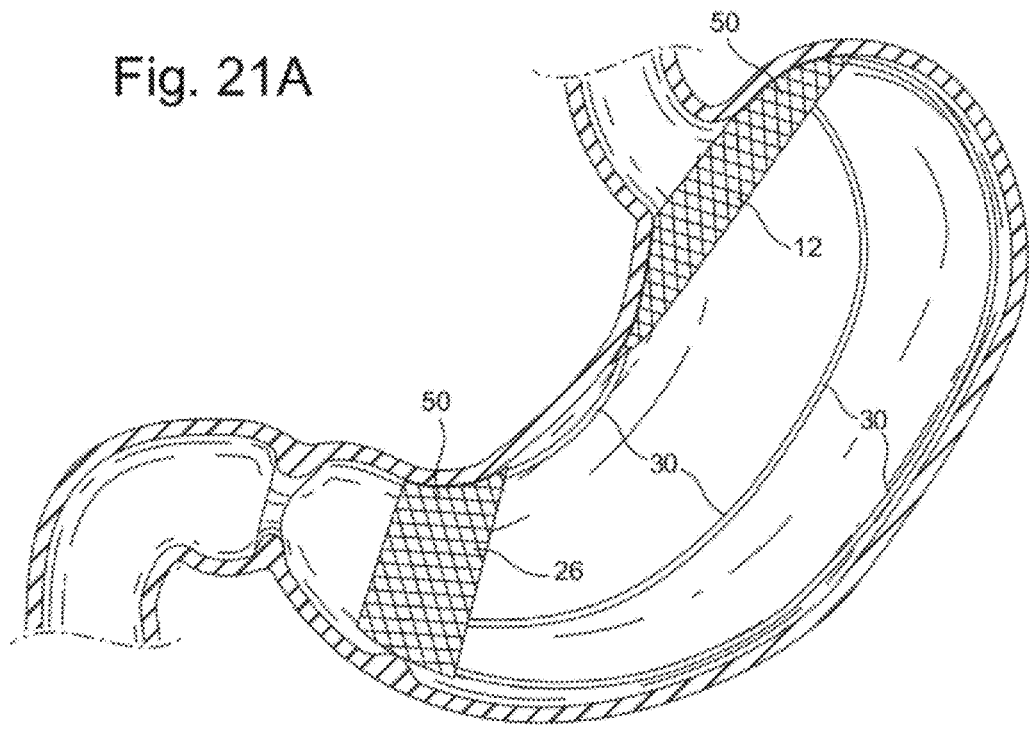
FIG. 21A depicts a side view of an embodiment of the bariatric device of the present invention, located within a cross-section of a stomach.
Figure 21B:
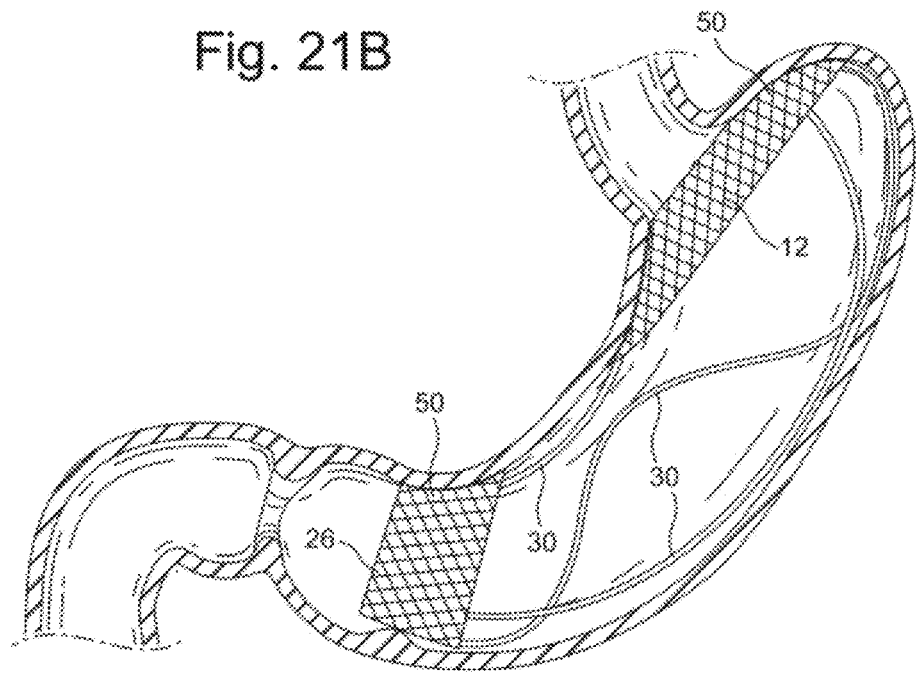
FIG. 21B depicts a side view of the embodiment of the present invention shown in FIG. 21A, located within a cross-section of a stomach that is undergoing contraction due to peristalsis.

In yet another set of embodiments, the bariatric device 10 may be self expanding. FIGS. 21A and 21B depict an alternative embodiment where the cardiac and pyloric elements 12, 26 are self expanding. These elements could be self expanding or have a portion that is self expanding to allow the device 10 to flex with peristalsis, but maintain tension to spring open to apply pressure or contact and position within the stomach. The self expanding portion could be made of Nitinol, silicone, polyurethane, Teflons, stainless steel, super alloys, or other suitable materials or combinations of suitable materials. FIGS. 21A and 21B shows a Nitinol wire mesh pattern 50 applied to a frusto-conical shape to create a shell. The Nitinol wire may act as a stiffening member within the cardiac and pyloric elements 12, 26. The Nitinol wire could be arranged in many different patterns to allow for the appropriate amount of self expansion while allowing the element to compress during peristalsis. The array pattern could include circular arrays, angular arrays, linear arrays, or other suitable arrays. The pattern could be woven or a continuous spiral.

The self expanding function may also assist in deployment by allowing the device 10 to compress and then regain its shape. A preferred method of deployment is to compress the bariatric device 10 into a long narrow shape, which is then placed in a deployment tube, sheath or catheter. The collapsed and encased device 10 is then guided down the patient's esophagus 32 and into the stomach, where the bariatric device 10 is released from the deployment tube or catheter. Once released, the device 10 would expand to its original operational shape. The stiffening member, such as Nitinol wire, may provide adequate stiffness to expand the elements into their operational shape, and maintain that general shape during operation, while allowing flexibility to accommodate peristalsis.

The embodiment depicted in FIGS. 21A and 21B show the cardiac and pyloric elements 12, 26 connected by a connecting element 25 with multiple curved members, which are shown to be a Nitinol wire mesh array 50, but could be made of Nitinol wire, silicone, teflon, another suitable material, or a combination of these materials. The four members of the connecting element 25 have different lengths to allow for proper alignment and seating within the stomach. FIG. 21B depicts how during peristalsis, the stomach will contract and its profile will reduce. The bariatric device 10 may shift and flex within the stomach, but the self expansion feature allows it to spring open and maintain its general position correctly. The connecting element 25 could have a pre-curved bend to form a living hinge to direct where the element should flex during peristalsis as shown in 21B.

Figure 22:
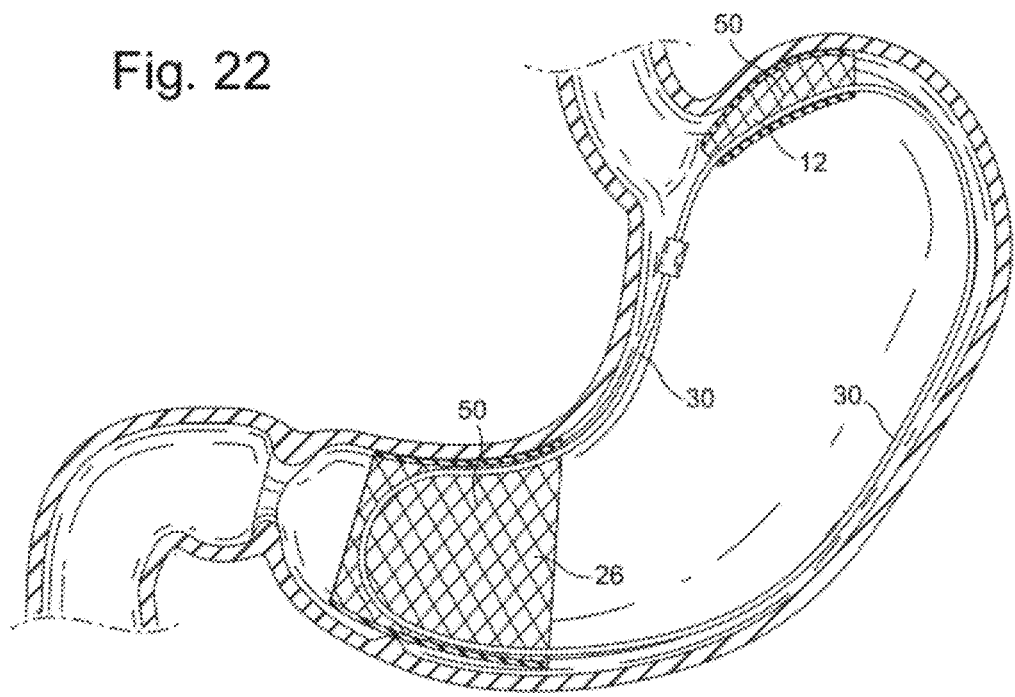
FIG. 22 depicts a side cross-section view of an embodiment of the bariatric device of the present invention, located within a cross-section of a stomach.

As shown in FIG. 22 an embodiment of the cardiac element 12 may comprise a portion of a substantially flattened frusto-conical shape which is adapted to fit the cardia proximal to the esophageal/cardiac opening of a stomach. The cardiac element could also be a portion of a tube or it could be a flat panel, portion of an ovoid, ellipsoid, sphere or other shape. FIG. 22 also shows that a preferred embodiment of the pyloric element 26 may be a steep frusto-conical shape, or a tapered cylinder, which is adapted to fit the pyloric region 42 of the stomach, and preferably sized so that it does not migrate past the pyloric valve 18. As discussed above, these elements may have a wide variety of shapes or may be inflatable, and these are only examples.

Figure 8:
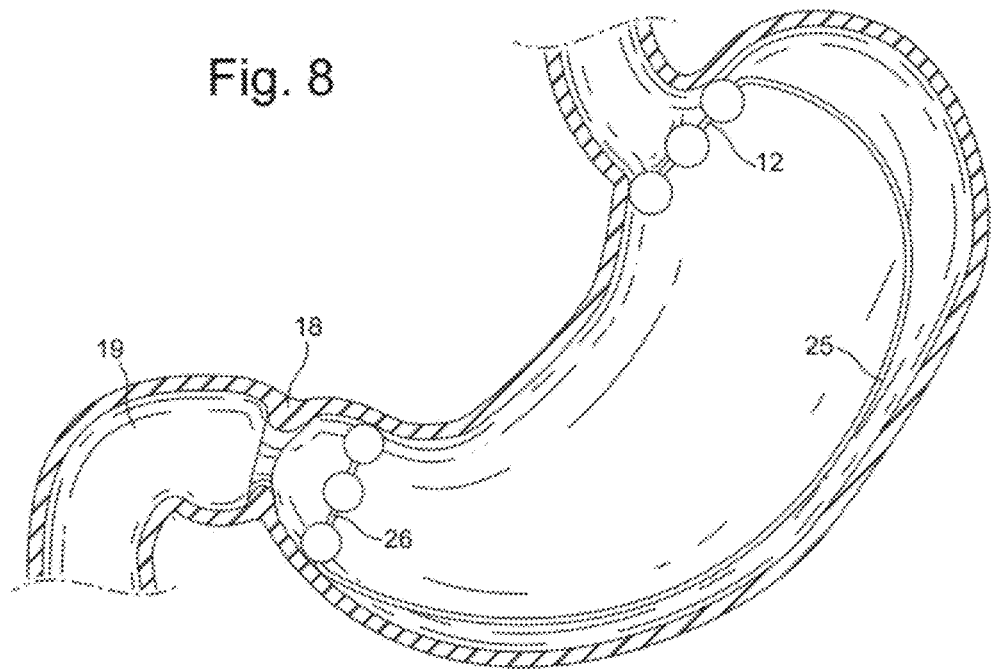
FIG. 8 depicts a side view of an embodiment of the bariatric device of the present invention, located within a cross-section of a stomach.
Figures 23A, 23B:
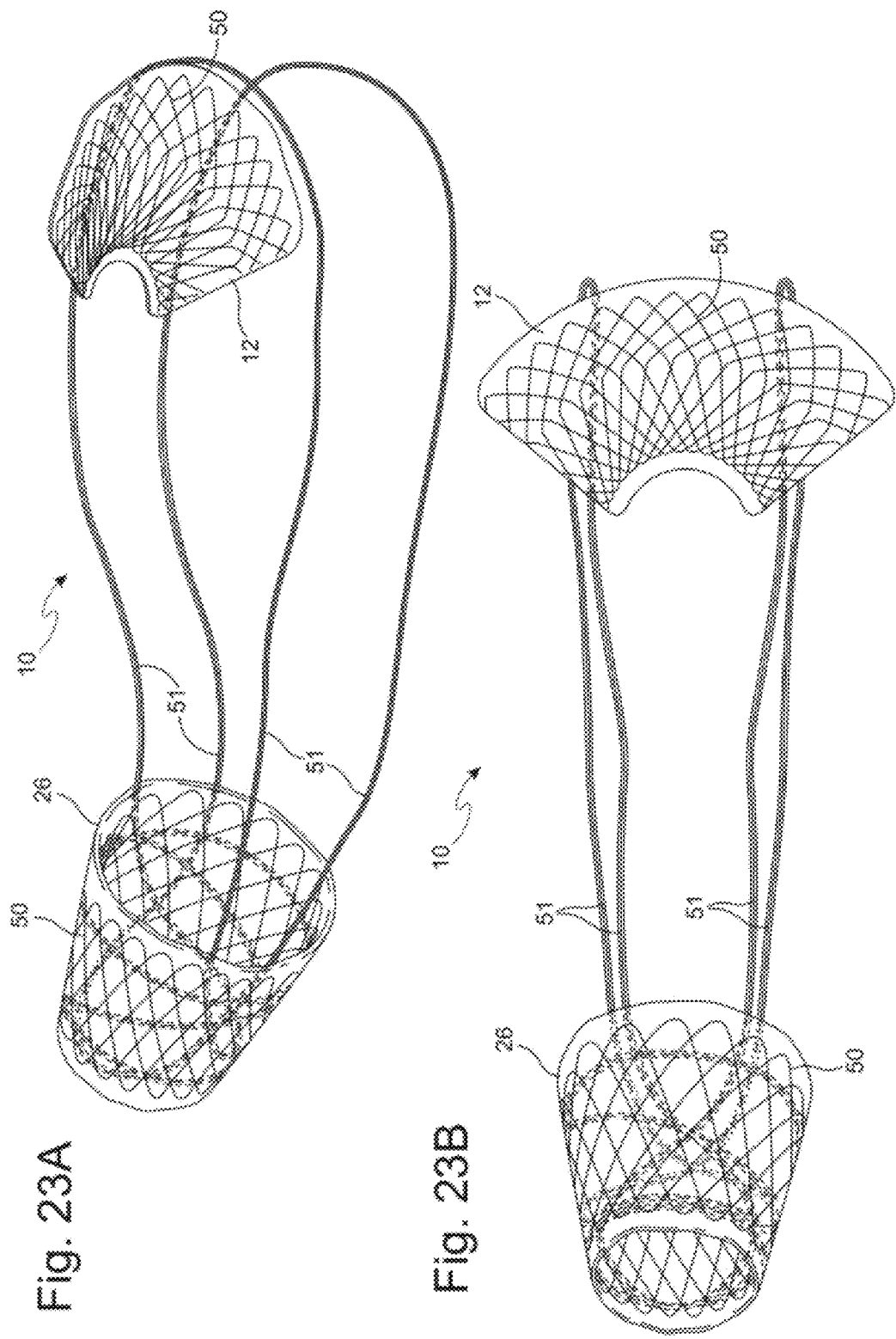
FIG. 23A depicts an underside perspective view of an embodiment of the bariatric device of the present invention.
FIG. 23B depicts a front view of an embodiment of the bariatric device of the present invention.

The four connecting members may be constructed from 2 full loops or 2 loops connected together to create a "FIG. 8" structure. The loops could be contoured to generally follow the curves of the stomach, and could be connected to the pyloric and cardiac elements 26, 12 in a variety of locations. The loops could be oriented to intersect at a variety of locations to provide different configurations with varying structural resistance and flexure points. For example, FIGS. 23A and 23B depict a bariatric device 10 where there are 2 separate closed loops 51 and the loops 51 are crossed in the pyloric element 26 so that the wires do not obstruct the distal opening of the element. The loops 51 are then aligned in a parallel pattern where they are attached to the cardiac element 12. This allows the cardiac element 12 to follow the contours of the loops 51 even when the device 10 is laid flat and the loops 51 are compressed together as could be the case inside the stomach. This could allow for more uniform curved contact of the cardiac element 12 with the cardia 40 and adjacent fundus 41. The parallel orientation of the loops 51 along the cardiac element 12 would provide less resistance of the device 10 just below the GE junction for a more gentle response.

In another embodiment, the 2 loops 52 are connected in a "FIG. 8" pattern where the loops are 52 crossed in the pyloric element 26 and do not obstruct the distal opening of the pyloric element 26. See FIGS. 24A and 24B The loops 52 cross again just below the opening of the cardiac element 12, which allows the cardiac element 12 to flare more when the device 10 is laid flat and the loops 52 are compressed together such as would be the case inside the stomach. This could allow for more focused, linear contact of the cardiac element 12 with the cardia 40 and adjacent fundus 41 in the stomach. The cross of the loops 52 below the cardiac element 12 would provide more structural strength of the device 10 just below the GE junction 38 for more acute response. Where the connecting element loops cross, they may be joined together by a means of fixation to hold them together. These could be held together by adhesive or a separate joint connection 105. The shape of the joint connection could follow the shape of the connecting element or it could be a portion of a frusto-cone or other.

To increase the acute response, a stiffening member such as a wire loop or other could be added cardiac element 12 to direct stiffness in a desired area. FIGS. 25A and 25B show one possible orientation for a stiffening member, but other orientations, shapes and additional members could be added to generate a specific response. FIGS. 25A and 25B also show a cardiac element with 2 members, the first member being proximal and the second member being distal to apply pressure in these focused areas. These members are shown as portions of a frusto-cone, but could be different shapes. Similarly, these members of the cardiac element could also be oriented in different locations.

Figure 26:
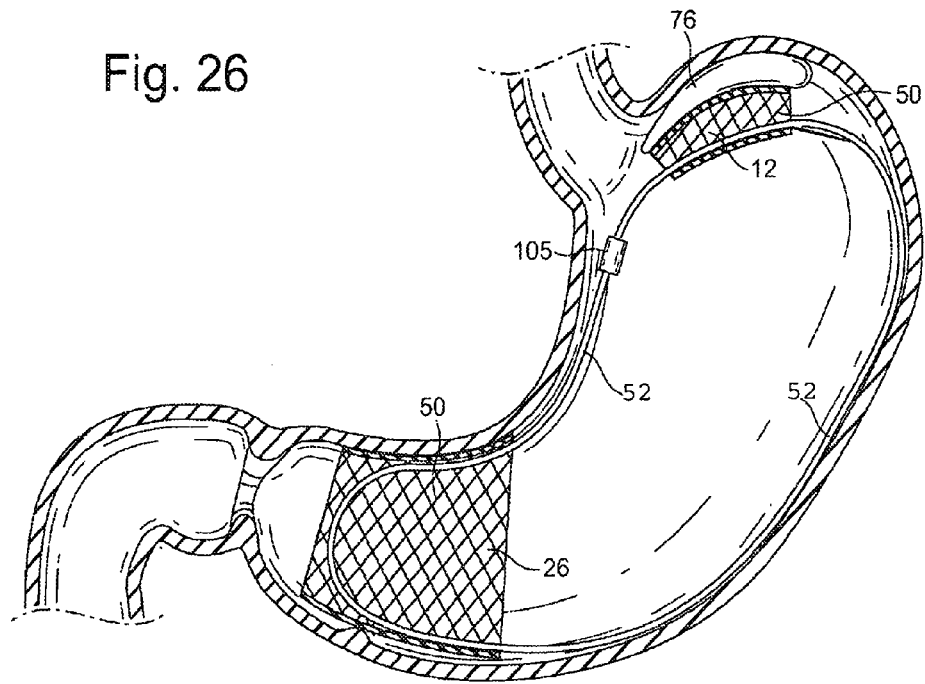
FIG. 26 depicts a side cross-section view of an embodiment of the present invention, having an adjustment mechanism in the cardiac element in an inflated state, located within a cross-section of a stomach.
Figure 27:
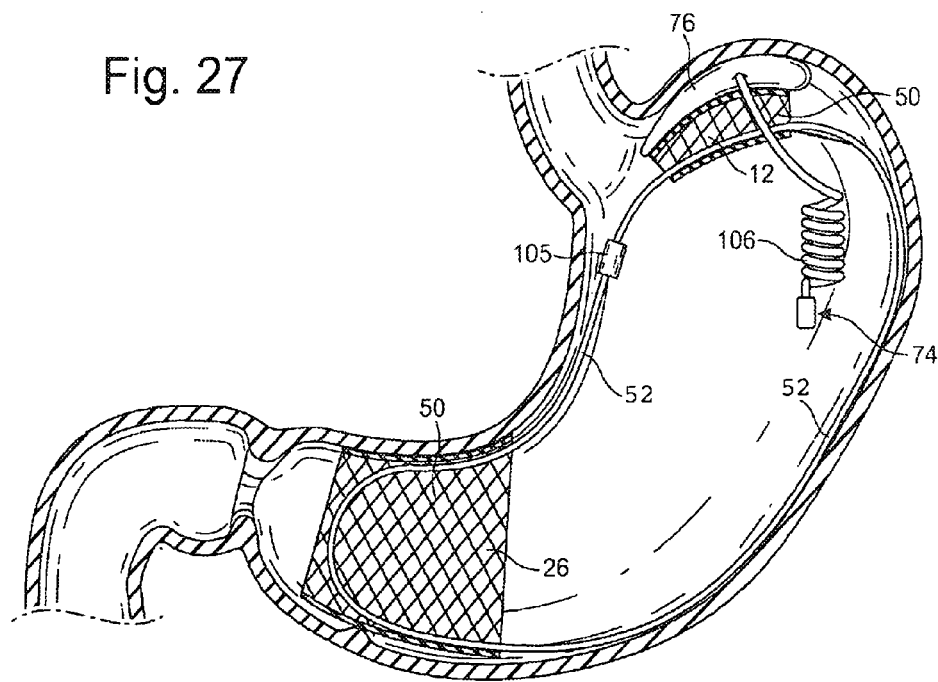
FIG. 27 depicts a side cross-section view of an embodiment of the present invention, having an adjustment mechanism in the cardiac element in an inflated state, located within a cross-section of a stomach.

Another variation of this embodiment could include an inflatable member 76 placed on top of the cardiac member to allow for adjustability of the device once it is in place. FIG. 26 shows a side view of an embodiment with the inflatable member 76. This member could have an inflation element, which could be a self sealing septum, valve or self sealing membrane on the surface of the inflatable member itself. In FIG. 26, the inflation element is not shown, but could be located near the pyloric element for ease of access, but could also be located at different sites. FIG. 27, shows a variation of the inflation element where the valve 74 is attached to the cardiac element by a retractable inflation tube 106. The retractable inflation tube 106 may be constructed of a coiled tube, which may be may be contained in a housing. Alternatively, the retractable inflation tube 106 may be attached to a separate leash or tether. The valve 74 can be grasped inside the stomach using a standard grasper or snare, and then pulled up the esophagus for access outside the body while maintaining the device inside the stomach. The inflation element may be a slit valve that can be accessed by a blunt needle or small diameter instrument to push through the valve to allow fluid to be added or removed. After the appropriate volume of fluid has been added, the retractable inflation tube 106 can then be placed back into the stomach. Preferably, the retractable inflation tube 106 would be designed so that it would not pass through the pylorus. FIGS. 28A and 28B show a front and back side view of the inflatable member 76 in an inflated state.

Figure 29:
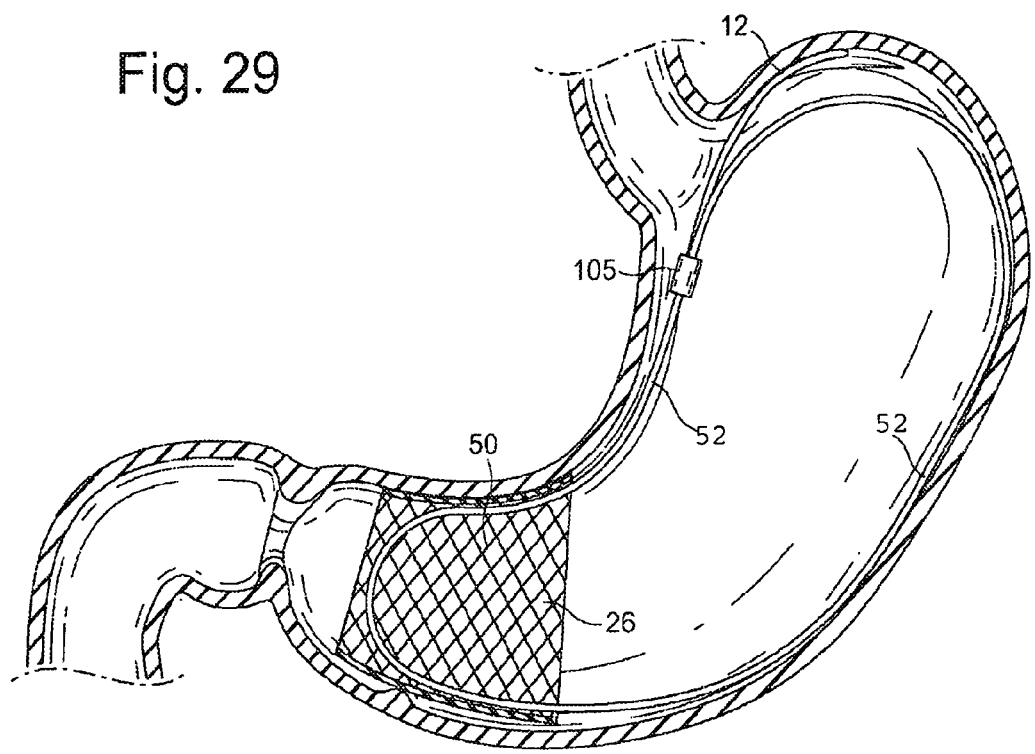
FIG. 29 depicts a side cross-section view of an embodiment of the present invention, having an adjustment mechanism in the cardiac element in an inflated state, located within a cross-section of a stomach.

In another embodiment, FIGS. 29, 30A, and 30B show a configuration where the connecting loop elements form a FIG. 8, and the cardiac element 12 is constructed from a wireform similar to the stiffening member. The stiffening member could be in a variety of other orientations, shapes or patterns, and additional members could be added to engage specific areas of the stomach to generate a specific response.

This element could also be adjustable in length, width, curvature or shape to generate a specific response.

Figure 31A:
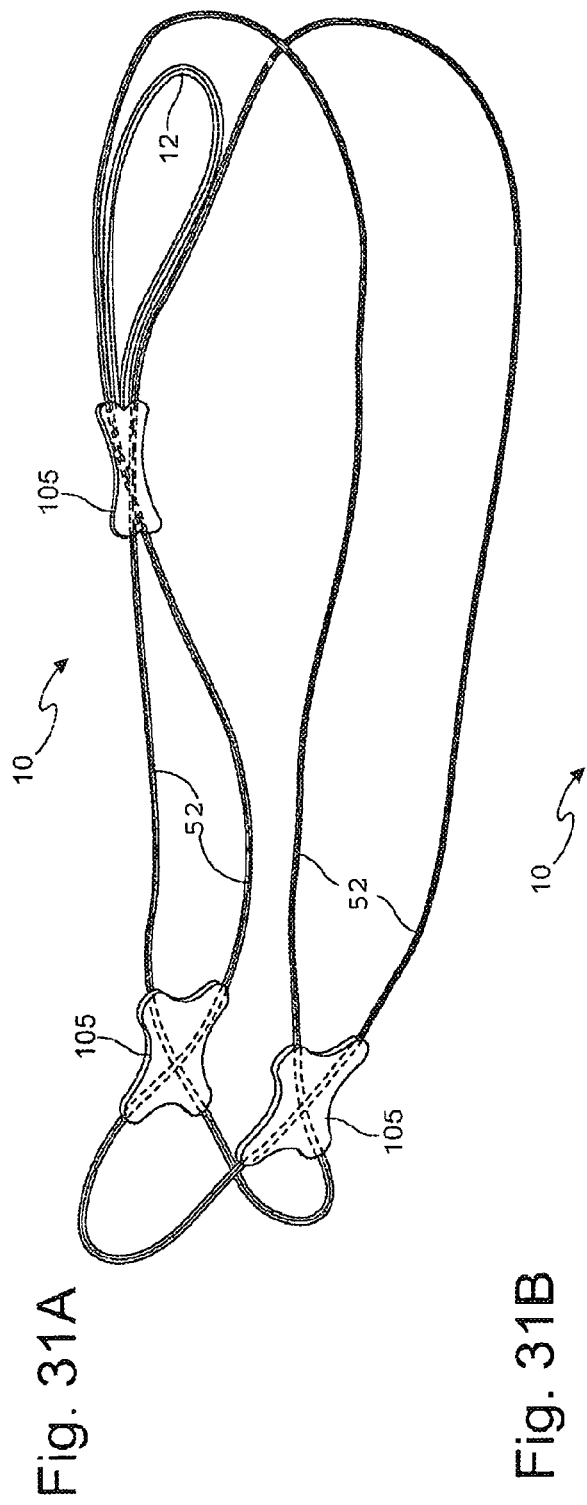
FIG. 31A depicts an underside perspective view of an embodiment of the bariatric device of the present invention.
Figure 31B:
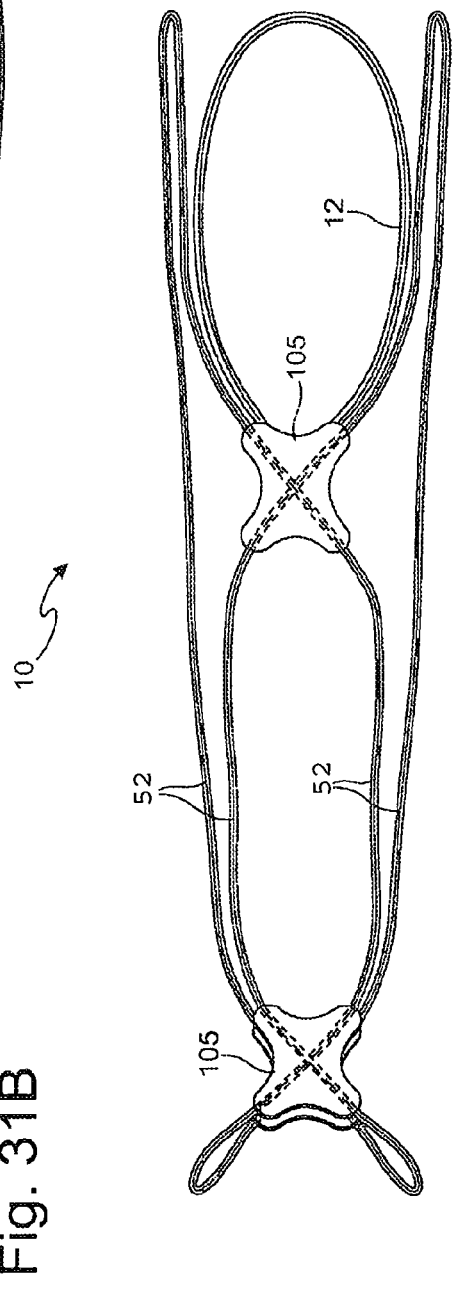
FIG. 31B depicts a front view of an embodiment of the bariatric device of the present invention.

In another embodiment, FIGS. 31A and 31B show an embodiment where connecting loop elements form a FIG. 8, and the pyloric element is constructed by the 2 connecting loops crossing with connecting element joints 105. The crossed connecting elements would engage the lower stomach to provide adequate resistance from passing the pylorus while maintaining pressure against the upper stomach. Additional loops could be added to the pyloric element or cardiac element to create a variety of profiles.

Figure 32:
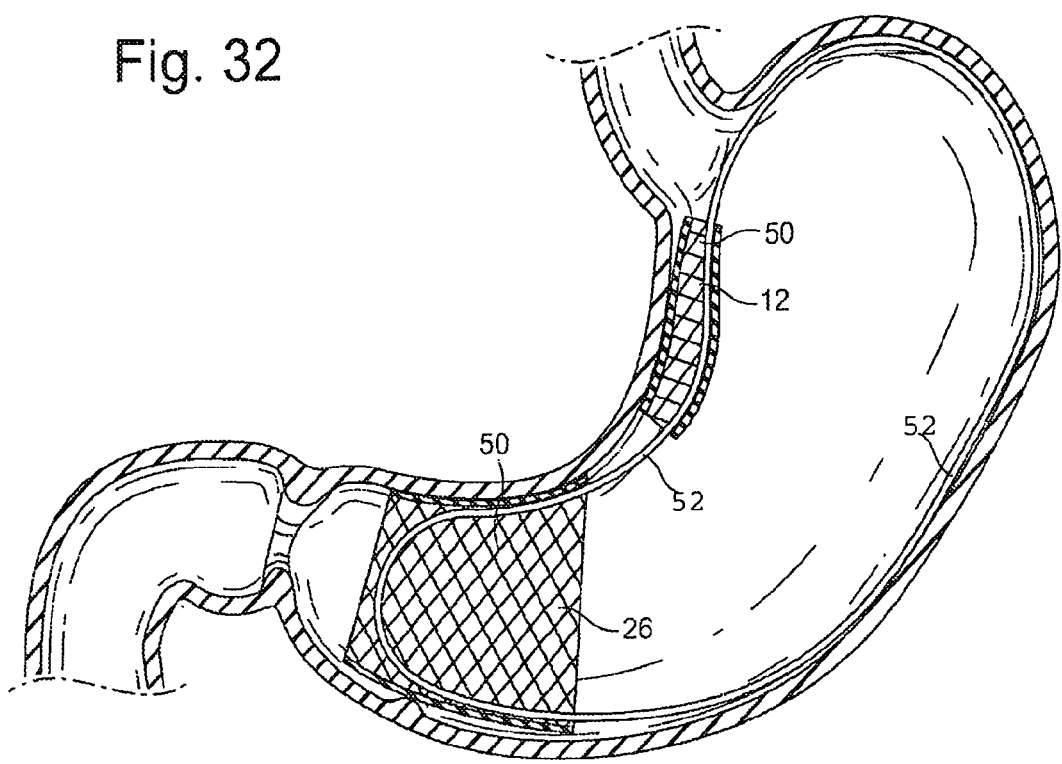
FIG. 32 depicts a side cross-section view of an embodiment of the bariatric device of the present invention, located within a cross-section of a stomach.

In another embodiment, FIGS. 32, 33A, and 33B show a cardiac element that is focused on the distal cardia. Similar to the other embodiments, this cardiac element may also contain a balloon to inflate to change the width of the device.

Figure 35:
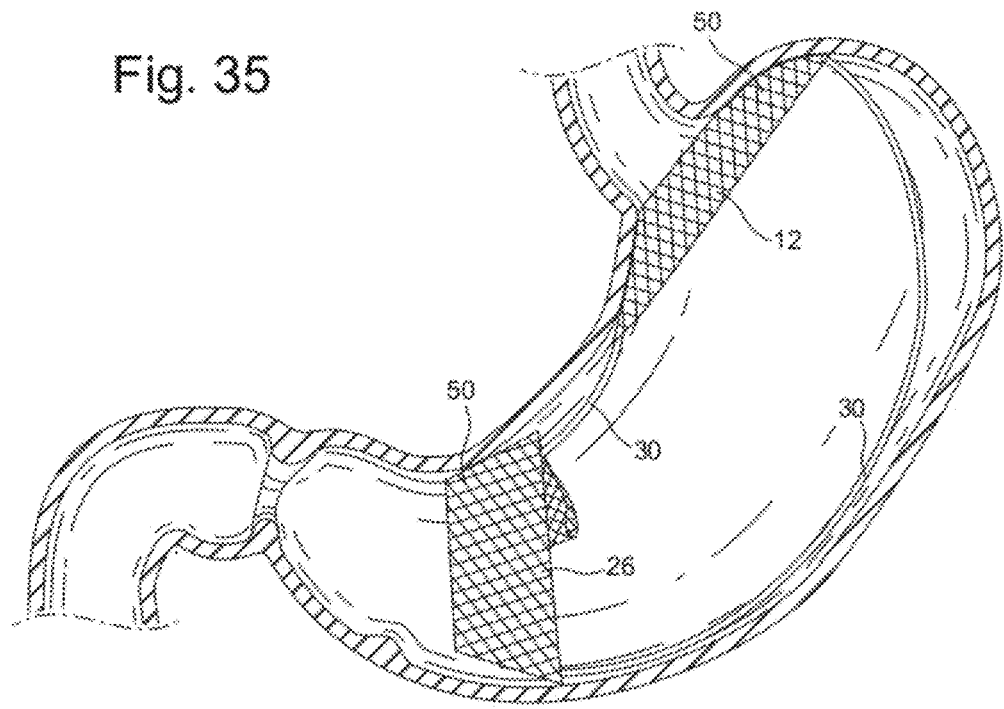
FIG. 35 depicts a side view of an embodiment of the bariatric device of the FIG. 34A in a folded state, located within a cross-section of a stomach.

In another embodiment, the cardiac and pyloric element may have substantially the same shape. See FIGS. 34A, 34B, 34C, 34D and 35. These figures show a device where the both elements are self-expanding flattened frusto-cones. Since the proximal and distal portions are the same, the device is symmetrically arranged on the connecting element and can be placed in either orientation. In another variation, the device may not be symmetrically arranged. In the symmetrical embodiment, the device can migrate out of position and/or rotate, and then re-seat with peristalsis without concern of regaining the proper orientation. As shown in FIGS. 34C, 34D, and 35 when the flattened frustocone is placed or migrated into the antrum or lower stomach it may fold to create a wavy structure. Because the structure is wide, the device may sit higher in the lower stomach, above and adjacent to the proximal antrum and the incisura angularis. It may also sit at the proximal antrum. During peristalsis, the device 10 may move in the stomach, but may come to rest near the proximal antrum when the stomach is at rest or it may sit lower. Similarly, the connecting elements used in this embodiment have the same profile for the proximal and distal portions which have a wide profile and may prevent the distal portion from seating low near the pyloric valve or contacting the pyloric valve. This folded structure may act as a restriction element, creating a tortuous path or a valve for chyme to pass through prior to passing through to the area adjacent to the pylorus and through the pyloric valve. The restriction element may aid in slowing gastric emptying and increase a feeling of satiety. Although the figures show a device with a flattened frusto-cone, many other shapes may be used. These shapes could be could be a ring, a disk, a portion of a cone, portion of frusto-cone, a sphere, a portion of a sphere, an oval, an ovoid, a tear drop, a pyramid, a square, a rectangle, a trapezoid, a wireform, a spiral, a preformed wavy shape, multiple protuberances, multiple spheres or multiples of any shape or other suitable shapes. It could also be any other shapes previously described. These shapes could fold and change form once placed into the stomach to perform a different function such as slowing gastric emptying by creating a tortuous path. Similarly, the element could be preformed with folds or waves. Given that the cardiac and pyloric elements may have the same shape in certain embodiments, and/or may be interchangeable in position within the stomach, the claims may refer to them as a first element and a second element.

Figure 36:
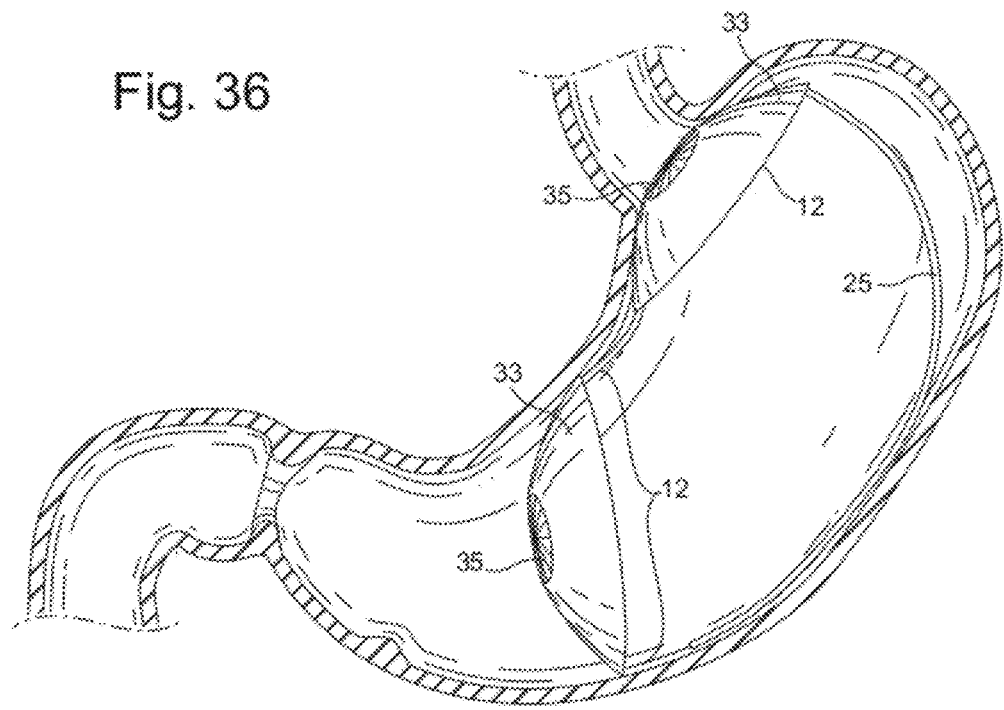
FIG. 36 depicts a side view of an embodiment of the bariatric device of the present embodiment, located within a cross-section of a stomach.
Figures 38C, 38D:
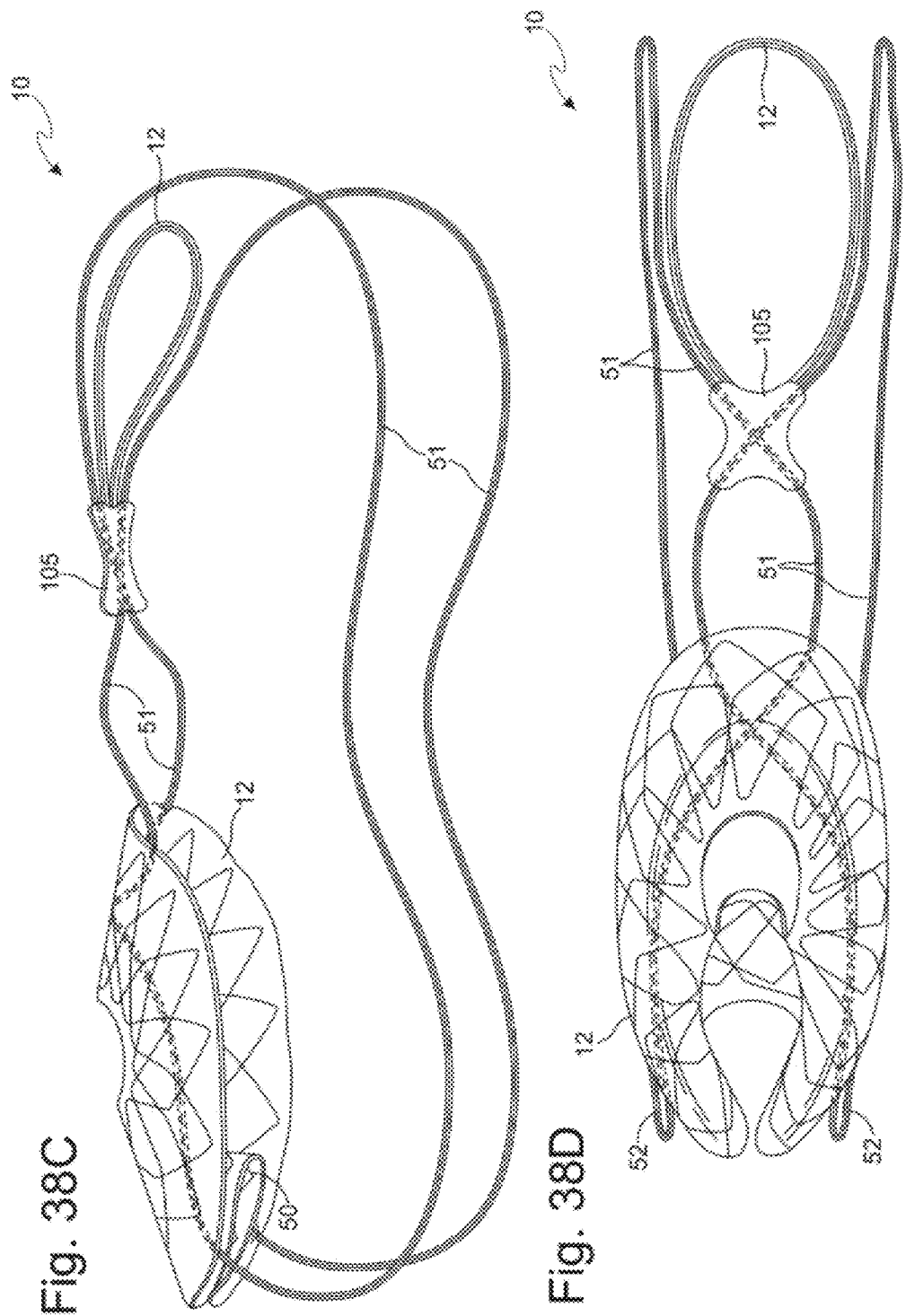
FIG. 38C depicts an underside perspective view of an embodiment of the bariatric device of the present invention with one of the elements in a folded state.
FIG. 38D depicts a front view of an embodiment of the bariatric device of the present invention with one of the elements in a folded state.

These cardiac and pyloric elements may also contain a restriction element to slow gastric emptying. Such restriction element could comprise an additional membrane or valve. FIG. 36 shows a device with a proximal and distal element that are hemispherical thin walled shells 33. These restriction elements may comprise a valve 35 with multiple slits to reduce the flow of food through either element. As a variation, a restriction element could also comprise a hole to allow for food to pass through or no lumen to allow food to pass around the elements as they flex or fold. Another variation of the restriction element to slow gastric emptying would be to have a thin walled flexible membrane, small protrusions, wire loops, or fingers that extend from the inner surface of the cardiac or pyloric elements. FIGS. 37A and 37B shows the example of a device with a conical pyloric element with a thin walled flexible membrane 35 crossing through the center of the element. This membrane shows an oval opening, but the opening could be a slit, a hole or other shape. In this embodiment, the pyloric element has a wide profile and may maintain its position near the proximal antrum and the incisura angularis. In this embodiment, the device is not intended to directly contact the pyloric valve or pyloric opening. In other embodiments, however, the pyloric element may be sized to contact those areas.

FIGS. 37B, 37C, 37D, and 37F show other examples of a restriction element, which may include a reduced lumen, valve or tortuous path to reduce the flow of food through the pyloric element 26. FIGS. 37C and 37D show multiple flexible members 107 that extend from the internal surface of the pyloric element 26 to reduce the flow of food. Similarly, FIGS. 37E and 37F show multiple flexible members 107 that cross the internal surface at different heights to slow gastric emptying.

In another embodiment, the same structure as described above for the foldable pyloric element 26 may be combined with a different cardiac element 12 such as the wireform structure shown in FIGS. 38A, 38B, 38C, and 38D This could combine unique features of the wireform to apply pressure at the cardia, while also using the folded design as a restriction element for slowing gastric emptying through the proximal antrum. As described above, any combination of cardiac and pyloric elements disclosed herein can be used.

Where the connecting element 25 is formed from loops, the loops could be formed from Nitinol wire. The Nitinol wire used for the connecting elements or any elements in the device could be passivated to improve acid resistance. They could also be coated in an acid-resistant coating 53 such as silicone or silicone covering, PTFE, or other suitable coating, or not coated. These loops could also be made of spring steel, stainless steel, super alloys, teflons or other suitable materials or combinations of materials. The loops could be closed or connected in a variety of ways. For the example of Nitinol, the loops could be closed by a glue joint where the wire loop ends are glued inside of another tube. They could also be closed by a crimping, swaging, welding or joined by a mechanical mechanism. The loops could also be left open, if a feature is added for adjustability and it is preferred to have the loops open with both ends fixed to the elements as needed.

Figure 39A:
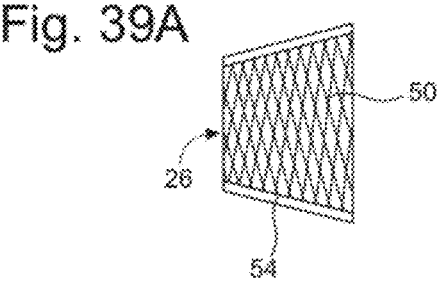
FIG. 39A depicts a side view of a pyloric element of an embodiment of the present invention.
Figure 39B:
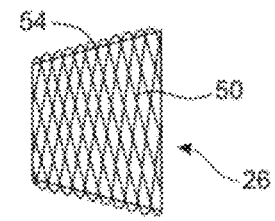
FIG. 39B depicts a side view of a pyloric element of an embodiment of the present invention.

The contact members of the elements may be comprised of a variety of materials. For example, the Nitinol wire pattern of the cardiac, pyloric, and or connecting elements 12, 26, 25, may be exposed for direct contact with the stomach or the wire could be covered or sealed in another material, such as silicone, PTFE, polyurethane or other suitable materials. For example, FIG. 39A depicts a pyloric element 26 where the wire mesh 50 is covered in another material to create a smooth surface for the contact member 54 to facilitate sliding within the stomach. Alternatively, FIG. 39B shows the wire exposed to the stomach mucosa surface. This shows how the wire array 50 could be arranged and formed to add a wavy pattern to increase to profile of the wire above the element's nominal surface, which in this case is shown as a cone with the wire protruding above the cones surface. This would allow the wire to act as a macro texture surface for the contact member 54 to grip the stomach surface to reduce sliding or it could provide a macro texture for tissue ingrowths. The Nitinol may be treated with a surface finish, passivation or coating to improve its acid resistance within the stomach.

The contact and stiffening members of the elements may be separate, entirely integrated, or both. For example, if a cardiac element 12 is made entirely of Nitinol wire, the wire acts as both a contact member and a stiffening member. The same would apply if an element were made entirely of silicone; the silicone would act as both a stiffening and contact member. In another embodiment, where Nitinol wire is embedded in another material such as silicone, the Nitinol wire acts as a stiffening member and the silicone acts as a contact member. In another embodiment, the Nitinol wire may be partially exposed and partially covered by the silicone (and/or on the interior of the element), in which case the Nitinol wire acts as both a stiffening and contact member. In certain embodiments, the combination of materials may act as a stiffening member. For example, an embodiment where the contact member is silicone with Nitinol wire embedded, the silicone may act in conjunction with the Nitinol to provide more stiffness than the Nitinol could achieve alone. Various combinations of stiffening and contact members may be apparent to those skilled in the art.

As mentioned above, a preferred device 10 has adjustability or adaptability to match any changes in the patient over time. A variation of the above embodiments would be to allow the device 10 to be adjustable via an adjustment element 60. This adjustability could be in the length, shape, angle or stiffness of the cardiac, pyloric, and/or connecting elements 12, 26, 25. Similarly, different sized devices could be manufactured and the device replaced with a different size.

The bariatric device 10 could be adjustable to allow for adjustment at the time of placement or could be adjusted at a later time. This adjustability could be achieved by having a variable spring tension in one of the elements to allow the device 10 to extend, contract, or distort as needed. It could also be achieved by adding an expansion joint 75 in a member to elongate or compress as needed. This expansion could be a manual adjustment performed by the physician in the office through a gastroscopic procedure. This expansion could be achieved by various mechanisms, including but not limited to those operated by: rotating a threaded member, ratcheting backwards or forwards, a hydraulic mechanism, a pneumatic mechanism, a cam, a tension mechanism, a telescoping mechanism or other elongation or contraction mechanisms. The outer surface of the connecting element 25 is preferably smooth with rounded or gently angled edges to prevent irritation of the stomach during peristalsis, although sharp angles may be preferred in some applications. To create a smooth interface, these elements could be encased in a sleeve or sheath that could be removed or remained fixed during the expansion. A sheath may not be required if the expansion joint 75 is designed with smooth contours on its own.

Manual Actuation

The device 10 could also be adjusted by manual means inside the stomach by using a gastroscopic instrument to come into direct contact with the device 10.

The instrument could also act as a pusher or puller to activate a pulley mechanism or a clipping mechanism. For example, the connecting element 25 could be a ratchet or strut with multiple positional features such as holes, grooves, teeth or wedging action. The device 10 could have a feature to engage the ratchet teeth or positional features such as a pin or clip or other. The instrument could retract the pin or compress the clip and then reposition this feature in the next available location.

In another embodiment, the members of the connecting element 25 could have multiple beads or spheres 62 that are captured by a cuff or ring retainer on the cardiac element 12. An instrument could be used to expand the cuff to pull the bead through for positioning. Similarly, the cuff could have a keyway retainer feature that allows the bead to only fit through a specific location and then lock into position where the beads connect to the wire or ribbon or tube.

Figure 40A:
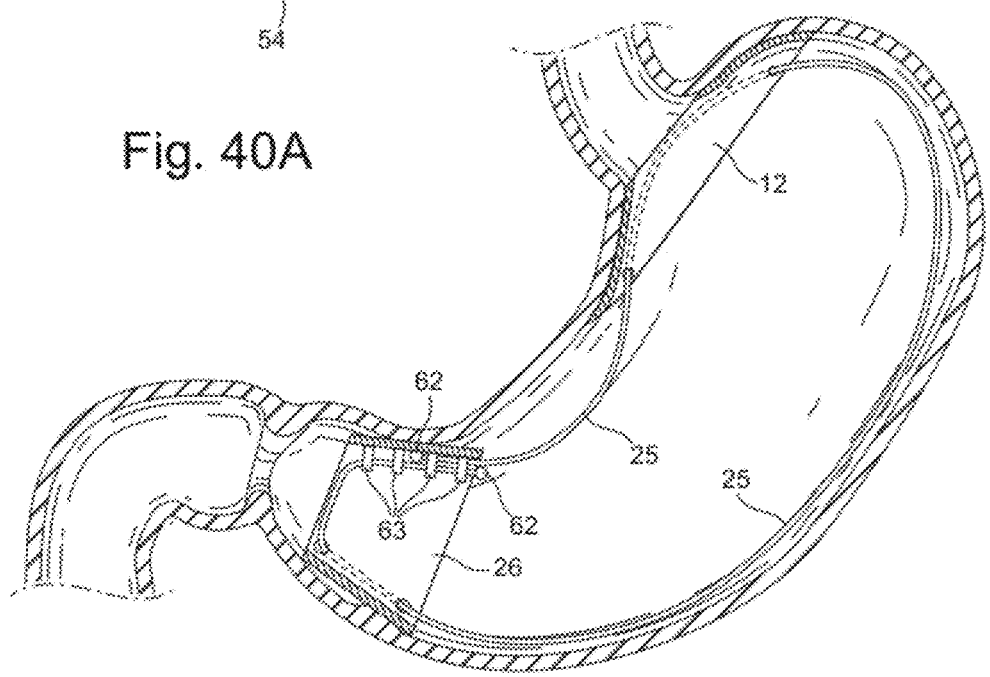
FIG. 40A depicts a side view of an embodiment of the bariatric device of the present invention, located within a cross-section of a stomach.
Figure 40B:
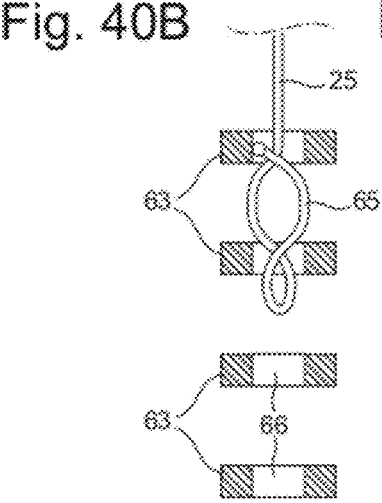
FIG. 40B depicts a side view of a retainer strap and clip adjustment mechanism of an embodiment of the present invention.
Figure 40C:
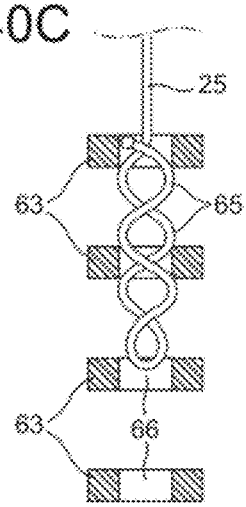
FIG. 40C depicts a side view of a retainer strap and clip adjustment mechanism of an embodiment of the present invention.
Figure 40D:
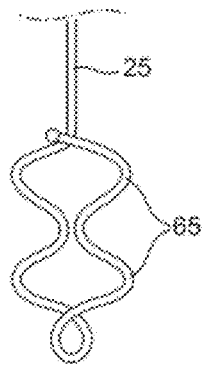
FIG. 40D depicts a side view of a retainer strap and clip adjustment mechanism of an embodiment of the present invention.

FIGS. 40A, 40B, 40C and 40D shows several examples of compressible clips 65 acting as a "bead" or positional feature that could be used for adjustability. For example a retainer strap 63 of silicone could be bonded on both sides to create a narrow passageway 66 where the clip 65 could be placed in the compressed position, and then expand open after passing through the strap 63 to maintain its position. Several straps 63 could be bonded in a row to create several positional locations. FIGS. 40B and 40D shows the clip 65 in is open, relaxed state, where 47C shows the clip 65 in a compressed state where it can pass through the retainer strap 63.

Another option for adjustability would be to use a locking ring to fix the location of the connecting elements 25 into the pyloric element 26. The pyloric element 26 could have several positional features connected to it. The connecting element 25 could also have several positional features attached to it. When the positional features of the pyloric element and connecting loop are aligned, a locking ring could be placed inside to hold the position of the elements together and to alter the length of the whole device 10 to be longer or shorter. In another embodiment, the ring could be fixed to the pyloric element 26 and compressed to capture the positional features located along the connecting element 25.

Figure 41:
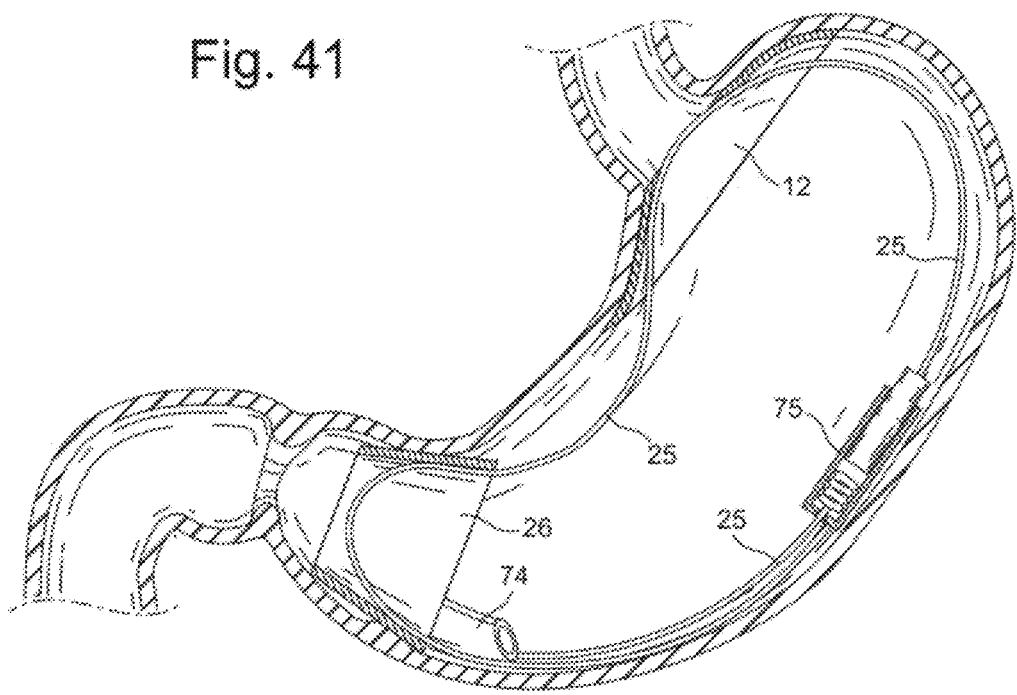
FIG. 41 depicts a side cross-section view of an embodiment of the bariatric device of the present invention, located within a cross-section of a stomach.

In another embodiment, an instrument could act as a screw driver to rotate a member to thread the two elements closer or farther apart. The instrument could also have a needle to inject fluid into an inflation element 74. Such an element may be a self sealing membrane to increase or decrease the length, diameter or stiffness through positive displacement of an expandable body. The self sealing membrane could be an injection port or it could be a self sealing surface on the expandable body, or the entire expandable body could be comprised of a self sealing surface. In all descriptions below, the term inflation element 74 can also refer to an injection port or to an area on the expandable body with a self sealing membrane. The self sealing membrane could also be a self sealing valve which can be accessed by a blunt needle or tube to allow access to add or remove fluid. The valve could be attached directly to the expandable member or it could be attached by a tube. FIG. 41 shows an inflation element 74 fixed to the pyloric element 26 or the connecting element 25. This valve or port could be connected by a fluidic path to an expandable body such as a sealed inflatable body inside of an expansion joint 75 such as a piston and cylinder. The valve could be accessed by an endoscopic instrument with a blunt end, while an injection port could be accessed by an endoscopic instrument with a non-coring needle where saline or other suitable fluid could be injected or removed from the port which would allow the inflatable body to expand or contract to control the length of expansion. Although this figure shows one expansion joint 75, the device 10 could contain one or more with a manifold set up to deliver fluid from the port to all of the expansion joints. In an alternative embodiment, the system could also have an expandable body such as a syringe type joint which would not require a sealed internal inflatable body.

FIGS. 26, 27, 28A, and 28B show an embodiment, where an inflatable body could be located on the cardiac member. An inflatable body could also be placed on the pyloric element(s)

to increase the length or diameter. An inflatable body could also be placed along the connecting element to change the profile of the device. An embodiment could contain one or more inflatable bodies at the cardiac, pyloric, or connecting elements or any combination of the above. Inflating fluid, which could be saline, water, air, or other suitable substances, may be inserted or removed through the inflation element 74 to increase or decrease the size of the inflatable body 76. In such manner, the amount of contact and/or pressure imparted by the cardiac element 12 on the cardiac region 40 and/or the upper region of the stomach may be adjusted, either while the device 10 is in the stomach, or prior to placement. This balloon could cover the entire cardiac surface or could only cover portions of the cardiac surface to direct the inflation for a specific response. There may be one or more inflatable portions on the cardiac element 12. The device 10 could contain linear and radial inflatable bodies.

A gastroscopic instrument could also deliver heat directly to an expandable body such as a heat expanding mechanism (such as one made of Nitinol) for expansion of a wax or wax-like expansion member.

For example, a Nitinol clip could clip into a positional location on a strut. The instrument could heat the clip to release and then reposition it into a different location, remove the heat and allow the clip to re-engage the positional feature to lock it into place.

The instrument could also have an inflatable body or a balloon to allow for physical contact with the device 10 to disengage a feature for repositioning into another location.

Figure 42:
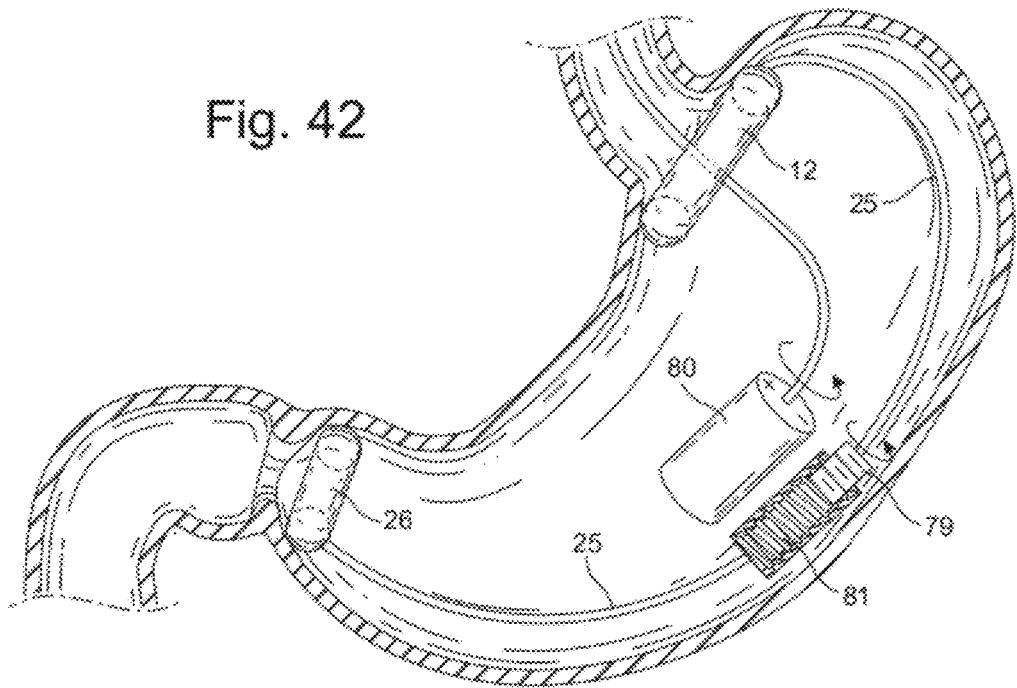
FIG. 42 depicts a side view of an embodiment of the bariatric device of the present invention, located within a cross-section of a stomach.

Magnetic actuation. Another adjustment mechanism could use magnets. See FIG. 42.

For example, the connecting element 25 could contain a thread with a magnetic nut 79 placed over it. Another strong magnet, the controller magnet 80, could be placed in close proximity to the implanted magnet to cause it to rotate. The rotation of the controller magnet 80 could create a magnetic field which would cause the internal magnet 79 to turn allowing it to advance and retreat along the threaded member 81.

The controller magnet 80 could either be external to the body or it could be placed on the end of a gastroscopic instrument for close proximity.

The controller magnet could be a magnet or an electromagnet to increase the intensity of the field and to improve magnetic coupling to ensure actuation.

The controller magnet 80 could also be multiple magnets to improve magnetic coupling.

Another means of manually adjusting the length of the device 10 would be to have modular pieces that could attach or adhere to the cardiac or pyloric elements 12, 26. For example, an additional frusto-cone could be placed over the pyloric element 26 to increase the length of the overall design. Several could be stacked together to create a variety of lengths. Stacking frusto-cones could also be distanced from one another with a balloon on either frusto-cone to increase the distance between the two.

A variation of this embodiment would be to have an additional member that could be collapsible or compressible and inserted down the center of the pyloric element 26. Once it passes the pyloric element distal surface, the modular element would expand and attach to the outer surface. Several modular elements could be stacked together to create a variety of lengths.

An alternative embodiment could have an additional element that could also pass down the center of the pyloric element 26 and expand past the distal surface, but with a clip that would allow it to remain clipped to the inside surface. The attachment mechanism could be positionally based so that the element could be repositioned to several locations for a variety of lengths.

There could be several other means for manually actuating the design for repositioning.

As another variation of the above embodiments, the manual expansion mechanism could be adjusted remotely by an apparatus outside the body, and/or automated. The expansion could be achieved by a small motor that could be driven by an implanted power source or driven by a remote power source such as induction. Energy could also be supplied by an RF signal, kinetic energy, ultrasound, microwave, cryogenic temperatures, laser, light, or thermal power. Power could also be supplied by a battery or implantable power cells that utilize glucose or other means for fuel. The automated expansion could also be achieved by a pump, a syringe type plunger, a piezoelectric crystal, a bellows, a Nitinol motor, a pH responsive material that changes shape, thermal expansion of a gas, fluid or solid (example wax) expansion, magnet forces or any other type automated expansion or compression mechanism.

The control for activating this mechanism could be a remote control using a radiofrequency signal which can pass through tissue. The remote control could also be achieved by magnetic fields, time varying magnetic fields, radio waves, temperature variation, external pressure, pressure during swallowing, pH of any frequency or any other type of remote control mechanism.

Actuation Mechanisms

Figure 43:
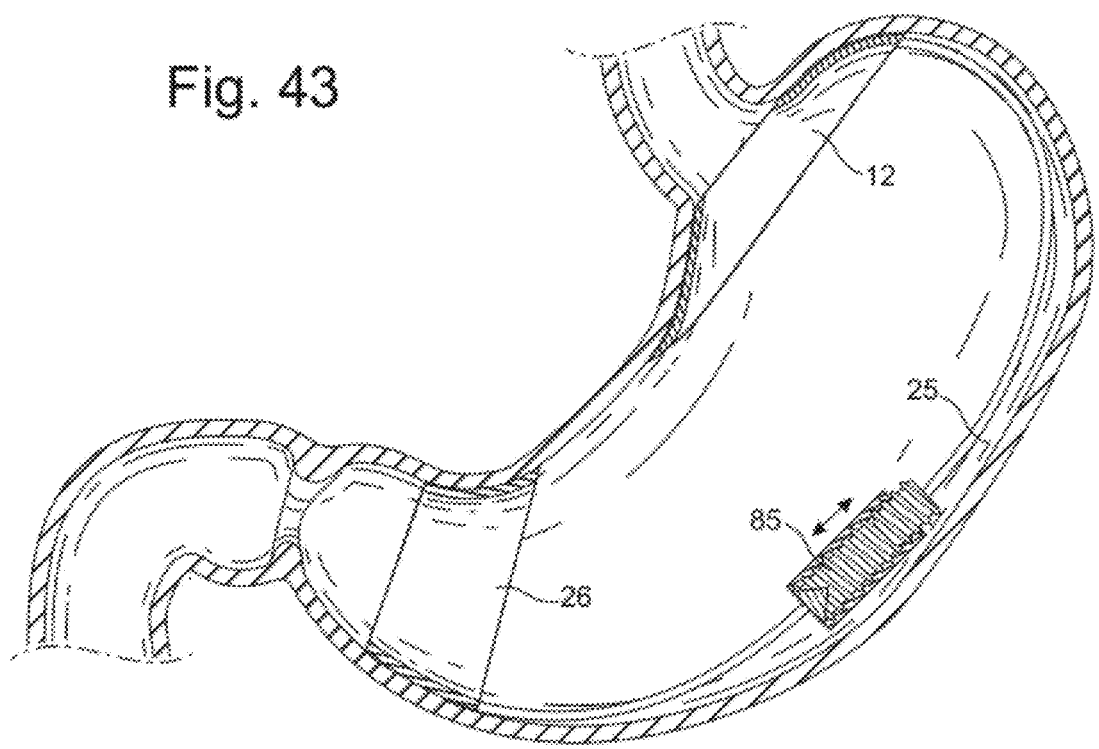
FIG. 43 depicts a side view of an embodiment of the present invention, equipped with adjustment mechanism shown in cross section, located within a cross-section of a stomach.

Stepper Motor:

To adjust the length of the connecting element, 25 to increase the direct force onto the upper stomach or cardia 40, the adjusting element could be connecting element, 25 entirely or partially comprised of a flexible, semi-flexible or rigid screw. A stepper motor 85 could be placed onto the flexible thread and could drive forward or back to allow the connecting element, 25 to draw together or push apart the elements. See FIG. 43. These figures represent a threaded element that can be drawn together or apart.

The adjusting element may require power to drive the motor 85. The power could be supplied by an implanted power source such as a battery or it could be powered externally by induction through the coupling of an external antenna and an internal antenna.

An option would be to embed the internal antenna into any or all of the elements. This would allow for fewer structures in the design by encasing the antenna inside of one or more of the existing elements. The antenna could be a simple ring at the top or bottom or obliquely on either element or it could be placed in the wall of the device 10. The internal antenna could also be attached by a tether, free floating inside the esophagus, stomach or intestine. These could be made from materials to make them MRI compatible and/or MRI safe. This feature could be applied towards any actuation method where it is powered by induction.

For induction, an external hand held controller 86 may be required to transmit power for coupling. See FIGS. 44 and 45. The controller 86 could be set up to auto detect the internal antenna's presence and identify when coupling between the two antennas was adequate to allow for transmission and powering to take place, and to inform the user of function. This external controller 86 could then be used to display the distance that the stepper motor 85 had been advanced or retracted to allow the physician to control the adjustment. Similarly, the external controller 86 could be used for communication and control signals as an interface between the physician and the placed device 10. This feature could be applied towards any actuation method powered by induction.

An external antenna would be required for induction and could be placed into an external handheld controller 86. This could be placed directly against or close to the patient's body at the height of the internal bariatric device 10. The antenna could be housed with the other controller electronics in a single unit. This feature could be applied towards any actuation method powered by induction.

Another alternative would be to have the external antenna in the form of a belt 87 that would wrap around the patients abdomen at the height of the device 10 to better align the antennas for improved coupling. This feature could be applied towards any actuation method powered by induction.

The location of the actuation mechanism could also be inside any of the elements, or above or below any of them, or another location as would be best suited for the anatomy and function of the device 10. This feature could be applied towards any actuation method. Actuation could be accomplished by allowing the screw to be pushed or pulled inside any of the elements to embed the adjustment mechanism internally to one of the other elements. Other actuations mechanisms such as those listed above or others could also be used for this adjustment.

Induction could also be powered by an intragastric instrument. The instrument could have a flexible shaft that could fit through the mouth and down the esophagus or down the working channel of a gastroscope. Once the instrument was placed within or near the esophagus or stomach, it would allow the instrument to be in close proximity with the actuation mechanism in the device 10. The end of the instrument could have antenna(e) to allow for inductive powering and/or communication with the actuation mechanism for adjustment. This feature could be applied towards any actuation method.

Piezoelectric Motor

The adjustment could also be achieved by a piezoelectric element or motor 85. See FIGS. 43. These figures represent a threaded element that can be drawn together or apart.

There are several types of piezomotors that could be used for linear actuation. For example, a motor from NewScale Technologies (www.newscaletech.com) called the Squiggle Motor could be used which is very low profile and can be actuated when powered. Other motors or actuation mechanisms could also be used, and the Squiggle motor is just used as an example. In this example, there is a rigid screw that passes through the center of a threaded piezoelectric "tube" or element. When powered the piezoelectric element flexes side to side along the central axis to create an oscillating "hula hoop" action which causes it to translate axially along the rigid screw. The Squiggle motor could be attached to the connecting element, 25 to advance or retract the cardiac and/or the pyloric element 12, 26. Alternatively, the Squiggle motor could be placed in between any of the elements. Alternatively, more than one Squiggle motor could be placed at these locations. One of the advantages of a piezoelectric motor 85 is that it would allow the device 10 to be MRI compatible and safe. As mentioned with the stepper motor 85 above, the piezoelectric motor 85 could be powered by an internal power source such as a battery or it could be powered by remote induction. The remote induction could be by a handheld external controller or it could be by a gastroscopic instrument placed down the esophagus. This motor could be encased in other materials to keep it dry and protected from the stomach environment.

Another embodiment of a piezoelectric actuated motor 85 would be to have a rotating piezoelectric member that could thread along one or two threaded members similar to a worm gear.

Another embodiment of a piezoelectric actuated motor 85 would be to have a piezoelectric crystal that elongates or flexes to actuate another member.

All of the piezoelectric motors 85 may contain a sealed housing such as an expandable metal or plastic bellows to prevent moisture of fluid from contacting the piezoelectric elements.

Magnetic Actuation

As mentioned above in the manual adjustment section, another adjustment mechanism could use magnets. See FIG. 42.

For example, at least a portion of the connecting element could be a semi-flexible thread or rigid thread with a magnetic nut placed over it. Another strong magnet, named a controller magnet 80, could be placed in close proximity to the implanted magnet to cause it to rotate. The rotation of the controller magnet 80 could create a magnetic field which would cause the internal magnet to turn allowing it to advance and retract along the threaded member.

The controller magnet 80 could either be external to the body or it could be placed on the end of a gastroscopic instrument for close proximity.

The controller magnet 80 could be a magnet or an electromagnet to increase the intensity of the field and to improve magnetic coupling to ensure actuation.

The controller magnet 80 could also be multiple magnets to improve magnetic coupling.

Nitinol Actuation

The adjustment element could also be actuated by Nitinol or a substance with similar properties. When a current is passed through Nitinol, it heats and causes the Nitinol to change its shape. Nitinol can expand into a variety of different shapes. A linear actuator could be made from Nitinol to advance or retract along an actuation member.

Heat could be generated from an implanted battery or it could be delivered by induction.

The connecting element could have multiple positional features such as holes, grooves, teeth or a wedging feature. A Nitinol clip could have a feature to engage these positional features. The Nitinol clip could be heated to change shape to allow it to advance or retract into different positional features to increase or decrease the length.

There are other Nitinol actuations that could be provided as well.

Ultrasound Motor

Another adjustment mechanism could be by use of an ultrasound motor or one powered by external ultrasound. This could use external ultrasound equipment to send sonic waves into the body to actuate the motor. This would also provide an MRI compatible option without requiring an internal power source or induction.

Hydraulic Actuation

Figure 46:
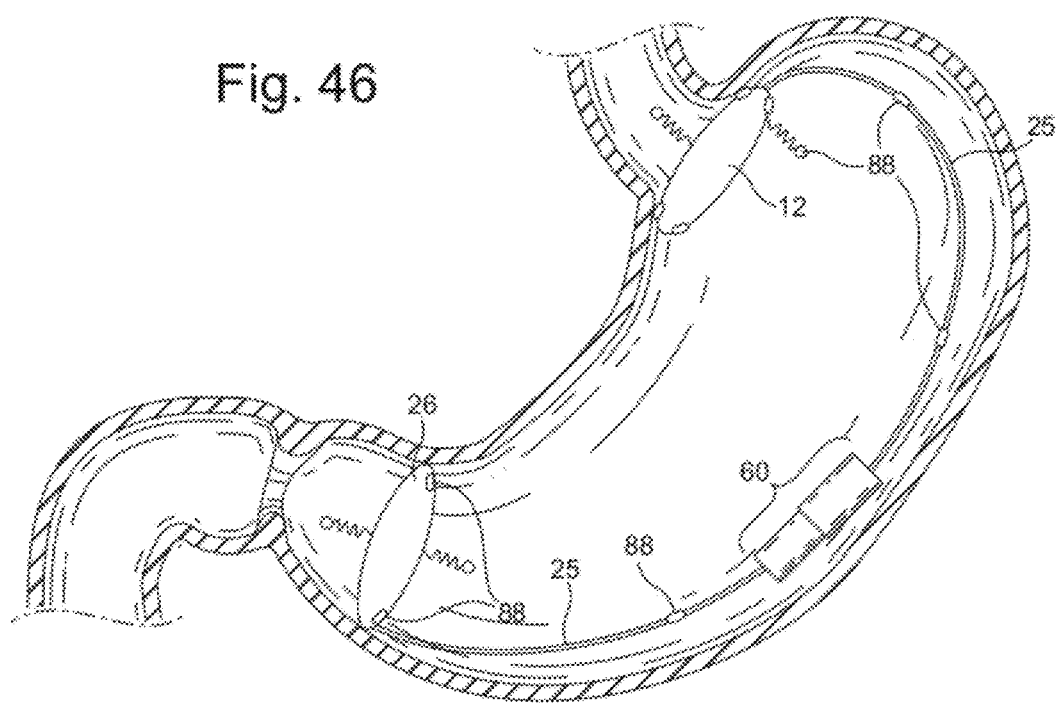
FIG. 46 depicts a side view of an embodiment of the bariatric device of the present invention, located within a cross-section of a stomach.

The adjustment element 60 in FIG. 46 could also be actuated through hydraulic means for radial expansion or linear actuation as previously described. The cardiac or pyloric element 12, 26 could be inflated with a fluid to increase the diameter or length of the device 10 to increase pressures against the upper stomach or cardia 40, and pyloric region 42. It could increase in volume by accessing a self sealing membrane such as a self sealing drug delivery port, self sealing membrane on the expandable body, or a self sealing valve attached to the device 10. The inflation could be achieved by a piezoelectric pump, a peristaltic pump, a positive displacement pump or a syringe pump.

Piezoelectric pump: The pump could be comprised of a piezoelectric element which can flex to propel fluid directly or a member that could propel fluid. For example, a piezoelectric disk could be captured in a housing with an incoming channel and an outgoing channel. The disk could be powered to cause it to flex into a dome shape to push fluid into the outgoing channel. A valve would be required to close the incoming channel to ensure directional flow to the outgoing channel. Similarly, the piezoelectric Squiggle motor as described above could be used to linearly actuate a fluid up or down a tube to hydraulically actuate position.

Stepper motor pump: Actuation could be achieved by a stepper motor where the motor linearly actuates to compress a reservoir or syringe to move fluid within a tube or constrained volume.

Wax expansion pump: Fluid could also be propelled by a wax expansion mechanism. When wax is heated to melting it expands by approximately 30%. A solid plug of wax could be heated to expand and drive fluid through a valve to hydraulically actuate lengthening. The lengthening structure could be made to move only in one direction, so that when the wax cools it will not contract. The wax expansion could also be used to actuate other adjustment mechanisms.

Peristaltic pump: The members could also be driven by a peristaltic pump. In this mechanism, the external diameter of a cylindrical actuator could be used to compress a length of tubing to create an occlusion. The cylindrical actuator could be rotated along the tube to drive fluid forward or backwards inside the tube. The peristaltic pump could also be actuated by a stepper motor or by a piezoelectric element or other.

Gas expansion/propellant pump: The length could also be actuated by a gas expansion pump where a gas like Freon or others could be used to expand when exposed to a higher temperature. Similar principles to the devices like the Codman pump could be used. This change in volume could drive the pump forward. Similarly, there could be compressed gas constrained in a pressure vessel with a valve. The valve could be remotely activated to allow gas to propel a syringe, fluid or to compress a constrained volume.

Positive displacement pump: There are implant grade positive displacement pumps that are available on the market for drug delivery that could be used to displace a specific amount of fluid for hydraulic inflation of the adjustment element 60.

Syringe pump: A syringe pump could be made by advancing fluid through a syringe. The syringe could be actuated by a stepper motor, a piezoelectric actuator, a magnet or by a Nitinol actuator as described above.

Hydrogel: the adjustment element could also be inflated by use of a hydrogel to absorb fluids and could be actuated by changes in temperature, pH or tonicity to change shape or volume Hypertonic fluid: the adjustment element 60 could also be inflated by using a hypertonic fluid in the inflation area and allowing it to absorb fluid across a semi permeable membrane.

Mechanical means for diametrical changes. Similar to the inflation, elongation, and shortening embodiments described above, the device 10 could change diameter by various actuation mechanisms. All of the above-described mechanisms could also be adapted for use for a diametric change instead of a linear change.

As a variation of the embodiments discussed above, the device 10 could have a sensor 88 that could sense a parameter such as pressure, motion, peristalsis, tension, pH, temperature, chemical or other appropriate parameters, or various parameter combinations. The sensor 88 could output a signal to be used by an actuation element to actuate an adjustment element, to a memory element such as a microchip, or be read by a remote reader or remote controller.

Sensors 88 could be used to gather important patient data to understand performance, patient status or whether an adjustment needs to be performed. For ease of use and compatibility with the body, wireless sensors would be preferred. The sensors 88 could be direct tissue contact, intermittent patient contact or could monitor the intraluminal pressure inside GI tract. The data could be used for no other reason than to just monitor patient status. FIG. 46 depicts sensors 88, which could be embedded in any of the elements or it could be tethered to any of the elements to allow it to be suspended inside the GI tract. Based on the sensed parameter, the device 10 could be adjusted. The adjustment could have an open or closed loop system increasing or decreasing the applied force, pressure or sensed parameter. The sensed parameter could detect whether the device 10 was not at an ideal condition, and could then send a signal to a control mechanism for automatically adjusting the system. This mechanism could be under physician control (open system) or without physician control (closed system). The adjustment could also be a manual adjustment where the parameters are being monitored to guide the adjustment. It could also control the shape of the cardiac, pyloric, and/or connecting elements 12, 26, 25 to vary stiffness, size, length, form or shape. In general, the sensor 88 could sense a parameter and then adjust the device 10 as needed to bring the sensed parameter into the ideal range. There could be an algorithm that controls the ideal parameter or it could be based on a parameter range. The device 10 would be adjustable to meet the needs of the patient.

In an open loop system, the physician would have control of when the device 10 would adjust. The device could have it owns internal power source or the device 10 could be passive and only inductively powered when in close proximity to an external controller under the supervision of a physician. For example, in the clinic the physician could have a remote controller with the ability of powering the device 10 inductively, and then begin to monitor the sensors feedback signals to see physical parameters of the patient at baseline such as pressure of the device 10 against the cardia. The sensor monitoring could also be performed while the patient is eating or drinking, or not eating or drinking. As the patient consumes, the esophageal and stomach peristaltic waves will increase in intensity as they propel the food or drink from the mouth to the stomach. A sensor 88 could detect when these waves increase in amplitude, frequency, and pressure. The parameter could read on the external controller by the physician, and then the physician could send a signal to the automated expansion mechanism in the device 10 to adjust the device. The physician could then query the sensor 88 again to determine whether the device 10 was in the ideal settings and whether the pressure against the cardia or sensed parameter was optimized. The physician could iteratively control the amount of adjustment and monitor the parameters until the ideal condition was met. Where the device has its own power source, the physician may still have the control to wake up the device, query the sensors and then adjust the device as described above. The only difference would be that the device was powered by the power source and not require inductive power from outside.

Alternatively, the physician could read the parameter signals while under his supervision, but have the sensors 88 send a signal directly to the automated expansion mechanism to adjust until the device 10 was within the ideal parameters. The data collected could be analyzed by the controller for averages, minimums, maximums and standard deviations over time and use an algorithm to determine the ideal settings. The controller could then monitor and adjust on its own until the ideal conditions were met, but while the physician was present to verify all conditions and verify patient acceptance.

In a closed loop system, the device 10 would be active with its own integrated power source. The device 10 could wake up at routine intervals to monitor or could monitor all the time. The data collected could be analyzed for averages, minimums, maximums and standard deviations over time and use an algorithm to determine the ideal settings. As the patient begins to consume food or drink, the device sensors 88 would detect the sensed parameter and signal the automated expansion/contraction mechanism to adjust the device 10 as needed. In this embodiment, the device 10 could be fully automated and would not require intervention from an outside individual.

In either the open or closed loop system, there could be multiple sensors 88 on the device 10 to determine the pressure or force areas, or other sensed parameters on the device 10 and where it needs to be varied to meet the ideal conditions for the stomach. In the case where the connecting element 25 has multiple components, this could be used to align the device 10 in the stomach to provide a custom fit for each person. There could also be a mechanism to adjust the alignment of the cardiac and/or pyloric elements 12, 26 relative to the connecting element 25. The sensor(s) 88 could have a built in power source or it could have a remote power source such as induction so that it would only wake up and activate when an external controller was brought near.

The device 10 could have integrated memory to allow storage of patient and device 10 data. This could include but is not limited to the serial number, the patient's information such as name, patient number, height, weight; the physician's name, the adjustment history including the date and time, the amount adjustment and the sensed parameters. For the active device, there could be 24 hour data recording of key parameters or there could be data collected at key intervals throughout the day to detect when the patient is eating and whether they are being compliant with their eating. It could record weight tracking, BMI or other data as needed which could be queried by an external controller. This data could also be downloaded into a physician's patient tracking database for ease of patient tracking. Similarly, this data could be downloaded and tracked on an internet tracking website, where the patient could log on and see their history and progress. The patient could add information to the website such as weight or an eating log, adverse events or other conditions that the physician or patient would like to track.

In the open system, the physician could choose to collect and record data as needed at the time of the adjustment such as weight, date, time, and adjustment amount or other.

For an open loop system, the device 10 could be adapted to allow for remote adjustments over the phone. This would be especially advantageous for patients living in rural areas where they are far from their physician's office. It could also be for convenience of having an adjustment without having to travel to the physician's office. This would allow a physician to discuss the patient's progress with the patient directly and then query the device sensor 88 to see how the device performance is. Based on the feedback of the device 10, the physician could then adjust the patient.

In yet another embodiment, the device 10 could have an emitter element for dispensing a drug, hormone or bioactive agent to further induce satiety, weight management or other disease management such as diabetes. The drug could be a weight management drug currently on the market or one to be developed. Similarly, it could be a satiety hormone or other bioactive agent. In the published literature, there is a growing mass of information on satiety hormones. The bioactive agent could be applied by the emitter element through a drug eluting coating, a reservoir with a pump, or a permeable membrane placed on the device 10 where the drugs could pass from the device 10 into the gut. The emitter element could release such substances in response to a signal from a sensor 88, a timed basis, or other release criteria. The device 10 could have a tube that trails into the intestines to allow the drug to be delivered downstream where the pH is higher and would not destroy the bioactive agent.

The device 10 could have a surface finish or macrotexture for gripping the stomach. If the device 10 could grip the inner mucosa of the stomach, it could elongate or expand to further stretch the stomach in key areas to induce further satiety as needed. For example, the cardiac element 12 could be a conical spiral with a surface texture that lightly grips the mucosa and or stomach musculature. If the spiral were made of Nitinol or other temperature-sensitive substance, the device 10 could expand the spiral by a variation of temperature. By applying a temperature variation, such as by drinking a hot liquid or otherwise, the device 10 could expand and cause a satiety response. The surface could be multiple protuberances, barbs, a rough bead blast, or other finishes suitable for gripping the stomach wall.

Figure 47:
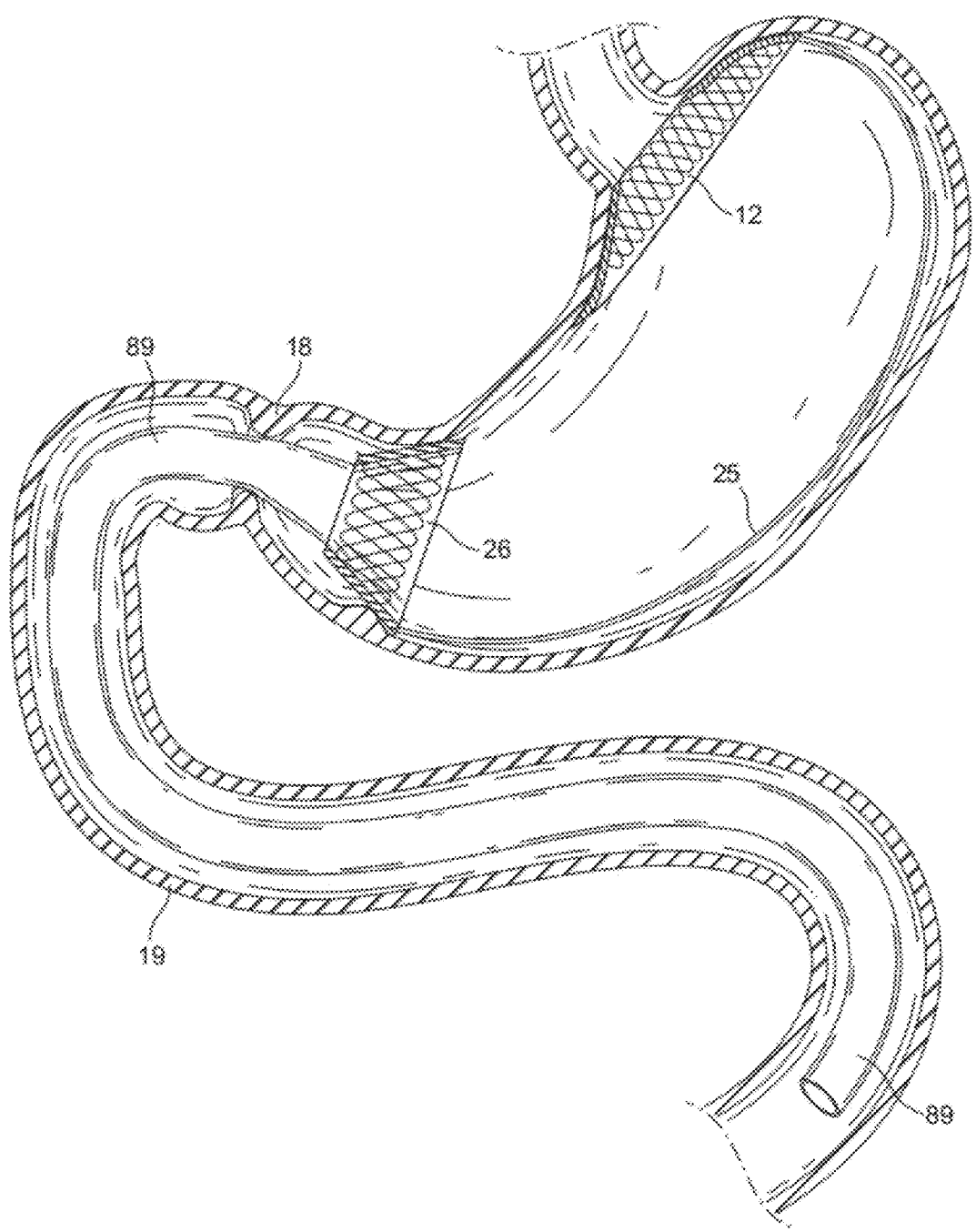
FIG. 47 depicts a side view of an embodiment of the bariatric device of the present invention, located within a cross-section of a stomach and a duodenum.

The device 10 could have a thin flexible tube 89 attached to the pyloric element 26 that could trail into the duodenum 19 to act as a barrier to food absorption. See FIG. 47. This tube 89 would be of similar diameter to the duodenum 19 and all food passing through the pyloric element 26 would pass directly into this sleeve. Similar to the rerouting performed in a gastric bypass or Roux en Y bypass, the sleeve 89 would be approximately 100 cm long, but could be longer or shorter depending on the amount of malabsorption required. This tube 89 may be made of an acid resistant material such as Teflon, PTFE, ePTFE, FEP, silicone, elastomers or other acid resistant materials.

As a variation of the device 10, it could incorporate electrical stimulation to the stomach musculature, stomach nerves or the vagus to further improve satiety stimulation and weight loss. Energy used for this stimulation could be RF, ultrasound, microwave cryogenic, laser, light, electrical, mechanical or thermal. The device 10 could have leads incorporated that could embed into the stomach wall or be surgically placed around a nerve, or the stimulation could be applied directly through surface contact of the device 10 to the stomach mucosa.

In yet another embodiment, the bariatric device 10 may have an adjustment element 60 that is equipped with a temporary expansion/contraction element that may allow for temporary adjustment based on activation of a material property, sensor 88 or mechanism of the device 10. This could be applied to any of the above-discussed embodiments. It may be desirable for the temporary expansion/contraction element to adjust only upon eating, and then retract after eating. It may be desirable for the device 10 to adjust with the pH cycle of the patient where pH will be higher prior to eating and then lower after eating. This would allow for intermittent stimulation of the stretch receptors to avoid receptor fatigue over time. For example, the material could be heat sensitive using materials such as Nitinol, which could expand after consuming a hot liquid. Similarly, the device 10 could have a sensor 88 or material that is pH or glucose sensitive or detect the presence of food, which could activate the temporary expansion/contraction element to expand when a certain threshold for pH has been reached or glucose or fat is present after eating. Similarly, this temporary expansion/contraction element could be activated by a magnetic field such as swallowing a magnetic pill that could temporarily expand the device 10. In this example, the magnetic pill would be small enough and shaped appropriately for passage through the gastrointestinal tract, and biocompatible. The patient could consume the electromagnetic oil when a satiety signal was desired. It may also be desirable for the device 10 to adjust based on time or sleep cycle such that the device 10 adjusts at specific times of the day or when the patient lays horizontal. Other parameters or mechanisms to trigger the temporary expansion could be used.

Placement

As mentioned above, a tube, catheter, or sheath may be required to protect the anatomy during placement of the device 10 down the esophagus and into the stomach. It could be a simple flexible tube such as silicone or urethane tube to aid in straightening and compressing the device 10 while it is being introduced. Insertion of the device 10 into the tube would require compression of the device 10 into a narrow, insertable shape. A standard gastroscopic tool could be used to push or pull the device 10 down the tube. Similarly, a custom gastroscopic tool or sheath could be used to introduce the device 10 into the stomach through the esophagus or other narrow opening.

Removal

For removal, a flexible tube such as a standard overtube could be used with a standard or custom endoscopic tool. The tube may be placed down the esophagus and the tool then placed down the lumen of the overtube. A standard tool such as a grasper or snare could grasp the device 10 and pull it up the tube. The device 10 would be straightened by the overtube for removal from the stomach and esophagus.

In another embodiment, the elements may incorporate a collapsing mechanism designed to collapse the element into a compact shape for removal. For example, a constriction member comprising a wire or thread sewn spirally around, through, or inside the length of the element. When the constriction member is pulled, it tightens the circumference of the pyloric element like a drawstring, which collapses the element down to a narrow profile that can be safely removed through the esophagus or other narrow opening, or ease its placement into a tube for removal. Similar collapsing mechanisms can be installed in the cardiac, and/or connecting elements 12, 25. The constriction member could be made from Nitinol, stainless steel wire, ptfe thread, eptfe thread or ptfe coated threads or other suitable materials. The constriction member could be integrated into the elements in a variety of patterns such as a continuous spiral, two spirals of reversing orientation, or other.

Figure 48:
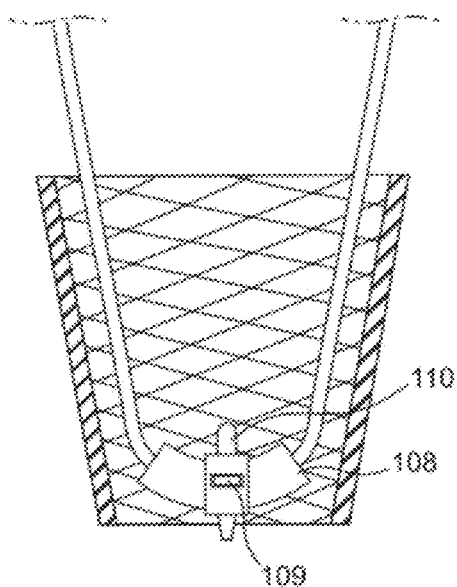
FIG. 48 depicts a side view of a modular clip mechanism of an embodiment of the present invention.
Figure 49A:
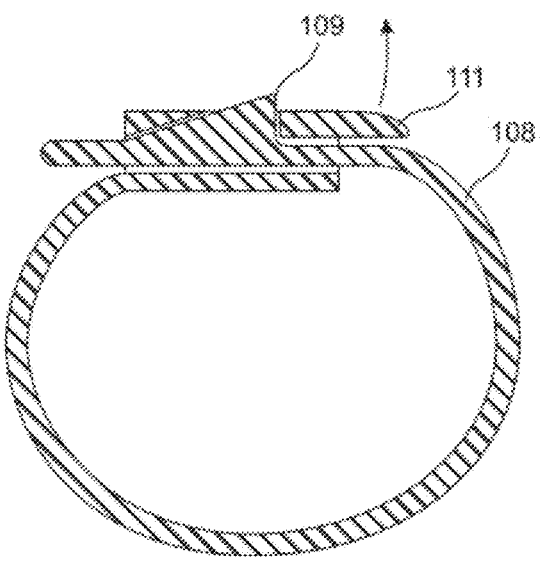
FIG. 49A depicts a side cross-section view of a modular clip in a closed position of the embodiment of FIG. 48.
Figure 49B:
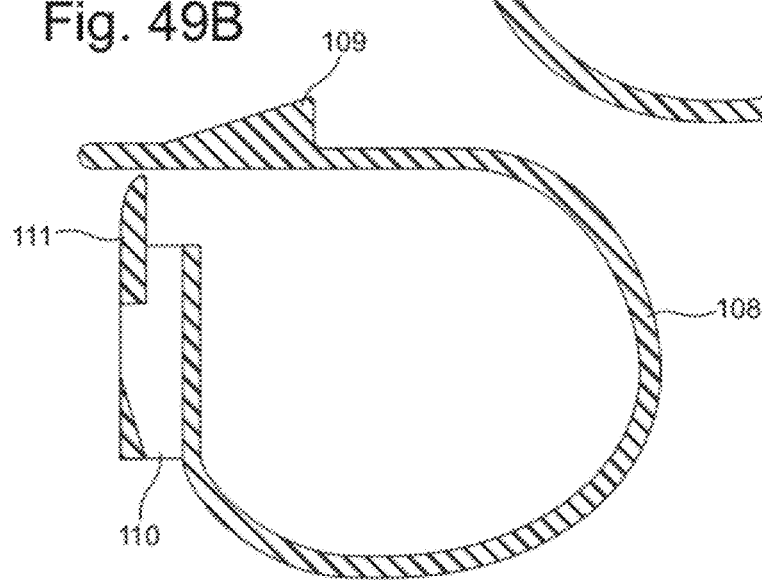
FIG. 49B depicts a side cross-section view of a modular clip in an open position of the embodiment of FIG. 48.
Figures 50A, 50B:
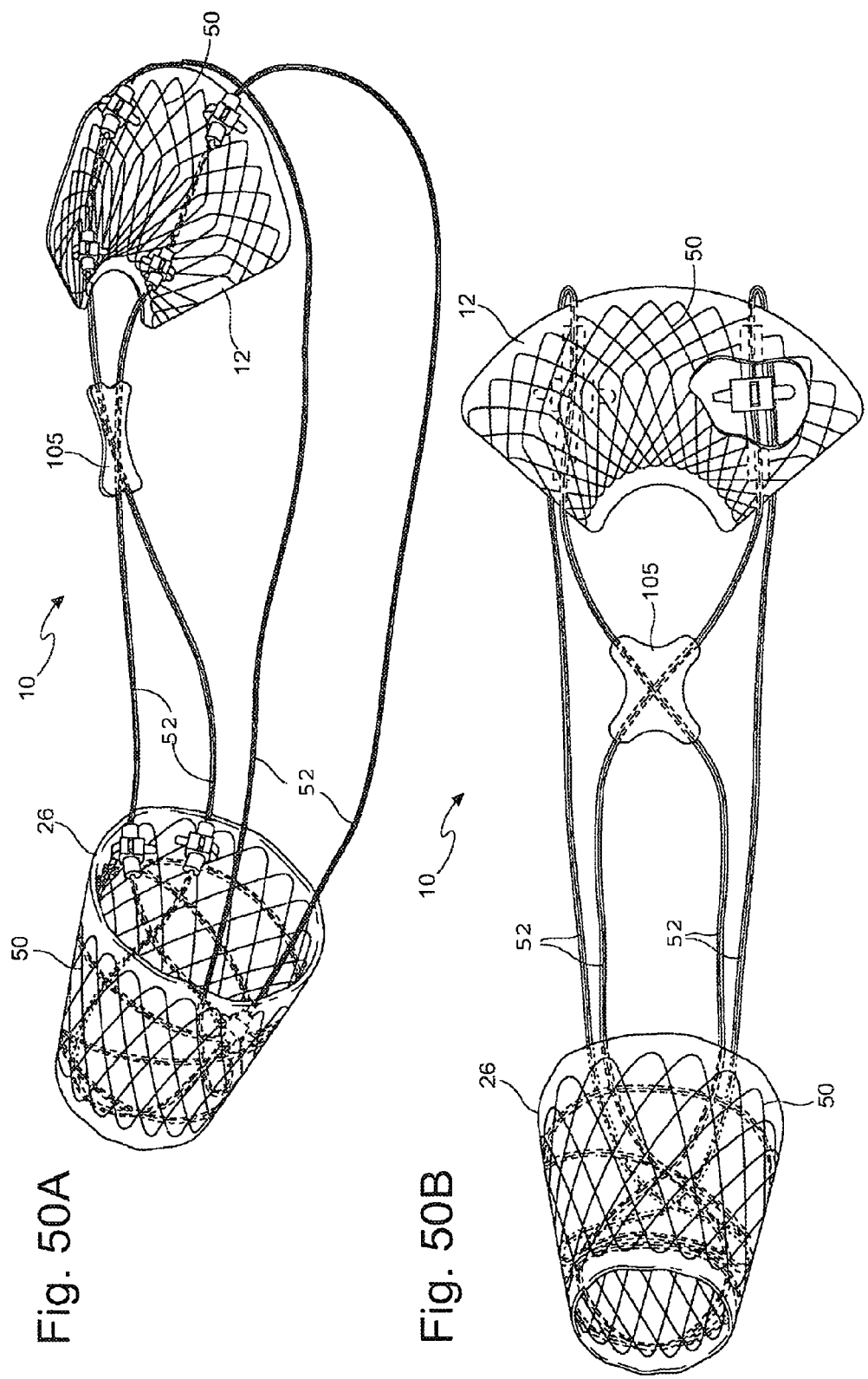
FIG. 50A depicts an underside perspective view of an embodiment of the bariatric device of the present invention with modular clips.
FIG. 50B depicts a front view of an embodiment of the bariatric device of the present invention with modular clips.

In another embodiment, the connection of the cardiac, pyloric and connecting element may be equipped with a release element, which would allow the cardiac, pyloric and/or connecting elements to be releasable, cut-able or modular, as to allow the device to be disassembled into components for ease of removal. FIGS. 48, 49A and 49B show a release element in the form of a releasable clip 108 in the closed and open positions. The clip could be made of an elastomer or polymer or other, but would need adequate flexibility to allow the clip to close and then re-open. The clip has a locking tooth 109 which compresses when pulled through a narrow channel 110, and then expands into an opening to lock the clip into position. To release the clip, the release tab 111 is pulled upward which allows the narrow channel to flex open, and the locking tooth 109 is released. FIG. 48 shows as side view of the releasable clip in the locked position in a suggested location to attach a connecting element to another element. A release element like this could be bonded or incorporated into the cardiac and pyloric elements and then could be locked around the connecting element to secure the assembly. When the device is ready for removal, standard instruments could be used as a releasing tool under the visualization of a gastroscope to release the tabs to disassemble the pyloric 26 and/or cardiac element 12 from the connecting elements 25. Then each element or combination of elements could then be removed up the esophagus or through an over tube. As described above, the pyloric or cardiac elements could still contain a collapsing member to further collapse the element for removal. The connections could be placed over a single section of the connecting element or it could be placed over a joint to join two connecting elements. The connection length could be a short distance or it could be a relatively long distance. With a short distance, several clips could be used to join a connecting element to a cardiac or pyloric element such as shown in FIG. 50A. With a long element, one clip could feasibly connect the two elements such as shown in FIG. 50B. FIGS. 50A and 50B show an example of release elements where the modular clips could be used to connect the cardiac, pyloric and connecting elements, 12, 25, 26. These are only examples of where a connection could be located, but other locations could be used. Similarly, this modular clip only shows one type of clip, but several other options could be used.

The modular connection of the components could be equipped with release elements comprising many different mechanisms such as other clip designs, ties and could also provide an area where the connection is to be cut by a releasing tool, such as endoscopic scissors or electro-cauterizer, or other custom tools. In another embodiment the connecting elements could be sewn into the pyloric and cardiac elements with acid resistant thread such as ePTFE thread and/or cloth. The thread or cloth could be cut by a releasing tool such as surgical scissors or an electro-cauterizer for removal. The connection could be made of many different materials such as silicone, nitinol, polymers, super alloys, or other suitable materials that can withstand the acidic environment of the stomach. Likewise, the releasing tool could be many different endoscopic instruments.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

INDUSTRIAL APPLICABILITY

This invention may be industrially applied to the development, manufacture, and use of bariatric devices for weight loss purposes.

What is claimed is:

1. A bariatric device for placement into a stomach to achieve weight loss, comprising:
   a. a first element shaped and sized to contact at least one-third of a circumference of a cardia of the stomach, the first element formed as a first curved shell having a convex side constructed to contact and face the cardia and having a concave side, opposite the convex side, facing and open to the interior of the stomach, and wherein the first shell has a first restriction element formed therein that restricts fluid flow through the first shell from the convex side to the concave side of the first shell, wherein on the concave side the first restriction element is in direct fluid communication with the interior of the stomach;

b. a second element formed as a second curved shell having a convex side constructed to contact a pyloric region of the stomach and having a concave side opposite the convex side facing and open to the interior of the stomach and the concave side of the first shell, and wherein the second element has a second restriction element formed therein that restricts fluid flow through the second shell from the concave side to the convex side; and c. a connecting element coupling the first element and the second element, such that the first or the second element maintains at least intermittent contact with the cardia and the second element maintains at least intermittent contact with the pyloric region of the stomach, wherein:
the connecting element includes a plurality of connecting members each extending from the first element to the second element, the plurality of connecting members includes at least a first connecting member and a second connecting member, and the first connecting member is constructed to extend along the lesser curve of the stomach and the second connecting member is constructed to extend along the greater curve of the stomach.

2. The bariatric device of claim 1, wherein the connecting element is constructed to impart at least an intermittent outwardly biasing force against both the first element and the second element.

3. The bariatric device of claim 1, wherein the first element and the second element are constructed of a resilient, shape-retaining material, such that when either the first or second element is in the pyloric region, the element folds to fit the pyloric region, and is sized so that it will not contact a pyloric valve in the pyloric region.

4. The bariatric device of claims 1, wherein the first element and the second element are symmetrically arranged on the connecting element.

5. The bariatric device of claim 1, wherein:
the first connecting member has a first length and the second connecting member having a second length different from the first length.

6. A bariatric device for placement into a stomach to achieve weight loss, comprising:
a. first element shaped and sized to contact at least one-third of the circumference of a cardia of the stomach, the first element formed as a first curved shell having a convex side constructed to contact the cardia and having a concave side, opposite the convex side, facing and open to the interior of the stomach, and wherein the first shell has a first restriction element formed therein that restricts fluid flow through the first shell from the convex side to the concave side of the first shell, wherein on the concave side the first restriction element is in direct fluid communication with the interior of the stomach;

b. a second element formed as a second curved shell having a convex side constructed to contact a pyloric region of the stomach and having a concave side opposite the convex side facing and open to the interior of the stomach and the concave side of the first shell, and wherein the second element has a second restriction element formed therein that restricts fluid flow through the second shell from the concave side to the convex side; and c. a connecting element coupling the first element and the second element, wherein the second element is located distally in the stomach from the first element, wherein the connecting element includes a plurality of connecting members each extending from the first element to the second element, and wherein the plurality of connecting members includes at least a first connecting member having a first length and a second connecting member having a second length different from the first length.

7. The bariatric device for placement into a stomach to achieve weight loss of claim 6, wherein the connecting element imparts an outwardly biasing force to the first element and the second element.

8. The bariatric device for placement into a stomach to achieve weight loss of claim 7, wherein the first element and the second element are substantially the same shape.

9. The bariatric device for placement into a stomach to achieve weight loss of claim 7, wherein the second element is sized to fit proximal to and adjacent to the pyloric region.

10. The bariatric device for placement into a stomach to achieve weight loss of claim 6, wherein the second element is sized to fit the proximal pyloric region.

11. The bariatric device for placement into a stomach to achieve weight loss of claim 6, wherein the second element is sized and constructed so that it will not contact the pyloric valve.

12. The bariatric device of claim 6, wherein the first connecting member is constructed to extend along the lesser curve of the stomach and the second connecting member is constructed to extend along the greater curve of the stomach.

* * * * *